US008686113B2

(12) United States Patent
Hoffmann et al.

(10) Patent No.: US 8,686,113 B2
(45) Date of Patent: Apr. 1, 2014

(54) ANTIBIOTIC PEPTIDES

(75) Inventors: Ralf Hoffmann, Grosspoesna (DE); Daniel Knappe, Leipzig (DE); Anna Klara Brigitte Hansen, Gehrden (DE)

(73) Assignee: AMP-Therapeutics GmbH, Leipzig (DE)

( * ) Notice: Subject to any disclaimer, the term of this patent is extended or adjusted under 35 U.S.C. 154(b) by 69 days.

(21) Appl. No.: 13/147,095

(22) PCT Filed: Jan. 29, 2010

(86) PCT No.: PCT/EP2010/051072
§ 371 (c)(1),
(2), (4) Date: Oct. 7, 2011

(87) PCT Pub. No.: WO2010/086401
PCT Pub. Date: Aug. 5, 2010

(65) Prior Publication Data
US 2012/0021975 A1 Jan. 26, 2012

(30) Foreign Application Priority Data
Jan. 29, 2009 (DE) .......................... 10 2009 007 381

(51) Int. Cl.
*A61K 38/10* (2006.01)
*A61P 31/04* (2006.01)
*C07K 1/00* (2006.01)
*C07K 7/08* (2006.01)

(52) U.S. Cl.
USPC .............. 530/326; 514/2.4; 514/3.3; 530/333

(58) Field of Classification Search
None
See application file for complete search history.

(56) References Cited

U.S. PATENT DOCUMENTS

| 5,300,629 A | 4/1994 | Casteels et al. |
| 2002/0041898 A1 | 4/2002 | Unger et al. |
| 2003/0104622 A1* | 6/2003 | Robbins et al. ............... 435/455 |
| 2005/0058603 A1 | 3/2005 | Gao et al. |
| 2005/0282755 A1* | 12/2005 | Hart et al. ...................... 514/14 |
| 2006/0003938 A1 | 1/2006 | Otvos |

FOREIGN PATENT DOCUMENTS

| WO | WO 95/23513 A | 9/1995 |
| WO | WO 00/78956 A | 12/2000 |
| WO | WO 02/079467 A2 | 10/2002 |
| WO | WO03/062266 A2 | 7/2003 |
| WO | WO 2009/013262 A1 | 1/2009 |

OTHER PUBLICATIONS

Rosengren et al, Cyclization of Pyrrhocoricin Retains Structural Elements Crucial for the Antimicrobial Activity of the Native Peptide, Biopolymers, 2004, 76, pp. 446-458.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Rosengren, et al., "Cyclization of pyrrthocoricin retains structural elements crucial for the antimicrobial activity of the native peptide", Bipolymers—Peptide Science Section 2004, vol. 76, No. 5, 2004, pp. 446-458.
Kragol, et al., "Identification of crucial residues for the antibacterial activity of the proline-rich peptide, pyrrhocoricin" European Journal of Biochemistry, vol. 269, No. 17, Sep. 1, 2002, pp. 4226-4237.
Borysowski, et al., "Fusion to cell-penetrating peptides will enable lytic enzymes to kill intracellular bacteria", Medical Hypotheses, vol. 74, No. 1, Jan. 2010, pp. 164-166.
Tomasz, A. "Muitiple-antibiotic-resistant bacteria ", New England J. Med., 1994, 330:1247-1251.
Wenzel, R.P. (1988) The mortality of hospital-acquired bloodstream infections: need for a vital statistic?, Int. J. Epidemiol. 17:225-227.
Moellering, R.C., Jr. (1898) Problems with antimicrobial resistance in Gram-positive cocci, Clin. Infect. Dis. 26:1177-1176.
Hand. W.L. (2000) Current challenges in antibiotic resistance, Adolesc, Med. 11:427-436.
Hooper, D.C. (2001) Emerging mechanisms of fluoroquinolone resistance. Emerg, Infect, Dis. 7:337-341.
Jones, R.N. (2001) Resistance pattern among nosocornial pathogens: trend over the past few years, Chest 119:397S-404S.

(Continued)

*Primary Examiner* — Julie Ha
*Assistant Examiner* — Li Ni Komatsu
(74) *Attorney, Agent, or Firm* — Fanelli Haag & Kilger PLLC

(57) ABSTRACT

The invention relates to a peptide or peptide derivative having the general formula: $Sub_1$-$X_1$-$D_2K_3$-$P_4$-$P_5$-$Y_6$-$L_7$-$P_8$-$R_9$-$P_{10}$-$X_2$-$P_{12}$-$P_{13}$-$R_{14}$-$X_3$-$I_{16}$-$P_{17}$/$Y_{17}$-$N_{18}$-$N_{19}$-$X_4$-$Sub_2$, wherein $X_1$ is a non-polar, hydrophobic group or a positively charged group, $D_2$ is asparagine or glutamine, $K_3$, $X_2$, and $X_4$ are positively charged groups, $X_3$ is a positively charged group, proline, or a proline derivative; $L_7$ and $I_{16}$ are non-polar, hydrophobic groups, $Y_6$ and $Y_{17}$ are tyrosine, $R_9$ and $R_{14}$ are arginine, $N_{18}$ and $N_{19}$ are asparagine or glutamine, $P_4$, $P_5$, $P_8$, $P_{10}$, $P_{12}$, $P_{13}$, and $P_{17}$ are proline, hydroxyproline, or derivatives thereof, wherein possibly one or two of the groups selected from $D_2$, $P_4$, $P_5$, $P_8$, $P_{10}$, $P_{12}$, $P_{13}$, $P_{17}$, and $Y_{17}$ are replaced by an arbitrary group and/or $P_{13}$ and $R_{14}$ are exchanged, $Sub_1$ is the free or modified N-terminus, and $Sub_2$ is the free or modified C-terminus. The invention further relates to the use of the peptides and peptide derivatives in medicine, as an antibiotic, in a disinfectant or cleaning agent, as a preservative or in a packaging material, in pharmaceutical research, or in a screening method.

7 Claims, 9 Drawing Sheets

(56) References Cited

OTHER PUBLICATIONS

Prachayasittikul, V., Lawung. R., and Bulow, L. (2000) Episome profiles and mobilization beta lactamase plasmid in Haemophilus ducreyl. Southeast Asain J. Trop. Med. Public Health 31:80-84.
Teuber, M. (1999) Spread of antibiotic resistance with food-borne pathogens, Cell. Mol. Life Sci. 30:755-763.
Doppelt: Boman, H.G. (1995) Peptide antibiotics and their rote in innate immunity. Annu. Rev. Immunol. 13:61-92.
Barra, D., Simmaco, M., and Boman, H.G. (1998) Gene encoded peptide antibiotics and innate immunity. Do 'animacules' have defense budgets? FEBS Lett. 430:130-134.
Ludtke, S., He, K., and Huang, H. (1995) Membrane thinning caused by magainin 2, Biochemistry 34:16764-16769.
Wimley, W.C., Seisted, M.D., and White, S.H. (1994) Interactions between human defensins and lipid bilayers: evidence for formation of multimeric pores, Protein Sci. 3:1361-1373.
Shai, Y. (1995) Molecular recognition between membrane-spanning polypeptides, Trends Biochem. Sci. 20:460-484.
Wade, O., Boman, A., Wahlin, B., Drain, C.M., Andreu, D., Boman, H.G., and Merrifield, R.B. (1990) Proc. Natl. Acad. Sci. USA 87:4761-4765.
Steiner, H., Andreu. D., and Merrifield, R.B. (1988) Biochim. Biophys. Acta, 939:260-268.
Otvos, L., Jr., Bokonyi, K, Varga, I., Otvos, B.II Hoffmann, R., Ertl, H.D.J., Wade, J.D., McManus, A.M., Craik, D.J., and Bulet, P. (2000) Insect peptides with improved protease-resistance protect mice against bacterial infection. Protein Sci., 9:742-749.
Casteeis, P., Ampe, C., Jacob, F., Vaeck, M., and Tempst, P. (1969) Apidaecins: antibacterial peptides from honeybees, EMBO J. 8:2387-2391.
Bulet, P., Dimaroq, J.L., Hetru, C., Lagueux, M., Charlet, M., Hegy, G., van Dorsselaer, A., and Hoffmann, J.A. (1993) A novel inducuible antibacterial peptide form Drosophila carries and O-glycosylated substitution J.Biol. Chem., 268:14693-14697.
Mackintosh, J.A., Veal, D.A., Beattie, A.J., and Golley, A.A. (1998) isolation from an ant Myrmecia gulosa of two inducible O-glycosylated proline-rich antibacterial peptides, J. Biol. Chem., 273:6139-6143.
Cocianoich, S., Duponl, A., Hegy, G., Lanot, R., Holder, F., Hetru, C., Hoffmann, J.A., and Bulet P. (1994) Novel inducible antibacterial peptides from a hemipteran insect, the sap sucking-bug Pyrrhocoris apterus, Biochem. J., 300:567-575.
Merrifiled, R.B. (1963) Solid Phase Peptide Synthesis. I, The Synthesis of a Tetrapeptide J. Am. Chem. Soc., 85:2149-2154.
Stemmer, W.P., Crameri A., Ha, K.D., Brennan, T.M., Heyneker, H.L. (1995) Single-step assembly of a gene and entire plasmid from large numbers of oligodeoxyribonucleolides, Gene, 184:49-53.
Gething, M.J, and Sambrook, J. (1961) Cell-surface expression of influenza haemagglutinin from a cloned DANN copy of the RNA gene, Nature, 293:620-625.
Maeno, M., Taguchi, S.: Momose, H. (1993) Production of antibacterial peptide 'apidaecin' using the secretory expression system of Streptomyces, Biosci. Biotechnol. Biochem, 57:1206-1207.
Zhou, Q.F., Luo, X.G., Ye, L., Xi, T. (2007) High-level production of a novel antimicrobial peptide perinerin in Escherichia by fusion expression, Curr. Microbiol., 54:366-370.
Si, L.G., Lui, X.C., Lu, Y.Y., Wang, G.Y., Li, W.M. (2007) Soluble expression of active human beta-defensin-3 in Escherichia coli and its effects on the growth of host cells, Chin. Med. J. (Engl)., 120:708-713.
Noren, C.J., Anthony-Cahill, S.J., Grifith, M.C. and Shultz, P.G. (1989) A general method for site-specific incorporation of unnatural amino acids into proteins, Science, 244:182-186.
Ellman, J., Mendel, D., Anthony-Cahill, S., Noren, C.J., Schultz, P.G. (1991) Biosynthetic method for introducing unnatural amino acids site-specifically into proteins, Meth. Enzymol., 202:301-336.
Anderson, W.F. (1998) Human gene therapy. Nature, 392, Supp., pp. 25-30.

Posnett, D.N., McGrath, H. and Ta, J.P. (1988) A novel method for producing anti-peptide antibodies. Production of site-specific antibodies to the T cell antigen receptor beta-chain, J. Biol. Chem., 263:1719-1725.
Morell, M., Espargaró, A., Avllés, F.X. and Ventura, S. (2007) Detection of transient protein-protein interactions by bimolecular fluorescence complementation: The abl-SH3 case. Proteomics 7: 1023-1036.
G.B. Fields and Noble, R. (1990) Solid phase peptide synthesis utilizing 9-fluorenylmethoxycarbonyl amino adds, Int. J. pept. Pretein Res. 35:161-214.
Hoffmann, R., Vasko M. and Otvos, L., Jr. (1997) Serum stability of phosphopeptides. Anal. Chim. Acta 352:319-325.
Ryge, T.S. and Hansen, P.R. (2006) Potent antibacterial tysine-peptoid hybrids identified from a positional scanning combinatorial iibrary, Bioorg. Med. Chem., 14:4444-4451.
Park, Y., Lee, D.G., Jang, S.H., Woo, E.R., Jeong, H.G., Choi, C.H., and Hahm, V.S. (2003) A Leu-Lys-rich antimicrobial peptide: activity and mechanism, Biochim. Biophys. Acta, 1645:172-182.
Kragol G, at al.. The antibacterial peptide pyrrhocoricin inhibits ATPase actions of DnaK and prevents chaperone-assisted protein folding, Biochemistry, 40:3016-3026, 2001.
Schneider M, et al., Differential infectibty of two pseudomonas species and the immune response in the milkweed bug. Oncopeltus fasciatus (Insecta: Herniptera), Journal of Invertebrate Pathology, 78:135-140, 2001.
Chernysh S., Cociancich S., Briand J.P., Hetru C., Bulet P., The inducible antibacterial peptides of the hemipteran insect Palomena prasina: Identification of a unique family of proline-rich peptides and of a novel insect defensing, Journal of Insect Physiology, 42:81-89, 1996.
Pujals S., Giralt E., Proline-rich, amphipathic cell-penetrating peptides, Adv. Drug. Deliv. Rev, 60(4-5):473-484, 2008.
Tarn J.P., Mora A.L., Rao C., Lipidation as a novel approach to mucosal immunization Modulation of the Immune Response to Vaccine Antigens, 92:109-116, 1998.
Sieber P., An improved method for anchoring of 9-Fluorenylmethoxycarbonyl-Amino Acids to 4-Alkoxybenzyl alcohol resins, Tetrahedron Letters, 28:6147-6150, 1987.
Backes B.J., Ellman J.A., An Alkanesulfonamide Safety-Catch linker for solid-phase synthesis, The Journal of Organic Chemistry, 64:2322-2330, 1999.
Slater T.F., Sawyer B., Strauli U., Studies on Succinate-Tetrazolium Reductase systems. 3. Points of Coupling of 4 different tetrazolium salts, Biochimicha et Biophysica Acta, 77:383, 1963.
Berridge M.V., Tan A.S., Characterization of the cellular reduction of 3-(4,5-dimethyithiazol-2-Y1)-2,5-Diphenyltetrazolium bromide (Mtt)—subcellular-Localization, Substrate dependent, and involvement of mitochondrial electron-transport in Mtt reduction, Archives of Biochemistry and Biophysics, 3003:474-482, 1993.
Gobbo, et al., Journal of Peptide Science, vol. 12, No. Suppl. S, 2006, p. 109 & 29th European Peptide Symposium; Gdansk, Poland; Retrieved from the internet: URL:http//www.29eps.com/docs/0217.doc.
Czihal, et al., "P2084 Antimicrobiai activity of apidaecin peptides" International Journal of Antimicrobial Agents, vol. 29, Mar. 1, 2007, p. S602, XP022039273 ISSN: 0924-8579.
Knappe, et al, "Chemical modifications of short antimicrobial peptides from insects and vertebrates to fight multi-drug resistant bacteria", Biopolymers. vol. 88, No. 4 (2007) p. 612.
Weinstein, "Chemistry and Biochemistry of Amino Acids, Peptides and Proteins, Passage", Chemistry and Biochemistry of Amino Acids, Peptides, and Proteins, vol. 7 (1963), pp. 266-357.
Li Wei-Pen, et al, "Apidaecin-type peptides; Biodiversity, structure-function relationships and mode of action", Peptides, vol. 27, No. 9 (2006), pp. 2360-2359.
Dutta, et al., "Functional mapping of apidaecin through secondary structure correlation", International Journal of Biochemistry and Cell Biology, vol. 40, No. 5 (2007), pp. 1005-1015.
Office Action U.S. Appl. No. 12/670,118, dated Nov. 20, 2012, 21 pages.

\* cited by examiner

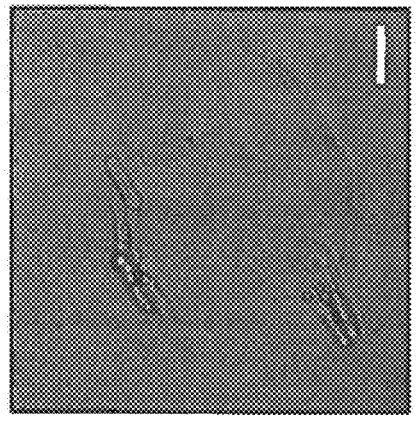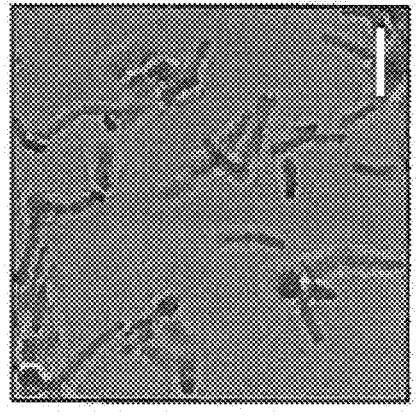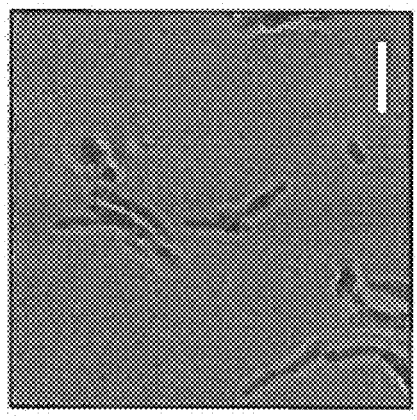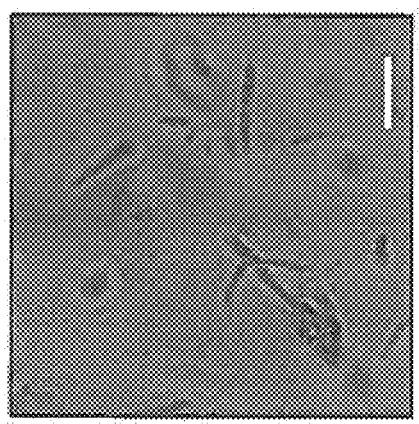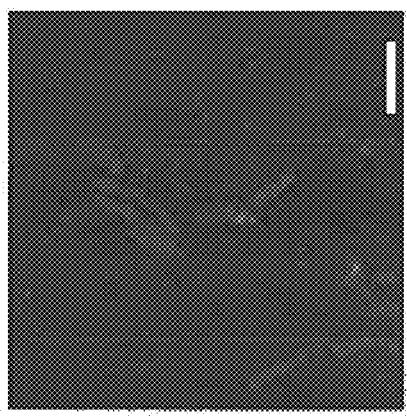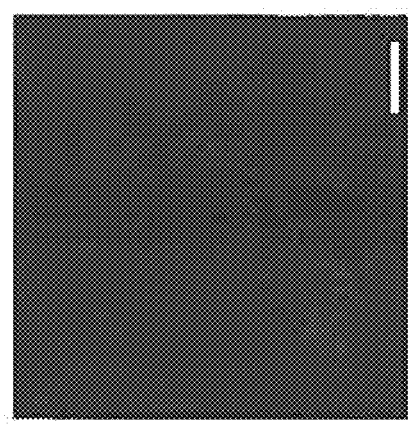

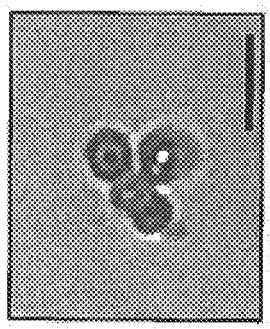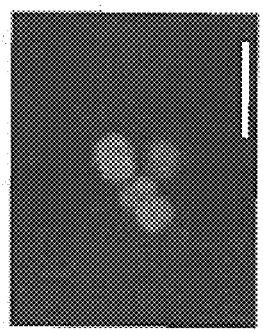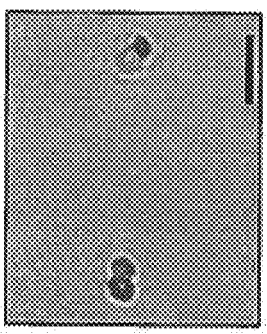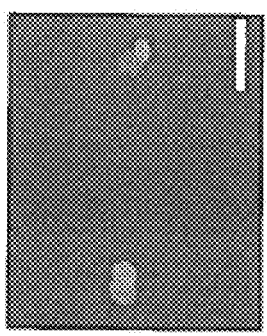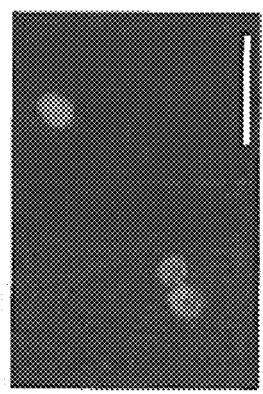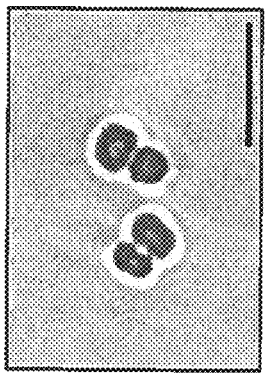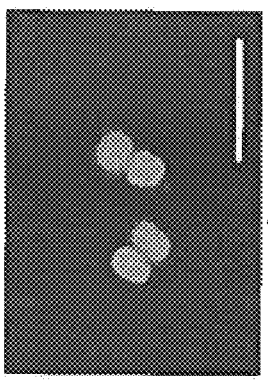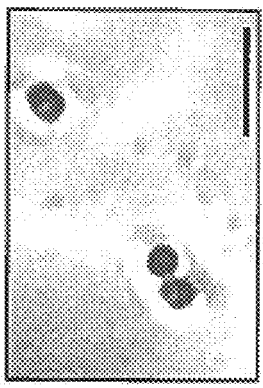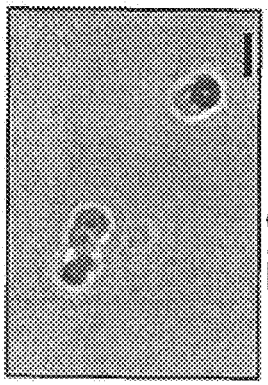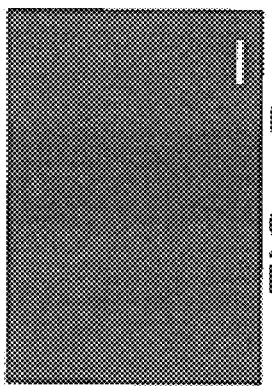

ANTIBIOTIC PEPTIDES

SEQUENCE LIST

The instant application contains a Sequence Listing which has been submitted in ASCII format via EFS-Web and is hereby incorporated by reference in its entirety. Said ASCII copy, created on Jul. 29, 2011, is named 0054_AT01US1_Sequence_Listing.txt and is 49688 bytes in size.

This application is a National Stage of PCT/EP2010/051072, filed Jan. 29, 2010 which claims priority to German Application No. 102009007381.7, filed Jan. 29, 2009, the disclosures of which are incorporated herein by reference in their entirety.

FIELD OF THE INVENTION

This invention relates to antibiotic peptides and peptide derivatives especially for use in medicine.

The invention further relates to compositions and methods for destroying microorganisms, such as bacteria or fungi, and methods of treating microbial infections. The invention further comprises a method for screening active substances.

BACKGROUND OF THE INVENTION

The occurrence of serious bacterial and fungal infections is an increasing problem despite notable progress in antibiotic therapy. Each year there are more than 40 million hospitalizations in the United States of America and more than 2 million of these patients become infected in the hospital. Antibiotic-resistant bacteria are involved in 50-60% of these cases (Tomasz A. Multiple-Antibiotic-Resistant Pathogenic Bacteria—A Report on the Rockefeller-University Workshop. *New England Journal of Medicine* 330: 1247-51, 1994). These hospital-acquired diseases are estimated to lead to 60 000 to 70 000 deaths in the USA and up to 10 000 deaths in Germany (Wenzel R P. The Mortality of Hospital-Acquired Blood-Stream Infections—Need for A New Vital Statistic. *International Journal of Epidemiology* 17: 225-7, 1988). Whereas resistant Gram-negative bacteria were the main problem in the 1970s, in the last decade there has been an increase in cases in which Gram-positive bacteria that are resistant to several antibiotics play a role (Moellering R C. Emerging resistance with gram-positive aerobic infections: Where do we go from here? Introduction: Problems with antimicrobial resistance in gram-positive cocci. *Clinical Infectious Diseases* 26: 1177-8, 1998). The current rapid development of resistant strains involves both Gram-positive and Gram-negative pathogens (Hand W L. Current challenges in antibiotic resistance. *Adolescent Medicine* 11: 427-38, 2000). Resistances developed first in species in which single mutations were sufficient to reach clinically important levels, e.g. *Staphylococcus aureus* and *Pseudomonas aeruginosa*; next were bacteria in which multiple mutations were necessary, for instance *E. coli* and *Neisseria gonorrhoeae*. This is due primarily to the frequent use of fluoroquinolone antibiotics (Hooper D C. Emerging mechanisms of fluoroquinolone resistance. *Emerging Infectious Diseases* 7: 337-41, 2001). Another important cause of the development of resistance in Gram-negative bacteria is the extensive range of lactamases in *Escherichia coli* and *Klebsiella pneumoniae* (Jones R N. Resistance patterns among nosocomial pathogens—*Trends over the past few years. Chest* 119: 397S-404S, 2001). Nearly half the clinically relevant strains of *Haemophilus ducreyi*, the causative agent of soft chancre, carry genes that make this bacterium resistant to amoxicillin, ampicillin and several other β-lactams (Prachayasittikul V, Lawung R, & Bulow L. Episome profiles and mobilizable beta-lactamase plasmid in *Haemophilus ducreyi*. Southeast Asian *J Trop Med Public Health* 31: 80-4, 2000). Similarly, the resistance of *Salmonella enterica* serovar *typhimurium* to tetracyclines rose from zero percent in the year 1948 to 98% in the year 1998 (Teuber M. Spread of antibiotic resistance with food-borne pathogens. *Cellular and Molecular Life Sciences* 56: 755-63, 1999).

This explains the need for further searching for new antibiotics. Inducible antibacterial peptides represent a field of research in which modern biochemistry, immunology and research into active substances come together. Peptide antibiotics, ranging in size from 13 to more than a hundred amino acids, have been isolated from plants, animals and microbes (Boman H G. Peptide Antibiotics and Their Role in Innate Immunity. *Annual Review of Immunology* 13: 61-92, 1995). A single animal has approx. 6-10 peptide antibiotics, with each peptide often displaying a completely different activity spectrum (Barra D, Simmaco M, & Boman H G. Gene-encoded peptide; antibiotics and innate immunity. Do 'animalcules' have defense budgets? *Febs Letters* 430: 130-4, 1998). It is known that the overwhelming number of antibacterial peptides, including the much-studied defensins, cecropins and magainins, act by a "lytic/ionic" mechanism. A permeabilizing effect on the bacterial cytoplasmic membrane has been discussed as a common mechanism of action of these "lytic" peptides (Ludtke S, He K, & Huang H. Membrane thinning caused by magainin 2. *Biochemistry* 34: 16764-9, 1995; Wimley W C, Selsted M E, & White S H. Interactions Between Human Defensins and Lipid Bilayers—Evidence for Formation of Multimeric Pores. *Protein Science* 3: 1362-73, 1994; Shai Y. Molecular Recognition Between Membrane-Spanning Polypeptides. *Trends in Biochemical Sciences* 20: 460-4, 1995). A cationic, amphipathic structure, which forms hydrophilic ion (proton) channels in a lipid bilayer, is the basis of this activity. Owing to the outflow of protons, the membrane potential that is necessary for many fundamental life processes is disturbed and as a result the cell is killed. Since disturbance of the membrane by these peptides is dependent on the recognition of chiral molecules, an amino acid exchange, which does not remove the general amphipathic structure or basic net charge, is tolerated functionally (Wade D et al. All-D Amino Acid-Containing Channel-Forming Antibiotic Peptides. *Proceedings of the National Academy of Sciences of the United States of America* 87: 4761-5, 1990; Steiner H, Andreu D, & Merrifield R B. Binding and Action of Cecropin and Cecropin Analogs—Antibacterial Peptides from Insects. *Biochimica et Biophysica Acta* 939: 260-6, 1988). At higher concentrations these lytic peptides often have toxic action on mammalian membranes, which limits their suitability as possible medicinal products. If proline is inserted into the sequence of the α-helical antimicrobial peptides, the capacity of the peptides to permeabilize the cytoplasmic membrane of *E. coli* decreases as a function of the number of proline residues. On examining this, it is amazing that some of the most active, native antibacterial peptides, at least with respect to some Gram-negative pathogens, belong to the family of proline-rich peptides (Otvos L et al. Insect peptides with improved protease-resistance protect mice against bacterial infection. *Protein Science* 9: 742-9, 2000).

The side effects described above are overcome by antimicrobial peptides (AMP), which specifically recognize a bacterial protein or other intra- or extracellular components, without displaying cross-reactivity with mammalian analogs.

This seems to apply to proline-rich antimicrobial peptides, including apidaecins, drosocin and pyrrhocoricin which were originally isolated from insects. With the enormous variation in size and biochemical properties, it is not surprising that the structure-activity and conformation-activity relations are the focus of antibacterial peptide research. A complete investigation of the natural antibacterial peptide repertoire for biological strength is important not only for general biochemical questions, but is also of constant interest for the pharmaceutical industry. Despite the problems of in-vitro tests with peptide-based antibiotics, some natural, cationic antibacterial peptides have already reached the clinical trial phase (Boman H G. Peptide Antibiotics and Their Role in Innate Immunity. *Annual Review of Immunology* 13: 61-92, 1995). Whereas some of these peptides showed activity as topical (local) agents in the early clinical trial phase, others were active in systemic therapy. For example, the cationic protein rBPI 21, which is used for parental treatment of meningococcemia, has completed the third phase of clinical testing (Boman H G. Peptide Antibiotics and Their Role in Innate Immunity. *Annual Review of Immunology* 13: 61-92, 1995).

The family of the proline-rich peptides (e.g. apidaecin, drosocin and pyrrhocoricin) kill bacteria not only by permeabilization of their membrane, but bind stereospecifically to one or more target proteins. These possible interaction partners, up to now the heat-shock protein DnaK has been investigated thoroughly (Kragol G et al. Identification of crucial residues for the antibacterial activity of the proline-rich peptide, pyrrhocoricin. *European Journal of Biochemistry* 269: 4226-37, 2002; Kragol G et al. The antibacterial peptide pyrrhocoricin inhibits the ATPase actions of DnaK and prevents chaperone-assisted protein folding. *Biochemistry* 40: 3016-26, 2001), are inhibited by the proline-rich peptides and presumably the correct protein folding is prevented, ultimately leading to cell death. Moreover, proline-rich peptides, in stark contrast to AMPs with defined secondary structure such as melittin or gramicidin, seem in vitro to have neither hemolytic nor toxic effects on eukaryotic cells. Along with antimicrobial activity, mainly the stability in mammalian serum (25%) has a decisive influence on the development of new peptide-based antibiotics. For example, drosocin is broken down within an hour, whereas pyrrhocoricin is far more stable with respect to proteases, with half-lives of 120 minutes.

In biological experiments by Schneider and Dorn (2001) (Schneider M & Dorn A. Differential infectivity of two pseudomonas species and the immune response in the milkweed bug, *Oncopeltus fasciatus* (Insecta: Hemiptera). *Journal of Invertebrate Pathology* 78: 135-40, 2001), nymphs and pupae of the milkweed bug *Oncopeltus fasciatus* from the Lygaeidae family were infected with two different Gram-negative *Pseudomonas* species and their immune response was analyzed. Whereas infection of the nymphs of *O. fasciatus* with the human pathogen *Pseudomonas aeruginosa* resulted in the death of all individuals after 48 h, 71% of individuals infected with the less pathogenic *Pseudomonas putida* survived for at least 96 h. If the nymphs of the milkweed bug were then infected first with *P. putida* and after 24 h with *P. aeruginosa*, the survival rate of the doubly infected individuals within the first 24 h rose significantly to 73%. The probable induction of synthesis of antibacterial peptides, by which insects defend themselves, within the scope of their innate immune system, against invading microorganisms, was then investigated. Four peptides (Oncopeltus antibacterial peptide 1-4) were identified with molecular weights of 15, 8, 5 or 2 kDa and were held to be responsible for the antibacterial action. Sequence analysis according to Edman found, in addition to a 34 amino acid long partial sequence for peptide 1 (15 kDa), also the incomplete sequence of the proline-rich 2 kDa peptide 4. The amino acids in positions 11 and the C-terminal sequence starting from position 19 could not be identified definitively. The exact molecular weight is unknown.

A selection of currently known sequences of antibiotic peptides is presented in Table 1:

TABLE 1

| Peptide | Species | Sequence | SEQ ID NO. | Ref. |
|---|---|---|---|---|
| Apidaecin 1a | Apis mellifera | GNNRPVYIPQPRPPHPRI | 119 | [1] |
| Apidaecin 1b | Apis mellifera | GNNRPVYIPQPRPPHPRL | 87 | [1] |
| Drosocin | Drosophila melanogaster | GKPRPYSPRPTSHPRPIRV | 89 | [2] |
| Formaecin 1 | Myrmecia gulosa | GRPNPVNNKPTPYPHL | 120 | [3] |
| Pyrrhocoricin | Pyrrhocoris apterus | VDKGSYLPRPTPPRPIYNRN-NH$_2$ | 91 | [4] |
| Metalnikowin 1 | Palomena prasina | VDKPDYRPRPRPPNM | 121 | [5] |
| Oncopeltus antibacterial peptide 1 | Oncopeltus fasciatus | EVSLKGEGGSNKGFIQGSGTKTLFQDDKTKLDGT | 122 | [6] |

TABLE 1-continued

| Peptide | Species | Sequence | SEQ ID NO. | Ref. |
|---|---|---|---|---|
| Oncopeltus antibacterial peptide 4 | Oncopeltus fasciatus | VDKPPYLPRP(X/P)PPRRIYN(NR) | 123 | [6] |

[1] Casteels P, Ampe C, Jacobs F, Vaeck M, & Tempst P. Apidaecins - Antibacterial Peptides from Honeybees. *Embo Journal* 8: 2387-91, 1989
[2] Bulet P et al. A Novel Inducible Antibacterial Peptide of *Drosophila* Carries an O-Glycosylated Substitution. *Journal of Biological Chemistry* 268: 14893-7, 1993
[3] Mackintosh J A et al. Isolation from an ant *Myrmecia gulosa* of two inducible O-glycosylated proline-rich antibacterial peptides. *Journal of Biological Chemistry* 273: 6139-41, 1998
[4] Cociancich S et al. Novel Inducible Antibacterial Peptides from A Hemipteran Insect, the Sap-Sucking Bug *Pyrrhocoris-Apterus*. *Biochemical Journal* 300: 567-75, 1994
[5] Chernysh S, Cociancich S, Briand J P, Hetru C, & Bulet P. The inducible antibacterial peptides of the hemipteran insect *Palomena prasina*: Identification of a unique family of proline-rich peptides and of a novel insect defensin. *Journal of Insect Physiology* 42: 81-9, 1996
[6] Schneider M & Dorn A. Differential infectivity of two pseudomonas species and the immune response in the milkweed bug, *Oncopeltus fasciatus* (Insecta: Hemiptera). *Journal of Invertebrate Pathology* 78: 135-40, 2001

There is still a demand for new antibacterial and antimycotic compounds, new antibacterial and antimycotic pharmaceutical compositions, as well as methods using them, and compounds that can be used for screening active substances, to detect new pharmaceutical antibiotics.

The problem to be solved by the present invention is to provide new antibiotic peptides with increased stability, to extend the spectrum of action of the AMPs on Gram-positive bacteria and thus make modern broad-spectrum antibiotics available, and to introduce the peptides into eukaryotic cells and thus combat hidden bacteria.

DESCRIPTION OF THE INVENTION

The problem is solved by the peptides and peptide derivatives according to the invention with the general formula:

$$Sub_1-X_1-D_2-K_3-P_4-P_5-Y_6-L_7-P_8-R_9-P_{10}-X_2-P_{12}-P_{13}-R_{14}-X_3-I_{16}-P_{17}/Y_{17}-N_{18}-N_{19}-X_4-Sub_2$$
(Formula 1)

$X_1$ is a residue with a nonpolar, hydrophobic side chain or with a positive net charge or a side chain that is positively charged under physiological conditions;

$D_2$ is an aspartic acid or glutamic acid residue, $K_3$ is a residue with a positive net charge or a side chain that is positively charged under physiological conditions, preferably lysine or arginine, $X_2$ and $X_4$ are selected independently of one another from residues with a positive net charge or a side chain that is positively charged under physiological conditions;

$X_3$ is a residue with a positive net charge or a side chain that is positively charged under physiological conditions or proline or a proline derivative;

$L_7$ and $I_{16}$ are selected independently of one another from residues with a nonpolar, hydrophobic side chain, preferably leucine, isoleucine and valine, $Y_6$ and $Y_{17}$ are in each case tyrosine, $R_9$ and $R_{14}$ are in each case arginine, $N_{18}$ is asparagine or glutamine, $N_{19}$ is asparagine or glutamine or is absent, $P_4$, $P_5$, $P_8$, $P_{10}$, $P_{12}$, $P_{13}$ and $P_{17}$ are selected independently of one another from proline and proline derivatives or hydroxyproline and hydroxyproline derivatives, wherein optionally $P_{13}$ and $R_{14}$ are exchanged, and/or optionally one or two of the residues selected from $D_2$, $P_4$, $P_5$, $P_8$, $P_{10}$, $P_{12}$, $P_{13}$, $P_{17}$ and $Y_{17}$ are replaced with any residue, $Sub_1$ is the free N-terminus of the amino acid $X_1$ or a modified N-terminal amino group;

$Sub_2$ is the free C-terminal carboxyl group of the C-terminal amino acid (—COOH) or a modified C-terminal carboxyl group.

In an especially preferred embodiment $I_{16}$ is selected from the group comprising leucine, isoleucine, tert-butylglycine and valine.

In one embodiment $N_{19}$ is absent when $P_{17}$ is present.

Peptides and peptide derivatives with one of the general formulas 1 to 3 are preferred:

$$Sub_1-X_1-D_2-K_3-P_4-P_5-Y_6-L_7-P_8-R_9-P_{10}-X_2-P_{12}-P_{13}-R_{14}-X_3-I_{16}-Y_{17}-N_{18}-X_4-Sub_2$$
(Formula 2)

$$Sub_1-X_1-D_2-K_3-P_4-P_5-Y_6-L_7-P_8-R_9-P_{10}-X_2-P_{12}-P_{13}-R_{14}-X_3-I_{16}-Y_{17}-N_{18}-N_{19}-X_4-Sub_2$$
(Formula 3)

$$Sub_1-X_1-D_2-K_3-P_4-P_5-Y_6-L_7-P_8-R_9-P_{10}-X_2-P_{12}-P_{13}-R_{14}-X_3-I_{16}-P_{17}-N_{18}-X_4-Sub_2$$
(Formula 4)

$X_1$ is a residue with a nonpolar, hydrophobic side chain or with a positive net charge or a side chain that is positively charged under physiological conditions;

$D_2$ is an aspartic acid or glutamic acid residue, $K_3$ is a residue with a positive net charge or a side chain that is positively charged under physiological conditions, preferably lysine or arginine, $X_2$ and $X_4$ are selected independently of one another from residues with a positive net charge or a side chain that is positively charged under physiological conditions;

$X_3$ is a residue with a positive net charge or a side chain that is positively charged under physiological conditions or proline or a proline derivative;

$L_7$ and $I_{16}$ are selected independently of one another from residues with a nonpolar, hydrophobic side chain, preferably leucine, isoleucine and valine.

In an especially preferred embodiment $I_{16}$ is selected from the group comprising leucine, isoleucine, tert-butylglycine and valine.

$Y_6$ and $Y_{17}$ are in each case tyrosine, $R_9$ and $R_{14}$ are in each case arginine, $N_{18}$ and $N_{19}$ are in each case asparagine or glutamine, $P_4$, $P_5$, $P_8$, $P_{10}$, $P_{12}$, $P_{13}$ and $P_{17}$ are selected independently of one another from proline and proline derivatives or hydroxyproline and hydroxyproline derivatives.

Optionally one or two of the residues selected from $D_2$, $P_4$, $P_5$, $P_8$, $P_{10}$, $P_{12}$, $P_{13}$, $P_{17}$ and $Y_{17}$ are replaced with any amino acid residue, preferably a neutral residue, especially preferably a neutral polar residue.

Moreover, $P_{13}$ and $R_{14}$ are optionally exchanged.

Residues with a positive net charge or a side chain that is positively charged under physiological conditions are preferably selected from the group comprising arginine, lysine, δ-hydroxylysine, homoarginine, 2,4-diaminobutyric acid, β-homoarginine, D-arginine, arginal (—COOH in arginine is replaced with —CHO), 2-amino-3-guanidinopropionic acid, nitroarginine (preferably N(G)-nitroarginine), nitrosoarginine (preferably N(G)-nitrosoarginine), methylarginine (preferably N-methyl-arginine), ε-N-methyllysine, allo-hydroxylysine, 2,3-diaminopropionic acid, 2,2'-diaminopimelic acid, ornithine, sym-dimethylarginine, asym-dimethylarginine, 2,6-diaminohexinic acid, p-aminobenzoic acid and 3-aminotyrosine and less preferably histidine, 1-methylhistidine and 3-methylhistidine. $X_1$, $X_2$ and $X_3$ are preferably selected independently of one another from this list.

The term proline derivative stands for an amino acid residue derived from proline, which is obtained from proline preferably by structural modification of a functional group. Preferred proline derivatives are selected from the group comprising β-cyclohexylalanine, 3,4-cis-methanoproline, 3,4-dehydroproline, homoproline or pseudoproline. The term hydroxyproline includes inter alia cis-4-hydroxyproline, trans-4-hydroxyproline, cis-3-hydroxyproline and trans-3-hydroxyproline. The term hydroxyproline derivative stands correspondingly for an amino acid residue derived from hydroxyproline, which is obtained from hydroxyproline preferably by structural modification of a functional group. Preferred hydroxyproline derivatives are selected from hydroxy-β-cyclohexylalanine and the aforementioned proline derivatives, which are substituted with a hydroxyl group.

A neutral residue is a residue with a side chain that is uncharged under physiological conditions.

A polar residue preferably has at least one polar group in the side chain. These are preferably selected from the group comprising hydroxyl, sulfhydryl, amine, amide or ester groups or other groups that permit the formation of hydrogen bridges.

Preferred neutral polar residues are selected from the group comprising asparagine, cysteine, glutamine, serine, threonine, tyrosine, citrulline, N-methylserine, homoserine, allo-threonine and 3,5-dinitrotyrosine and β-homoserine.

In a preferred embodiment $P_5$ is selected from the group comprising β-cyclohexylalanine, 3,4-cis-methanoproline, 3,4-dehydroproline, homoproline or pseudoproline, cis-4-hydroxyproline, cis-3-hydroxyproline, trans-3-hydroxyproline, asparagine, cysteine, glutamine, serine, threonine, tyrosine, citrulline, N-methylserine, homoserine, allo-threonine and 3,5-dinitrotyrosine and β-homoserine.

The residues with a nonpolar, hydrophobic side chain are uncharged residues under physiological conditions, preferably with a hydropathy index above 0, especially preferably above 3. Preferred nonpolar, hydrophobic side chains are selected from the group comprising alkyl, alkylene, alkoxy, alkenoxy, alkylsulfanyl and alkenylsulfanyl residues with 1 to 10, preferably 2 to 6 carbon atoms, or aryl residues with 5 to 12 carbon atoms. Preferred residues with a nonpolar, hydrophobic side chain are selected from leucine, isoleucine, valine, methionine, alanine, phenylalanine, N-methylleucine, tert-butylglycine, cyclohexylalanine, β-alanine, 1-aminocyclohexylcarboxylic acid, N-methylisoleucine, norleucine, norvaline and N-methylvaline.

"Physiological conditions" means a pH from pH 6 to 8 and a temperature from 30° C. to 40° C., preferably a temperature of 37° C., a pH of 7.4 and an osmotic pressure of 300 mosmol/kg.

The peptides or peptide derivatives according to the invention preferably contain at least 19 amino acid residues, preferably up to 50 amino acid residues.

$Sub_1$ is the free N-terminus of the amino acid $X_1$ or a modified N-terminal amino group. $Sub_2$ is the free C-terminal carboxyl group of the C-terminal amino acid (—COOH) or a modified C-terminal carboxyl group. "Modified N-terminal amino group" and "modified C-terminal carboxyl group" mean that the amino group or carboxyl group is altered (e.g. reduced or substituted).

$Sub_1$ therefore represents the free N-terminus of the amino acid $X_1$ or a modification of the N-terminal amino group (which replaces the N-terminal amino group of the amino acid $X_1$ with $Sub_1$) with the general formula $NR_1R_2$. $Sub_1=NR_1R_2$, wherein $R_1$ and $R_2$ are independent of one another and are preferably selected from hydrogen or from the following groups:

(i) a linear, branched, cyclic or heterocyclic alkyl group, for example methyl, ethyl, n-propyl, isopropyl, n-butyl, isobutyl or cyclohexyl;

(ii) a linear, branched, cyclic or heterocyclic alkanoyl group, for example acetyl or methanoyl (formyl), propionyl, n-butyryl, isobutyryl, pentanoyl, hexanoyl or cyclohexanoyl;

(iii) a reporter group, preferably a fluorescent dye (for example fluorescein, Alexa488) or biotin;

(iv) together with $COR_3$ (see below) a linker between N- and C-terminus to obtain a cyclic peptide, e.g. based on guanidine, ethylene glycol oligomers, 2,4-diaminobutyric acid, 2,3-diaminopropionic acid, 2,2'-diaminopimelic acid, desmosinee or isodesmosinees.

(v) a linker for coupling a further peptide or peptide derivative ($Y_1$) by means of a specific chemical or enzymatic reaction, e.g. based on iodo-, bromo- or chloroalkanoic acids (e.g. iodoacetic acid) or maleimide for coupling to a thiol-containing peptide or also another reactive group (e.g. amino group, thiol group) for coupling a second peptide or peptide derivative (e.g. as active ester, aldehyde or thioester) as carrier protein.

(vi) a linker as stated in (v), to which another peptide or peptide derivative $Y_1$ is coupled.

Examples of N-terminal modifications are acetylated, formylated or guanylated N-termini.

Preferably another peptide or peptide derivative $Y_1$ is coupled via $Sub_1$. $Y_1$ is preferably a biopolymer (e.g. peptide), which introduces the antimicrobial peptide according to any one of the formulas 1 to 4 into bacteria and therefore increases the activity of the antimicrobial peptide against this bacterium and/or introduces it into mammalian cells and therefore makes it possible to treat bacteria that are concealed in mammalian cells. $Y_1$ is coupled via $Sub_1$ to $X_1$ of the peptide either permanently (e.g. peptide or amidine bond for $Sub_1=NH_2$ or thioether for $Sub_1=SH$, iodoacetate or maleimide) or by a compound that is cleavable under certain conditions (for example disulfide bridges or acid-labile linkers). Preferred sequences for $Y_1$ are cell-penetrating peptides (CPP), for example penetratin, Tat peptides, model amphipathic peptides and transportans (Langel, U. in *Handbook of Cell-Penetrating Peptides* 5-28 (CRC—Taylor & Francis Group, 2006).

A linker is a designation for molecules or groups of molecules that are employed for coupling two substances; preferred linkers contain two reactive groups (for example iodoacetate, maleimide, imido- or NHs-ester or hydrazide), which are joined by a bridging molecule (e.g. polyethylene glycol) preferably with 10 to 20 carbon atoms.

$Sub_2$ is the free C-terminal carboxyl group of the C-terminal amino acid (—COOH) or a modified C-terminal carboxyl group, preferably with the general formula $COR_3$ ($R_3$ replaces the hydroxyl group of the last amino acid), $X_5$-$COR_3$ or $X_6$-$COR_3$ or $X_5X_6$-$COR_3$.

$COR_3$ is preferably selected from the following group:
(i) carboxyl ($R_3$ is a free hydroxyl group), an ester ($R_3$ is an alkoxy group), an amide ($R_3$ is an amine) or an imide;
(ii) a linker, which together with $Sub_1$ bridges the N- and C-termini to a cyclic peptide;
(iii) $COR_3$, in which $R_3$ is either an additional amino acid residue, which is selected from the group comprising Pro, Ile, Leu, Arg and Gln, or in which $R_3$ is a peptide, preferably with two to six amino acids, of which at least one amino acid is selected from the group comprising Pro, Ile, Leu, Arg or Gln, wherein the latter is substituted with a member from the group with carboxyl ($R_3$ is a free hydroxyl group), an ester ($R_3$ is an alcohol, such as methanol, ethanol, propanol, iso-propanol or butanol), an amide ($R_3$ is an amide) or an imide ($R_3$ is an alkylamine or dialkylamine, such as methylamine, ethylamine, dimethylamine or cyclohexylamine).
(iv) $COR_3$ in which $R_3$ is an additional, branched amino acid, to form a dimeric or oligomeric structure, for example lysine, hydroxylysine, ornithine, 2,4-diaminobutyric acid, 2,3-diaminopropionic acid, 2,2'-diaminopimelic acid, desmosinee, isodesmosinee or a combination of these branched amino acids.
(v) a linker for coupling another peptide or peptide derivative ($Y_1$) by means of a specific chemical or enzymatic reaction, e.g. based on iodo-, bromo- or chloroalkanoic acids (e.g. iodoacetic acid) or maleimide, for coupling to a thiol-containing peptide or also another reactive group (e.g. amino group, thiol group) for, coupling a second peptide or peptide derivative (e.g. as active ester, aldehyde or thioester) as carrier protein.
(vi) a linker as stated in (v), onto which another peptide or peptide derivative $Y_1$ is coupled.

In this way, C-terminal peptide derivatives can be obtained, such as ester ($R_3$=alkoxy), amide ($R_3$=amine, e.g. —$NH_2$) or imide ($R_2$=alkylamine, e.g. —$NHC_3H_7$) or a peptide, which has been extended with further amino acids, which was selected from the group comprising Pro, Ile, Arg and Val, or once again are modified on the C-terminus as ester, amide or imide. Further peptide derivatives can be formed by modification of the N-terminal or C-terminal ends of the peptides. These changes can be for example an additional alkyl or alkanoyl group (either with a straight chain or branched, cyclic or heterocyclic) or an additional guanidino group or an additional macromolecule or a reporter residue, which is coupled either permanently or via a compound that is cleavable under certain conditions (such as disulfide bridges or acid labile linkers).

Modification of the C-terminus preferably takes place by thioester synthesis and subsequent substitution with primary amines.

All natural amino acids, unnatural amino acids or amino acid derivatives (for example imino acids), which form the peptides or peptide derivatives according to the invention, can be either in the L- or D-conformation. Unless specified otherwise, however, the building blocks in the sequences are preferably in the L-conformation.

$X_5$ and $X_6$ are optionally additional residues. In the case when $X_5$ and $X_6$ are absent, the last arginine (Arg) in the abovementioned sequence has a free C-terminal carboxyl group or is joined to $Sub_2$.

In the case when at least one residue $X_5$ and $X_6$ is present, the peptide has for example one of the following general formulas:

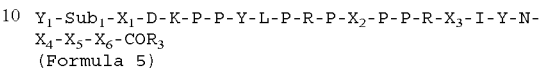

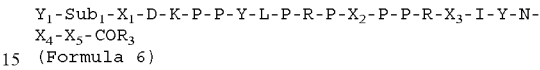

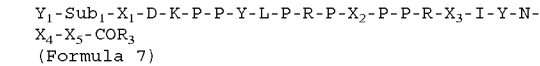

$X_5$ is selected from proline, proline derivatives or a neutral residue with a polar side chain (such as asparagine, glutamine). Preferred residues $X_5$ are selected from the groups comprising proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline, pseudoproline as well as asparagine, glutamine, citrulline, N-methylserine, N-methylglycine, dihydroxyphenylalanine, N-ethyl asparagine, N-ethylglycine, homoserine, penicillamine, tetrahydropyranylglycine, allo-threonine and 3,5-dinitrotyrosine.

$X_6$ is selected from proline, proline derivatives, a polar residue (such as serine) or a hydrophobic residue. Preferred residues $X_6$ are selected from the groups comprising proline, cis-4-hydroxyproline, trans-4-hydroxyproline, cis-3-hydroxyproline, trans-3-hydroxyproline, β-cyclohexylalanine, 3,4-cis-methanoproline, 3,4-dehydroproline, homoproline or pseudoproline, serine, threonine, δ-hydroxylysine, citrulline, homoserine or allo-threonine as well as phenylalanine, N-methylleucine, leucine, isoleucine, valine, methionine, tert-butylglycine, cyclohexylalanine, alanine, β-alanine, 1-animocyclohexylcarboxylic acid, N-methylisoleucine, norleucine, norvaline, N-methylvaline or it is a short peptide sequence preferably with one to three residues, which are preferably selected from proline, isoleucine or one of the residues mentioned above.

Alternatively $X_6$ is a branched linker, which contains several peptide units. This is formed by the residue of an amino acid that contains several amino groups, for example lysine, hydroxylysine, ornithine, 2,4-diaminobutyric acid, 2,3-diaminopropionic acid, 2,2'-diaminopimelic acid, desmosinee, isodesmosinee.

The C-terminal amino acid is for example $X_4$ in formulas 1 to 4, $X_5$ in formula 6 or $X_6$ in formulas 5 and 7.

The peptides and peptide derivatives according to the invention display, relative to the previously incompletely determined sequence of the proline-rich antimicrobial peptide "Oncopeltus antibacterial peptide 4", an improved antibacterial activity, a broader spectrum of action and increased protease resistance.

Preferred examples of the peptides and peptide derivatives according to the invention are selected from the sequences according to SEQ ID NO. 5 to 9, 14 to 26, 29, 30, 32, 33, 36, 38, 40, 41, 44 to 46, 49, 50, 53 to 59, 61 to 85, 93, 94, 101, 102, 107 to 112; cf. Table 2 in example 1).

The especially preferred peptide with the sequence VDK-PPYLPRPRPPRRIYNR-$NH_2$ (SEQ ID NO. 18) is called oncocin hereinafter. Other peptides and peptide derivatives according to the invention are called oncocin derivatives hereinafter.

The peptides and/or multimeric peptide constructs according to the invention, which were modified to increase the antimicrobial or antimycotic activity and to extend the spectrum of activity to other bacteria or fungi and to improve the stability, are characterized by their high antibacterial and/or antimycotic efficacy and by good metabolic stability in mammalian serum.

Suitable modifications in positions 11 ($X_2$), 15 ($X_3$) and 19 ($X_4$) improve the antibacterial activity of the native Oncopeltus 4-sequence against various bacteria, as is discussed below and is shown in the examples.

Furthermore, the residues $Sub_1$-$X_1$, $X_3$ and $X_4$ can additionally stabilize the N- and C-terminal peptide sequences against proteolytic degradation and thus increase the half-life in serum.

The sequences according to the invention have a positively charged residue $X_2$ (position 11).

Preferred examples according to the invention are sequences with a positively charged residue $X_3$ (position 15), for example the sequences selected from the sequences according to SEQ ID NO. 18, 29, 32, 33, 46, 50, 54 to 59, 62, to 74, 78, 79, 82, 107, 109, 111 and 112 or with hydroxyproline as residue $X_3$ (position 15), for example the sequences selected from the sequences according to SEQ ID NO. 25 and 63.

The sequences according to the invention have positively charged residue $X_4$ (position 19).

Furthermore, the C-terminal carboxyl group is preferably modified. Surprisingly, this leads to an increased half-life of the peptides in serum.

The modifications of the N- and C-termini permit coupling of the peptides to other groups, such as for example other amino acid sequences (possibly creating multimeric peptides or proteins) or other biomolecules, which have the function of a carrier or label, for example of $Y_1$ via $Sub_1$. In a special embodiment the carrier molecule functions as a shuttle in order to combat bacterial infection in mammalian cells or transport the antibacterial peptide and peptide derivative into bacteria, into which the antibacterial peptide cannot penetrate on its own (e.g. Gram-positive bacteria). Examples of said cell-penetrating peptides (CPP) are for example penetratins, Tat peptides, model amphipathic peptides and transportans. Moreover, the site of infection can be recognized by the coupled structure (target molecule) and as a result the antibiotic substance is brought near the (bacterial) cell, in order to combat it. These target molecules are for example molecules that are known to bind to lipopolysaccharide (LPS) molecules, which form the outside of the Gram-negative bacteria. Known compounds for this application are for example anchor peptides, such as the AcmA motif from *Lactobacillus* or an antibody directed against lipopolysaccharide. This last-mentioned variant is preferred, as it also has an intrinsic antibiotic effect and can therefore be used for increasing the activity of the peptides according to the invention.

It is advantageous if the N-terminal amino acid, i.e. $Sub_1$-$X_1$, has a residue that is positively charged in physiological conditions, i.e. in the human body.

An example for achieving N-terminal stabilization is acylation ($Sub_1$=acyl-NH—), for example acetylation ($Sub_1$=acetyl-NH—), of the α-amino group of a positively charged amino acid, such as ornithine or lysine ($Sub_1$-$X_1$=acyl-Orn or acyl-Lys). This acylation (preferably acetylation) leaves the positive charge in the side chain of the amino acid intact.

Further preferred examples of the invention are sequences with positively charged residues on $X_2$, $X_3$ and $X_4$ (position 11, 15 and 19), for example the sequences that are selected from the sequences according to SEQ ID NO. 18, 22, 58, 62, 63, 65 to 74, 78, 79, 82 and 83.

Further preferred examples of the invention are sequences with hydroxyproline instead of proline, for example the sequences selected from the sequences according to SEQ ID NO. 21, 22 and 24.

Especially preferred examples are peptides that bear a positively charged amino acid in positions 11, 15 and 19 ($X_2$, $X_3$ and $X_4$) (such as ornithine, arginine or lysine) and have a modified C-terminus, in particular the peptides according to SEQ ID NO. 18, 63, 71, 72, 74.

An especially preferred peptide contains ornithine in position 15 (residue $X_3$), arginine in positions 11 and 19 (residues $X_2$ and $X_4$) and the C-terminus as propylamide (residue $Sub_2$) according to SEQ ID NO. 71.

Another especially preferred peptide contains ornithine in position 15 and 19 (residue $X_3$ and $X_4$ and arginine in position 11 (residue $X_2$) the C-terminus as amide (residue $Sub_2$). A preferred peptide of this kind has the sequence according to SEQ ID NO. 72.

Another especially preferred peptide contains arginine in position 11 (residue $X_2$), trans-4-hydroxyproline in position 15 (residue $X_3$) and ornithine in position 19 (residue $X_4$) and the C-terminus as amide (residue $Sub_2$). A preferred peptide of this kind has the sequence according to SEQ ID NO. 63.

Another especially preferred peptide contains ornithine in position 15 and 19 (residue $X_3$ and $X_4$, arginine in position 11 (residues $X_2$), in position 18 glutamine instead of asparagine and the C-terminus as amide (residue $Sub_2$). A preferred peptide of this kind has the sequence according to SEQ ID NO. 74.

It can be seen from the examples that the modifications of the C-terminus according to the invention to an amide (Sub=—NH$_2$), surprisingly, significantly increase the antibiotic action against *E. coli* and *M. luteus*. Preferred sequences with an amide on the C-terminus are SEQ ID NO. 18, 22, 50, 54 to 57, 61 to 63, 65 to 70, 72 to 79 and 82.

Modifications which reduce C-terminal degradation are also preferred, for example isopropylamide on the C-terminus ($Sub_2$) according to SEQ ID NO. 58 and 71 and trans-4-hydroxyproline at position(s) 8 and/or 13. The experimental results show that apparently the amino acids at position 6 and 7 are also very important for the antibiotic action. Thus, exchange of individual amino acids at these positions 6 and/or 7 with alanine destroys the efficacy in comparison with the antibiotic activity of the oncocin.

The most preferred examples of the invention are peptides, which offer the following advantages:

(i) an increased half-life in mammalian serum and
(ii) an increased antimicrobial activity against one or more bacterial strains, especially human pathogens, or fungi or other microbial infections and
(iii) the peptides are not toxic to human cells, including erythrocytes.

The action of antimicrobial peptides is very complex, as they must pass through the cell membrane and penetrate into the cytoplasm, in order to inhibit a special intracellular bacterial target molecule, but without having a toxic effect on mammalian cells and blood cells. Another important point is stability of the peptides or peptide derivatives against degradation by peptidases or proteases. Therefore the ideal peptide has a high antibacterial activity (low MIC values), no cellular toxicity, no hemolytic activity and a half-life of several hours in blood. Compared with the native Oncopeltus 4-sequence, the peptide derivatives according to the invention display a more than twenty times higher antimicrobial activity. The C-terminus is preferably modified (amide, alkylamide, ester) and the C-terminal region after position 14 is for example altered by substitution of positions 15 and/or 19 ($X_3$ and $X_4$) with nonproteinogenic amino acids. At the N-terminus, a positive charge is preferred, to achieve good activity. The valine in position 1 ($X_1$) of the native Oncopeltus 4-sequence is preferably free or replaced with an acetylated basic residue such as arginine, lysine or ornithine. Ornithine is especially preferred, which surprisingly leads to increased protein stability. For the same reason positions 15 and 19 of the Oncopeltus 4-sequence are preferably substituted, which surprisingly leads to increased peptide stability. Examples are the exchange of positions 15 and 19 ($X_3$ and $X_4$) for trans-4-hydroxyproline ($X_3$) and ornithine ($X_4$) or both for ornithine, which unexpectedly increases the half-life in 25% serum by more than a factor of 10, i.e. from less than 30 min to more than 6 h. The transfer of the C-terminus from the free acid to a propylamide also leads to an increase in serum stability.

Preferably a cell-penetrating peptide sequence is coupled to the peptides and peptide derivatives according to the invention. This coupling preferably takes place via a linker, for example an acetyl group or an alkyl group. The coupling preferably takes place on the N-terminus of the peptide and peptide derivative according to the invention. Preferably, for this the proline-rich peptide or peptide derivative is derivativized at the N-terminal with iodoacetate and the cell-penetrating peptide sequence is lengthened at the C-terminal by a cysteine residue. The thiol group of this cysteine then forms a thioether bridge with the acetyl group.

Cell-penetrating peptides (CPP) are relatively short polycationic or hydrophobic peptides, attachment of which makes it possible for prokaryotic and eukaryotic cells to pass through the cell membrane. CPPs can have different sequences and lengths. In most cases, however, they contain a sequence of approx. 10 to 40 amino acids and are rich in positively charged amino acids (e.g. Arg, Lys). These short sequences are responsible for passage through the cell membrane and are called "protein transduction domains (PTDs)".

Preferred cell-penetrating peptides are selected from penetratin, Tat peptides, model amphipathic peptides, transportan (derived from galanin), SynB (derived from protegrin) and cis-γ-amino-1-proline-containing peptides.

The cell-penetrating peptide sequences used according to the invention are preferably 8 to 20 amino acid residues long, wherein 30% to 90% of the residues have side chains that are positively charged under physiological conditions. The remaining residues are preferably neutral. Preferred cell-penetrating peptide sequences are selected from:

```
RQIKIWFQNRRMKWKK-OH           SEQ ID NO. 105
(a penetratin),

KLALKLALKALKAALKLA-NH2        SEQ ID NO. 124
(model amphipathic peptide)

RKKRRQRRR                     SEQ ID NO. 125
(a Tat peptide).
```

Further preferred cell-penetrating peptide sequences are given in the literature (Langel, U. in *Handbook of Cell-Penetrating Peptides* 5-28 (CRC—Taylor & Francis Group, 2006), (Pujals S, Giralt E. Proline-rich, amphipathic cell-penetrating peptides *Adv Drug Deliv Rev.* 60(4-5): 473-84, 2008) and (Farrera-Sinfreu J, Giralt E, Royo M, Albericio F. Cell-penetrating proline-rich peptidomimetics. *Methods Mol Biol.* 386: 241-67, 2007), which in this connection are incorporated as references.

In preferred examples of said peptide derivatives, the AMPs were lengthened N-terminally before position 1 ($X_1$) by penetratin-cysteine ($Y_1$) via iodoacetyl ($Sub_1$) with formation of a thioether bond. Preferred examples of this kind are preferably selected from the sequences according to SEQ ID NO. 101 and 102.

Through the attachment of a cell-penetrating peptide sequence, such as penetratin, surprisingly the activity against Gram-negative and Gram-positive bacteria is increased and the spectrum of action is extended to other Gram-positive and Gram-negative bacteria and additionally the antimicrobial peptides will be introduced into mammalian cells without being cytotoxic, so that hidden bacteria, fungi or viruses can also be reached in these cells.

Penetratin corresponds to the partial sequence R43 to K58 of the Antennapedia homeodomain (DNA-binding region of a transcription factor), of the fruit fly *Drosophila melanogaster*. The sequence of penetratin (preferably R Q I K I W F Q N R R M K W K K-OH; SEQ ID NO. 105) is rich in cationic amino acids and in that resembles the sequences of many AMPs.

In this invention the cell-penetrating peptide sequence is utilized for introducing AMPs both into bacteria and mammalian cells. Coupled to penetratin, the AMPs are transported into eukaryotic cells, also for treating infections there. In addition, toxic effects can be investigated by interaction of the AMPs with intracellular target molecules.

The coupling of penetratin to the antimicrobial peptides according to the invention via a thioether bridge forms part of the invention.

For this, the C-terminus of penetratin was extended by a cysteine and was coupled to the antimicrobial peptide, labeled N-terminally with iodoacetic acid.

As well as oncocin and its derivatives, according to the invention other antimicrobial peptides, preferably proline-rich peptides or peptide derivatives, for example apidaecin, drosocin, formaecin 1, pyrrhocoricin and metalnikowin 1, can also be modified correspondingly with a cell-penetrating peptide sequence, for example penetratin.

Preferred apidaecin derivatives are mentioned in PCT/EP2008/059512 (filed on Jul. 21, 2008), which in this connection is incorporated as reference.

Preferred examples of said peptide derivatives are selected from the sequences according to SEQ ID NO. 95 to 100 and 106.

The expression "peptide", as used here, stands for a sequence of amino acids that are linked via a peptide bond, wherein the amino acids are preferably selected from the twenty naturally occurring peptide-forming amino acids and in which the amino acids can be in the L-configuration or D-configuration, or in the case of isoleucine and threonine also in the D-allo-configuration (only inversion of one of the two chiral centers).

The expression peptide derivative (or peptidomimetic) used in the description of the invention comprises not only peptides that are modified with $Y_1$, $Sub_1$ and $Sub_2$ on the N- or C-terminus, as described above. In addition it comprises peptides that have been altered by substitutions and/or modifications of one or more amino acid residues by chemical groups, wherein said chemical groups are different from the natural protein-forming amino acid residues, for example nonproteinogenic α-amino acids, β-amino acids or peptides with an altered backbone. The term "altered backbone" means that at least one peptide bond has been modified chemically, i.e. has been replaced with a bond that is not cleavable under physiological conditions, and cannot be cut by endoproteases.

Preferably the noncleavable bond is a modified peptide bond, for example a reduced peptide bond, an alkylated amide bond or a thioamide bond. A reduced amide bond is a peptide bond in which the carbonyl group (C=O) has been reduced to a hydroxyl group (HCOH) or a methylene group ($CH_2$). An alkylated amide bond is a peptide bond alkylated either on the nitrogen (N-alpha) or carbon atom (C-alpha). The alkyl residue preferably has 1 to 3 carbon atoms. An example is N-methylation.

Moreover, the term "altered backbone" comprises other groups that are suitable for forming a covalent bond both with the COOH group of the preceding amino acid residue and the $NH_2$ group of the next amino acid residue, and which therefore do not necessarily maintain the peptide backbone structure, for example sugar amino acid-dipeptide isostere, azapeptides, 6-homopolymers, gamma-peptides, Y-lactam-analogs, oligo(phenylene ethylene)s, vinylog sulfone peptides, poly-N-substituted glycines or oligocarbamates.

Modifications of the backbone are in positions 14 to 19, $R-X_3-I_{16}-Y_{17}-N_{16}-X_4$. Therefore preferably at least one of the bonds between $X_3-I_{16}$ (e.g. Arg-Ile), $N_{18}-X_4$ (e.g. Asn-Arg), $X_4—NH_2$ (e.g. Arg-$NH_2$), $X_6-X_7$ (e.g. Arg-Leu or Arg-Ile) is modified. These bonds are preferably selected from the group of reduced amide bonds, alkylated amide bonds or thioamide bonds.

The peptides and peptide derivatives according to the invention can be linear, i.e. a sequence in which the first and the last amino acid of the sequence possess a free $NH_2$ and COOH group or have been modified with $Sub_1$ and $Sub_2$. Alternatively the peptides are cyclic, i.e. the first and the last amino acid are linked via a peptide bond or a linker.

The methods of producing the abovementioned novel antibiotically active compounds also form part of the invention.

The peptides or peptide derivatives of the present invention can be produced either synthetically or, where applicable, recombinantly by conventional methods. Special examples of carrying out the invention are disclosed in detail below, in the experimental section. Preferably the peptides or peptide derivatives of the present invention are produced conventionally by the known synthesis techniques, as described for example by Merrifield (Merrifield R B. Solid-phase peptide synthesis. 1. Synthesis of a Tetrapeptide. *Journal of the American Chemical Society* 85: 2149-&, 1963).

Alternatively, the peptides described in the present invention are produced by recombinant techniques, wherein a DNA fragment that contains a nucleic acid sequence that codes for one of the peptides described above is cloned, and is expressed e.g. in a microorganism or a host cell. The coding nucleic acid sequences can be produced synthetically (Stemmer W P C, Crameri A, Ha K D, Brennan T M, & Heyneker H L. Single-Step Assembly of a Gene and Entire Plasmid from Large Numbers of Oligodeoxyribonucleotides. *Gene* 164: 49-53, 1995) or can be obtained by side-specific mutagenesis of an existing nucleic acid sequence (e.g. sequence that codes for the wild-type Oncopeltus 4). The coding sequence thus produced can be amplified by RNA (or DNA) with correspondingly produced primers in a polymerase chain reaction (PCR) by known techniques. After purification, for example by agarose gel electrophoresis, the PCR product is ligated into a vector and finally the host cell is transformed with the corresponding recombinant plasmid. Recombinant techniques are known for various host cells, for example *E. coli, Bacillus, Lactobacillus, Streptomyces*, mammalian cells (e.g. CHO (Chinese hamster ovary) or COS-1 cells), yeast cells (e.g. *Saccharomyces, Schizophyllum*), insect cells or viral expression systems (e.g. Baculovirus System). Further suitable host cells and methods for transformation, cultivation, amplification, screening, product production and purification can be selected from the literature by any person skilled in the art (Gething M J & Sambrook J. Cell-Surface Expression of Influenza Hemagglutinin from a Cloned Dna Copy of the Rna Gene. *Nature* 293: 620-5, 1981). After conventional recombinant production, the peptides of the present invention can be isolated from the host cells, either by classical cell lysis techniques or from the cell medium by conventional methods, e.g. liquid chromatography, in particular affinity chromatography. The antimicrobial peptide can be expressed as individual peptide or as oligomer. The oligomers can contain several peptide sequences, which are linked via the N- or C-terminus, or even contain an N- or C-terminal tag, which allows easier purification of the recombinant peptides or protein constructs. Conventional techniques of molecular biology and site-directed mutagenesis can be used, to modify the sequence further and thus obtain the desired non-native peptide sequences. All these recombinant techniques are known by a person skilled in the art and have already been applied for many antimicrobial peptides including apidaecin (Maeno M, Taguchi S, & Momose H. Production of Antibacterial Peptide Apidaecin Using the Secretory Expression System of *Streptomyces*. *Bioscience Biotechnology and Biochemistry* 57: 1206-7, 1993), perinerin (Zhou Q F, Luo X G, Ye L, & Xi T. High-level production of a novel antimicrobial peptide perinerin in *Escherichia coli* by fusion expression. *Current Microbiology* 54: 366-70, 2007) and defensin (Si L G, Liu X C, Lu Y Y, Wang G Y, & Li W M. Soluble expression of active human beta-defensin-3 in *Escherichia coli* and its effects on the growth of host cells. *Chinese Medical Journal* 120: 708-1.3, 2007).

It is also possible for amino acids that do not occur naturally to be introduced into the peptides by gene technology. This was described in detail by Noren et al. and Ellman et al. (Noren C J, Anthonycahill S J, Griffith M C, & Schultz P G. A General Method for Site-Specific Incorporation of Unnatural Amino-Acids Into Proteins. *Science* 244: 182-8, 1989; Ellman J, Mendel D, Anthonycahill S, Noren C J, & Schultz P G. Biosynthetic Method for Introducing Unnatural Amino-Acids Site-Specifically Into Proteins. *Methods in Enzymology* 202: 301-36, 1991).

Next, the peptides can be isolated from the host cell culture or the in-vitro translation system. This can be achieved with the usual techniques for protein purification and isolation that are known from the prior art. Such techniques can for example comprise immuno-adsorption or affinity chromatography. It is also possible to provide the peptides, during synthesis, with a tag (e.g. histidine tag), which allows rapid binding and purification. The tag can later be split off enzymatically, to obtain the active peptide sequence.

If the peptide itself cannot be encoded or expressed, but is very similar to an encodable or expressible peptide, the method can first be applied to the similar peptide, which is subsequently converted in one or more steps chemically or enzymatically to the desired peptide or peptidomimetic. Some more comprehensive accounts of these methods of producing the peptides described here are described in the literature (Anderson W F. Human gene therapy. *Nature* 392: 25-30, 1998; *Pharmaceutical Biotechnology* (eds. Crommelin D J A & Sindelar R D) pp. 8-20, 53-70, 123-152, 167-180) Harwood Academic Publishers, 1997; *Protein Synthesis: Methods and Protocols* (ed. Martin R) 1-144, Humana Press, 1998; *Amino Acid and Peptide Synthesis* (ed. Jones J) 1-89, Oxford University Press, 1997; *Solid-Phase Peptide Synthesis* (ed. Fields G B) 1-780, Academic Press, 1997.

The peptides and peptide derivatives according to the invention can be used individually, in combination, as multimers or as branched multimers. Reasonable combinations of the peptides according to the invention comprise concatamers, in which the peptides according to the invention are linked together sequentially or via spacers, e.g. in the form of a peptide dimer or a peptide trimer etc. (multimer), with the individual peptides strung together. This multimer can be made up from peptides or peptide derivatives with identical sequences or different sequences according to any of the formulas 1 to 4.

Individual peptides or peptide derivatives can be coupled to a biocompatible protein, for example human serum albumin, humanized antibodies, liposomes, micelles, synthetic polymers, nanoparticles and phages. Alternatively, multimers in which the peptides or peptide derivatives according to the invention are combined individually, can be produced in the form of dendrimers or clusters, with three or more peptides bound to one center.

In one embodiment, several peptides or peptide derivatives according to any of the formulas 1 to 4 described above can be produced as multimeric constructs or arrangement. Thus, for example, optionally amino acids (e.g. Gly-Ser-) or other spacers based on amino acids or other chemical compounds can be attached to the N- or C-terminus, in order to link two or more peptides together or couple them to a carrier. This arrangement can assume the form of one or more of the synthetic peptides described above coupled to a carrier protein. Alternatively, an arrangement contains several peptides, each expressed as multiple antigenic peptide, optionally coupled to a carrier protein. In another variant the selected peptides are linked sequentially and are expressed as recombinant protein or polypeptide. In one embodiment, several peptides are linked sequentially, with or without amino acids as spacers in between, to obtain a larger recombinant protein. Alternatively the recombinant protein can be fused to a carrier protein.

In another embodiment the multimeric constructs contain at least two of the peptides defined above (which can be the same or different peptides of any of the formulas 1 to 4), wherein one peptide is coupled via any amino acid to the other peptides. Any number of further peptides can be attached to any further amino acids of these peptides. In another embodiment of a multimeric arrangement, which contains at least two peptides, the second or the further peptides is/are coupled to a branched structure of the other peptides of the basic structure. Alternatively, each further peptide is linked covalently via the group $Sub_1$ or $Sub_2$ to another peptide of the arrangement.

In another embodiment of a multimeric construct or of an arrangement with at least two peptides, at least one or more peptides are bound to a carrier. In another embodiment one or more of the stated peptides are a synthetic peptide, which is fused to a carrier protein. Furthermore, there is the alternative of combining several of the peptides described above with or without flanking sequences sequentially to a linear polypeptide. The peptides or the polypeptide are either coupled to the same carrier or different peptides can be coupled individually as peptides to one or different immunologically inert carrier proteins.

Suitable carriers improve the stability, the administration or the production, or alter or improve the activity spectrum of the peptides. Examples of carriers are human albumin, polyethylene glycol or other biopolymers or other naturally or non-naturally occurring polymers. In one embodiment, the main component of the carrier is preferably a protein or other molecule that increases the stability of the peptide. A person skilled in the art can easily select a suitable coupling unit of carrier and peptide.

In another embodiment the peptides are arranged in the form of a multiple antigenic peptide (MAP), which can for example be constructed by the "MAP" concept described by Tam et al. (Tam J P, Mora A L, & Rao C. Lipidation as a novel approach to mucosal immunization. *Modulation of the Immune Response to Vaccine Antigens* 92: 109-16, 1998). This system uses a central unit of lysine residues, onto which several copies of the same peptide according to the invention are synthesized (see e.g. Posnett D N, Mcgrath H, & Tam J P. A Novel Method for Producing Anti-Peptide Antibodies— Production of Site-Specific Antibodies to the T-Cell Antigen Receptor Beta-Chain. *Journal of Biological Chemistry* 263: 1719-25, 1988). Each MAP contains several copies of one or more of the peptides according to the invention. One embodiment of a MAP contains at least three, but preferably four or more peptides. A person skilled in the art can easily produce any number of multimeric compounds according to the peptides identified in the above formulas. All such multimeric arrangements and constructs form part of the present invention.

Further combinations in the form of multimers can be produced on the surface of particles, wherein the peptides or peptidomimetics are presented on their surface. The particle can then function as carrier of a peptide or peptidomimetic and can act simultaneously as detectable marker. Multimers can for example be obtained by N-terminal biotinylation of the N-terminal end of the peptide or peptidomimetic chains and subsequent complexation with streptavidin. As streptavidin can bind four biotin molecules or conjugates with high affinity, very stable tetrameric peptide complexes can be obtained with this method. Multimers can be produced from identical or different peptides or peptidomimetics according to the invention. Preferably the multimers according to the invention contain two or more peptides or peptidomimetics, in which each component contributes to the biocidal activity (target recognition, antimicrobial activity, purification).

Another object of the present invention is the use of the peptides or peptide derivatives according to the invention in medicine or pharmacy, e.g. for therapy with an antibiotic or in a composition with antimicrobial (in particular bactericidal) activity.

The invention also comprises a peptide, peptide derivative and/or multimer according to the invention for use in the treatment of microbial, bacterial or fungal infections.

The present invention further relates to pharmaceutical compositions that contain one or more peptides or peptide derivatives according to the invention or multimeric constructs independently of the presence of other active pharmaceutical ingredients.

The use of the peptides according to the invention as a pharmaceutical and/or for the production of an active substance that can be used as an antibiotic is also part of the present invention.

The peptides can also be used individually in pharmaceutical products. Alternatively, one or more peptides as described above can be fused or conjugated to another compound, in order to increase the pharmacokinetics or bioavailability, without inducing an immune response. Any number of individual peptides or multimeric constructs can be mixed together to produce a single composition.

A pharmaceutical composition according to the invention contains a therapeutically effective amount of one or more peptides or peptide derivatives of the present invention. Once composed, the pharmaceutical composition according to the invention can be administered to the subject directly, to treat microbial (in particular bacterial) infections. For this, a therapeutically effective amount of a composition according to the invention is administered to the subject to be treated.

The compositions according to the invention are intended for treating infections of a mammal, including humans, infected with bacteria or fungi.

At least one or alternatively also several peptides or multimeric constructs according to the invention can be mixed with a pharmacologically acceptable vehicle or other components to form a composition with antimicrobial (in particular antibacterial or fungicidal) action. For the use of such a composition, the selected peptide is preferably produced synthetically or also recombinantly, as described above.

The direct administration of this composition takes place either topically (on the surface of the skin) or by some other route of administration, for example oral, parenteral, subcutaneous, sublingual, intralesional, intraperitoneal, intravenous, intramuscular, pulmonary or interstitial into the tissue.

The pharmaceutical composition can contain further suitable and pharmaceutically acceptable vehicles, fillers or solvents and can have the form of a capsule, tablet, pastille, coated tablet, pill, drops, suppository, powder, spray, vaccine, ointment, paste, cream, inhalant, patch, aerosol or the like. Pharmaceutically acceptable excipients can include solvents, diluents or other liquid binders such as dispersion or suspension aids, surfactants, isotonically active substances, thickeners or emulsifiers, preservatives, encapsulating agent, solid binders or glidants, depending on what is most suitable for the particular dosage and at the same time is compatible with the peptide, peptidomimetic (peptide derivative), peptide conjugate or peptidomimetic conjugate.

The pharmaceutical composition therefore preferably contains a pharmaceutically acceptable vehicle. The term "pharmaceutically acceptable vehicle" also comprises a vehicle for administration of the therapeutic composition, for example antibodies or polypeptides, genes or other therapeutic agents. The term refers to any pharmaceutical vehicle which does not itself trigger the production of antibodies that could be dangerous for the individual to whom the recipe has been administered, and does not possess any unreasonable toxicity. Suitable "pharmaceutically acceptable vehicles" can be large, slowly degradable macromolecules, for example proteins, polysaccharides, polylactonic acids, polyglycolic acids, polymeric amino acids, amino acid copolymers and inactivated viral constituents. Said vehicles are familiar to a person skilled in the art.

Salts of the peptides or functionally equivalent compounds can be produced by known methods, which typically means that the peptides, peptidomimetics, peptide conjugates or peptidomimetic conjugates are mixed with a pharmaceutically acceptable acid to form an acid salt or with a pharmaceutically acceptable base to form a basic salt. Whether an acid or a base is pharmaceutically acceptable can easily be established by a person skilled in the art, knowing the application and the recipe. For instance, not all acids and bases that are acceptable for ex vivo applications can also be transferred to therapeutic recipes. Depending on the particular application, pharmaceutically acceptable acids can be of both an organic and inorganic, nature, e.g. formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid and thiocyanic acid, which form ammonium salts with the free amino groups of peptides and functionally equivalent compounds. Pharmaceutically acceptable bases that form carboxylates with free carboxylic acid groups of the peptides and functionally equivalent compounds, comprise ethylamine, methylamine, dimethylamine, triethylamine, isopropylamine, diisopropylamine and other mono-, di- and trialkylamines as well as arylamines. Moreover, pharmaceutically acceptable solvents are included.

Pharmaceutically acceptable salts can be used, for example salts of mineral acids, such as hydrochlorides, hydrobromides, phosphates, sulfates and the like; but also salts of organic acids, such as acetates, propionates, malonates, benzoates and the like. A detailed discussion of pharmaceutically acceptable ingredients is given in Remington's Pharmaceutical Sciences (Mack Pub. Co., N.J., 1991).

Pharmaceutically acceptable vehicles in the therapeutic compositions can contain liquids, for example water, salt water, glycerol and ethanol. Other excipients can also be added, such as moistening agents or emulsifiers; pH buffering substances and similar compounds can be present in said agents. Typically, the therapeutic compositions are prepared either in liquid form or as suspension for injection, and solid forms for dissolving or suspending in carrier liquids before injection are also possible. Liposomes are also included in the definition of a "pharmaceutically acceptable vehicle".

For therapeutic treatment, peptides, peptide derivatives, peptide conjugates or peptide derivative conjugates, as described above, can be produced and can be administered to a subject who requires this. The peptide, peptide derivative, peptide conjugate or peptide derivative conjugate can be administered to a subject/patient in any suitable form, preferably as a pharmaceutical composition, which is adapted to the dosage form and is present at a dose appropriate to the desired treatment.

The pharmaceutical compositions of the present invention can contain other active compounds, for example conventional antibiotics (e.g. vancomycin, streptomycin, tetracycline, penicillin) or other antimicrobially active compounds, such as fungicides, e.g. itraconazole or miconazole. Other compounds that alleviate symptoms accompanying the infection, such as fever (salicylic acid) or rash, can also be added.

Alongside the therapeutic use for the treatment of infections, or also in biological warfare, it is further possible to use the peptides or peptide derivatives according to the invention in disinfectants and/or cleaning agents (e.g. a bactericidal composition), which can be used for disinfecting and/or cleaning surfaces and/or objects. Another field of application is packaging, where peptides can be bound to packaging material or incorporated therein, or as preservatives for other materials that can readily be degraded by microorganisms. The peptides or peptide derivatives according to the invention are suitable in particular for the packaging of foodstuffs, as they have no toxic action on contact or if ingested.

Another object of the present invention is a method for treating mammals that are infected with microbes (in particular bacteria or fungi), including the administration of an effective, therapeutically active amount of the pharmaceutically active composition according to the invention.

In connection with the present invention, bacterial or fungal infections can be selected inter alia from the group comprising infections of the urogenital tract, infections of the blood ("blood-stream infections"), sepsis, respiratory tract infections, peritonitis, wound infections, infections of the digestive tract and meningitis.

The term "therapeutically effective amount" used here designates the amount of a therapeutic agent, i.e. a peptide, peptidomimetic, peptide conjugate or peptidomimetic conjugate according to the invention, which is able to reduce or completely prevent the multiplication and colony formation of the bacteria or can achieve a measurable therapeutic or prophylactic success. The effect can for example be determined for biopsies in culture, by testing the bacterial activity or with some other suitable method of assessment of the extent and degree of a bacterial infection. The precise effective amount for a subject depends on their weight and state of health, the type and the extent of the disease and the therapeutic agent or the combination of several therapeutic agents that were selected for the treatment. In particular, the compositions according to the invention can be used for reducing or preventing bacterial infections and/or biological or physical concomitant effects (e.g. fever). Methods of establishing the initial dose by a physician are known from the prior art. The doses established must be safe and successful.

The amount of a protein, peptide or nucleic acid according to the invention that is necessary for an antibacterially effective dose can be established taking into account the pathogen that causes the infection, the severity of the infection, and the patient's age, weight, sex, general physical condition etc. The necessary amount of the active component, to be antibacterially and antimycotically effective without notable side effects, depends on the pharmaceutical recipe used and the optional presence of other ingredients, such as antibiotics, antimycotics etc. For the areas of application according to the invention, an effective dose can be between 0.01 µg/kg and 50 mg/kg, preferably between 0.5 µg/kg and 10 mg/kg of the peptide, peptidomimetic, peptide conjugate or peptidomimetic conjugate in the individual being treated.

Initial doses of the peptides, peptidomimetics, multimers, peptide conjugates or peptidomimetic conjugates according to the invention can optionally be monitored by repeated administration. The frequency of the dosages depends on the factors identified above and is preferably between one and six doses per day over a treatment period from about three days to a maximum of one week.

In another, alternative composition, the peptides, peptidomimetics, peptide conjugates or peptidomimetic conjugates or mixtures according to the invention are administered by controlled or continuous release from a matrix, which has been introduced into the subject's body.

In one embodiment, a compound according to the invention is administered through the skin. This method of administration is noninvasive and patient-friendly, and at the same time it apparently leads to an increased bioavailability of the compound compared with oral administration, especially if the compound is not stable in the environment of the digestive system or if it is too large to be absorbed efficiently from the intestine. Absorption through the skin is for example possible in the nose, the cheek, under the tongue, on the gums or in the vagina. Corresponding dosage forms can be obtained by known techniques; they can be processed into nasal drops, nasal sprays, implants, films, patches, gels, ointments or tablets. Preferably, for absorption through the skin, the pharmaceutical vehicle will contain one or more components that adhere to the skin and thereby prolong the contact time of the dosage form with the adsorbing surface, so as to increase the intake by absorption.

In another embodiment the compounds are administered in a defined amount by the pulmonary route, e.g. by means of an inhaler, atomizer, aerosol spray or a dry-powder inhaler. Suitable formulations can be prepared by known methods and techniques. Transdermal or rectal delivery, as well as application in the eye, may be appropriate in some cases.

It may be advantageous for the substances according to the invention to be administered more effectively by advanced drug delivery or targeting methods. Thus, if the digestive tract is to be avoided, the dosage form can contain any substance or mixture that increases the bioavailability. This can for example be achieved by reducing degradation, e.g. by means of an enzyme inhibitor or an antioxidant. It is better if the bioavailability of the compound is achieved by an increase in the permeability of the barrier to absorption, generally the mucosa. Substances that facilitate penetration can act in various ways; some increase the fluidity of the mucosa, whereas others expand the interstices between the mucosal cells.

Yet others reduce the viscosity of the mucus on the mucosa. The preferred absorption accelerators include amphiphilic substances such as cholic acid derivatives, phospholipids, ethanol, fatty acids, oleic acid, fatty acid derivatives, EDTA, carbomers, polycarbophil and chitosan.

Indications for which the peptides, peptide derivatives, conjugates or multimers according to the invention can be used are bacterial infections both with Gram-positive and with Gram-negative bacteria, for example *Escherichia coli, Enterobacter cloacae, Erwinia amylovora, Klebsiella pneumoniae, Morganella morganii, Salmonella typhimurium, Salmonella typhi, Shigella dysenteriae, Yersinia enterocolitica, Acinetobacter calcoaceticus, Acinetobacter baumannii, Agrobacterium tumefaciens, Francisella tularensis, Legionella pneumophila, Pseudomonas syringae, Rhizobium meliloti, Haemophilus influenzae, Stenotrophomonas maltophilia, Pseudomonas aeruginosa, Proteus vulgaris* or *Proteus mirabilis*.

The invention also relates to the use of a peptide, peptide derivative or multimer according to the invention in biochemical, biotechnological, medical or pharmaceutical research or in screening, in particular for identifying substances that have a potential antibacterial or antimycotic action.

Therefore the invention also relates to a method of identifying compounds with antibacterial or antimycotic action, which comprises the following:

(i) carrying out a competitive assay with:
(a) a microorganism that is sensitive to a peptide, peptide derivative or multimer according to the invention,
(b) a peptide, peptide derivative or multimer according to the invention,
(c) at least one compound that is to be tested, by bringing (a) into contact with (b) and (c); and
(ii) selecting a test compound that displaces the peptide, peptide derivative or multimer competitively from the microorganism.

This screening process identifies test compounds that can compete with the peptide or the multimeric construct according to the invention for binding to the unknown receptor of the pathogen. In this way, small molecules that bind specifically to the same site as the peptide can be identified effectively in high-throughput screening. The test compounds presumably have the same mechanism of action as the original peptide sequence and therefore are also active against multiresistant microbes, which are eradicated by the peptides or peptide derivatives according to the invention.

The screening process is carried out by known methods, but uses at least one peptide, peptide derivative or multimer according to the invention. Preferably, for this the peptide, peptide derivative or multimer according to the invention is provided with a fluorescent, radioactive or other detectable marker. The binding behavior of the labeled peptide, peptide derivative or multimer to the microorganism is compared in the presence and in the absence of the test substance(s).

Preferably, the test compounds that compete for binding with the peptide according to the invention or a multimeric construct are then identified and are tested for their antibacterial or antimycotic action.

In one embodiment, the fluorescence is measured in a competitive assay after formation of a dimer (BIFC; bimolecular fluorescence complementation). The method permits direct visualization of intracellular protein interactions, which was demonstrated for the example of the SH3 domain from c-Abl tyrosine kinase with natural and artificial target molecules in *E. coli* (Morell M, Espargaro A, Aviles F X, & Ventura S. Detection of transient protein-protein interactions by bimolecular fluorescence complementation: The Abl-SH3 case. *Proteomics* 7: 1023-36, 2007). This test system is sufficiently sensitive even to be able to detect the interactions between proteins with low expression level in *E. coli*. It is based on adduct formation of two fragments of the yellow fluorescent protein (YFP), after the SH3 domain has bound to its partner. As soon as these two proteins have bound to one another, the two fragments of YFP form a complex, whose structure is very similar to the native protein. This can be seen from the observed fluorescence of the YFP complex, as the individual fragments do not fluoresce. A similar construct can also be designed for searching for compounds that compete for the binding site with the peptides and peptide derivatives described in the present invention. High-throughput screening can easily be transferred by a person skilled in the art to a microtiter plate in the 386-well format.

In another embodiment the peptides are used in a suitable competitive assay, to determine the capacity of the test compounds to displace the peptides competitively from the unknown receptor of the pathogens. Where desired, microorganisms (e.g. bacterium, virus or fungus), which are known to bind to the selected peptide(s), e.g. strains of *E. coli* or *K. pneumoniae*, can (depending on the assay chosen) be immobilized directly or indirectly on a suitable surface, e.g. in an ELISA format. Corresponding surfaces for immobilization are well known. For example, an inert particle ("bead") can be used. The ligand can also, however, be bound to a 96-well microtiter plate. Then selected amounts of the test compounds and of the peptides according to the invention are brought in contact with the immobilized microorganisms and the compounds that compete with the peptides for binding, to the microorganisms are selected. If these test compounds, which compete with the peptides for receptor binding on bacteria or fungi, are identified, they can be investigated further for their antibacterial or antimycotic action. Suitable methods for this are described below in the examples.

In another aspect the invention provides an isolated nucleic acid, molecule, whose sequence codes for a peptide or multimer according to the invention. The nucleic acid coding for the antibacterial or antimycotic peptide or multimeric construct according to the invention is linked operatively with a regulatory sequence, which controls its expression in the host cell. Another object of the invention is a host cell that has been transfected or transformed with the nucleic acid molecule described above.

The invention will be explained below with the following examples, without the invention being limited thereto:

EXAMPLES

Example 1

Peptide Synthesis

All chemicals for peptide synthesis were, unless stated otherwise, obtained from Fluka Chemie GmbH (Buchs, Switzerland) at highest possible purity.

All peptides and peptide derivatives were synthesized by conventional solid-phase peptide synthesis using the Fmoc/$^t$Bu strategy (Fields G B & Noble R L. Solid-Phase Peptide Synthesis Utilizing 9-Fluorenylmethoxycarbonyl Amino-Acids. *International Journal of Peptide and Protein Research* 35: 161-214, 1990) on a Syro 2000 multiple peptide synthesis robot (MultiSynTech GmbH, Witten, Germany). All standard-Fmoc amino acids were obtained from MultiSynTech GmbH (Witten, Germany) or Orpegen Pharma GmbH (Heidelberg, Germany). 2-Amino-3-guanidinopropionic acid (Agp; Iris Biotech GmbH, Marktredwitz, Germany), β-homoarginine (βHar, Fluka Chemie GmbH, Buchs, Switzerland), homoarginine (Har), N-methylarginine (N-Me-Arg) and nitroarginine (Arg($NO_2$)), Bachem AG, Bubendorf, Switzerland) were used as special arginine homologs. trans-4-Hydroxyproline (t-4-Hyp) and 2,3-diaminopropionic acid (Dap) were obtained from Novabiochem (Merck Biosciences GmbH, Darmstadt, Germany).

The peptides were synthesized either as acid on Wang resin (1.23 mmol/g) or as acid amide on Rink-amide 4-methylbenzylhydrylamine (MBHA) resin (0.67 mmol/g), from the company MultiSynTech GmbH (Witten, Germany). For later functionalization with primary amines, peptides were derivatized as peptide thioesters and for this the first amino acid was coupled to 4-sulfamino-butyryl-aminomethyl resin (SAB AM, 1.1 mmol/g; Novabiochem, Merck Biosciences GmbH, Darmstadt, Germany).

On Wang resin, the first C-terminal amino acid (5 equivalents (eq)) was coupled with 5 eq 2,6-dichlorobenzoyl chloride (Merck KGaA, Darmstadt, Germany) and 8.25 eq pyridine in dichloromethane (DCM; Biosolve BV, Valkenswaard, The Netherlands) (Sieber P. An Improved Method for Anchoring of 9-Fluorenylmethoxycarbonyl-Amino Acids to 4-Alkoxybenzyl Alcohol Resins. *Tetrahedron Letters* 28: 6147-50, 1987). The functionalization of the SAB AM resin with the C-terminal amino acid (5 eq) was carried out at −20° C. by activation with 5 eq (benzotriazol-1-yloxy)-tripyrrolidinophosphonium hexafluorophosphate (PyBOP, Novabiochem, Merck Biosciences GmbH, Darmstadt, Germany) and 10 eq N-ethyldiisopropylamine (DIPEA) in DCM (Backes B J & Ellman J A. An Alkanesulfonamide Safety-Catch Linker for Solid-Phase Synthesis. *The Journal of Organic Chemistry* 64: 2322-30, 1999).

The first amino acid was coupled to Rink-amide resin by activation of in each case 8 eq amino acid dissolved in 0.5 mol/L of 1-hydroxybenzotriazole (HOBt) with 8 eq N,N'-diisopropylcarbodiimide (DIC) in dimethylformamide (DMF; Biosolve BV, Valkenswaard, The Netherlands), as described in the automatic synthesis on previously loaded Wang and SAB AM resin.

The side-chain protective groups used were triphenylmethyl (trityl) for Cys, Asn, His and Gln, tert-butyl ether ($^t$Bu) for Tyr, Ser and Thr, tert-butyl ester (O$^t$Bu) for Asp and Glu, ω-N-2,2,4,6,7-pentamethyldihydrobenzofurane-5-sulfonyl (Pbf) for Arg, ω-N-2,2,5,7,8-pentamethylchroman-6-sulfonyl (Pmc) for βHar and Har, tert-butyloxy-carbonyl (Boc) for Lys, Orn, and Agp or ω-N-4-methoxy-2,3-6-trimethylphenyl-sulfonyl (Mtr) for N-Me-Arg. The temporary Fmoc protective group was cleaved with 40% piperidine (Biosolve BV, Valkenswaard, The Netherlands) in DMF (v/v) for 5 min and again with fresh 20% piperidine in DMF (v/v) for 10 min.

The N-termini of the peptides or peptide derivatives were acetylated, formylated or iodoacetylated by dissolving 8 eq acetic acid, formic acid or iodoacetic acid in 0.5 mol/L HOBT/DMF and activating them with 8 eq OTC in DMF. The N-terminus of the peptides or peptide derivatives was guanidated according to Gausepohl et al. (Gausepohl, H., Pieles, H., & Frank, R. W. in *Peptides: chemistry, structure and biology* (eds. Smith, J. A. & Rivier, J. E.) 523 (ESCOM, Leiden, 1992)) each with 10 eq 2-(¹H-benzotriazol-1-yl)-1,1,3,3-tetramethylaminium hexafluorophosphate (HBTU, MultiSynTech GmbH, Witten, Germany) and DIPEA in DMF. The N-termini were modified with the fluorescent dye 5,6-carboxyfluorescein (5 eq) with 5 eq HBTU and 10 eq DIPEA in DMF.

The completeness of N-terminal modifications was verified by the Kaiser test. For this, a little resin was incubated with 0.28 mol/L ninhydrin (Riedel de Haen, Seelze, Germany) in ethanol (Carl Roth GmbH+Co. KG, Karlsruhe, Germany), 0.2 mmol/L potassium cyanide in pyridine and 76% phenol in ethanol in the ratio (1:1:2) at 95° C. If a blue coloration appeared, which indicates free primary amino groups, the coupling was repeated.

On completion of synthesis of the peptides or peptide derivatives, the resins were carefully washed with DMF and DCM and dried under vacuum. The resin-bound peptides were cleaved with a mixture of water, m-cresol, thioanisole and ethanedithiol (5:5:5:2.5) in 87.5% trifluoroacetic acid (TFA) at room temperature for 4 h and at the same time the side chains were deprotected. The peptides and peptide derivatives were precipitated with cold diethyl ether and centrifuged at 3000*g. The pellet was washed twice with cold ether, dried and dissolved in 0.1% aqueous TFA (UV spectroscopy). The samples were stored at −20° C.

Prior to cleavage of the peptides on the SAB AM resin, after cleavage of the Fmoc group the N-terminus was protected with 2.0 eq di-tert-butyldicarbonate ($Boc_2O$, Fluka Chemie GmbH, Buchs, Switzerland) and 10 eq DIPEA in DMF. 100 eq of iodoacetonitrile and 20 eq DIPEA in DMF were added to the washed resin in order to activate the sulfamyl linker by alkylation (Teruya K, Murphy A C, Burlin T, Appela E, & Mazur S J. Fmoc-based chemical synthesis and selective binding to supercoiled DNA of the p53 C-terminal segment and its phosphorylated and acetylated derivatives. *Journal of Peptide Science.* 10: 479-93, 2004). For cleavage of the peptide, 50 eq propylamine in DMF (10% v/v) was added to the resin. After the DMF had been removed, the raw peptide was dissolved in a solution of water, m-cresol, thioanisole and ethanedithiol (5:5:5:2.5) in 87.5% TFA and all side-protective groups and the N-terminal Boc protective group were split off. The peptides were precipitated with cold diethyl ether and centrifuged at 3000×g. The precipitate was washed twice with cold ether, dried and dissolved in 0.1% aqueous TFA (UV spectroscopy). The samples were stored at −20° C.

The cleaved peptides and peptide derivatives were purified by RP-HPLC on an Äkta HPLC system (Amersham Bioscience GmbH, Freiburg, Germany) with a Jupiter C18 5 μm 300 Å, 250×10 mm or Jupiter C18 15 μm, 300 Å, 250×21 mm column (Phenomenex Inc., Torrance, USA).

The solvent used in each case was 0.1% aqueous TFA (eluent A) and 60% aqueous acetonitrile (Biosolve BV, Valkenswaard, The Netherlands) with 0.1% TFA (eluent B). A typical linear gradient started at 5% eluent B and elution was carried out with an increase of 1% B per minute with a flow rate of 10 mL/min (250×21 mm column) or 5 mL/min (250× 10 mm column). Detection was performed at 220, 230 and 240 μm. The purified peptides were analyzed with the same HPLC system with a Jupiter C18 5 μm, 300 Å, 150×4.6 mm column (Phenomenex Inc., Torrance, USA). It was eluted at a flow rate of 1 mL/min with a linear gradient of 5-95% B in 30 min and detected at 220 nm. In addition, the purity was determined by matrix-assisted laser desorption/ionization with time-of-flight mass spectrometry (MALDI-TOF-MS; 4700 Proteomic Analyzer, Applied Biosystems GmbH, Darmstadt, Germany). For this, 0.5 μL of peptide solution was co-crystallized with 0.5 μL of α-cyanohydroxycinnamic acid (Bruker Daltonik GmbH; Bremen, Germany) as matrix (5.3 mg/mL in 50% acetonitrile in 0.1% aqueous TFA).

Thioether linkage of the penetratin derivatives was performed by incubation of the purified penetratin-Cys monomer with 4 eq of purified iodoacetylated AMP in degassed phosphate-buffered saline (PBS, pH 7.4) at 4° C. under nitrogen. The reaction was monitored by RP-HPLC and the penetratin construct was purified after complete reaction of the penetratin-Cys monomer. The (penetratin-Cys)$_2$ dimer was obtained in parallel.

Starting from the incompletely determined sequence of the proline-rich antimicrobial peptide "Oncopeltus antibacterial peptide 4" first derivatives of peptide 4 (Table 2) were firstly synthesized with the C-terminal amino acids $N_{18}N_{19}R_{20}$ and the carboxyl function was not altered. Among the modifications at position 11, the cationic amino acids Lys and Arg showed surprisingly good properties. The derivatives displayed antibacterial activity against *E. coli* and *M. luteus* in the lower micromolar range. For further derivativization of the C-terminus, the sequence derivativized with Arg11 was selected and derivatives with different arrangement of Asn and Arg were synthesized. The derivative shortened on the C-terminus by Asn (SEQ ID NO. 18) showed amazingly high activity. As C-terminal acid amide, moreover, it attained a surprisingly high serum stability. The peptide with the sequence VDKPPYLPRPRPPRRIYNR-NH$_2$ (SEQ ID NO. 18) is called oncocin hereinafter and was further improved mainly with respect to serum stability but also antimicrobial activity.

TABLE 2

| SEQ ID NO. | Synthesis number | Sequence | E. coli BL21 A1 | M. luteus 10240 |
|---|---|---|---|---|
| 123* | O. fasciatus | VDKPPYLPRP(X/P)PPRRIYN(NR) | | |
| 2* | A25 A4 | VDKPPYLPRP <u>P</u> PPRRIYN <u>NR-OH</u> | 128 | 64 |
| 4* | A25 A5 | VDKPPYLPRP <u>T</u> PPRRIYN <u>NR-OH</u> | 128 | 64 |
| 8 | A28 B2 | VDKPPYLPRP <u>H</u> PPRRIYN <u>NR-OH</u> | 64 | 32 |
| 5 | A29 B1 | VDKPPYLPRP <u>K</u> PPRRIYN <u>NR-OH</u> | 16 | 16 |
| 14 | A25 A6 | VDKPPYLPRP <u>R</u> PPRRIYN <u>NR-OH</u> | 8 | 16 |
| 16 | A29 A6 | VDKPPYLPRP <u>R</u> PPRRIYN <u>RN-OH</u> | 8 | 16 |
| 18 | A33 B3 | VDKPPYLPRP <u>R</u> PPRRIYN <u>R-NH$_2$</u> | 4 | 8 |

*Comparative example.

TABLE 3

Review of the synthesized peptide sequences

| SEQ ID NO. | Synthesis number | Sequence |
|---|---|---|
| 1* | A21 B2 | VDKPPYLPRPPPPRRIYN-NH$_2$ |
| 2* | A25 A4 | VDKPPYLPRPPPPRRIYNNR-OH |
| 3* | A33 B1 | VDKPPYLPRP-4tHyp-PPRRIYNR-OH |
| 4* | A25 A5 | VDKPPYLPRPTPPRRIYNNR-OH |
| 5 | A29 B1 | VDKPPYLPRPKPPRRIYNNR-OH |
| 6 | A28 B1 | VDKPPYLPRPKPPRRIYNRN-OH |
| 7 | A35 A3 | VDKPPYLPRPKPPRRIYNR-NH$_2$ |
| 8 | A28 B2 | VDKPPYLPRPHPPRRIYNNR-OH |
| 9 | A28 B3 | VDKPPYLPRPHPPRRIYNRN-OH |
| 10* | A31 B2 | VDKPPYLPRPYPPRRIYNR-OH |
| 11* | A31 B3 | VDKPPYLPRPNPPRRIYNR-OH |
| 12* | A31 B4 | VDKPPYLPRPQPPRRIYNR-OH |
| 13* | A31 B5 | VDKPPYLPRPFPPRRIYNR-OH |
| 14 | A25 A6 | VDKPPYLPRPRPPRRIYNNR-OH |
| 15 | A29 A2 | VDKPPYLPRPRPPRRIYNNR-NH$_2$ |
| 16 | A29 A6 | VDKPPYLPRPRPPRRIYNRN-OH |
| 17 | A35 A2 | VDKPPYLPRPRPPRRIYNRN-NH$_2$ |
| 18 | A33 B3 | VDKPPYLPRPRPPRRIYNR-NH$_2$ |
| 19 | A35 A4 | VDKPPYLPRPRPPRRIYNR-OH |
| 20 | A31 A4 | VDKPPYLPRPRPPRPIYNR-OH |
| 21 | A31 B1 | VDKPPYL-4tHyp-RPRPPRRIYNR-OH |
| 22 | A34 A2 | VDKPPYL-4tHyp-RPRPPRRIYNR-NH$_2$ |
| 23 | A33 A6 | VDK-4tHyp-PYLPRPRPPRRIYNR-OH |
| 24 | A34 A3 | VDKPPYLPRPRP-4tHyp-RRIYNR-NH$_2$ |
| 25 | A53 E6 | VDKPPYLPRPRPPR-4tHyp-IYNR-NH$_2$ |
| 26 | A53 F3 | VDKPPYLPRPRPPRRIYNON-NH$_2$ |
| 27* | A35 A6 | VDKPPYLPRPRPPRRIYN-NH$_2$ |
| 28* | A51 A6 | VDKPPYLPRPRPPRRIYN-OH |
| 29 | A56 A1 | ADKPPYLPRPRPPRRIYNR-NH$_2$ |
| 30 | A56 A2 | VAKPPYLPRPRPPRRIYNR-NH$_2$ |
| 31* | A56 A3 | VDAPPYLPRPRPPRRIYNR-NH$_2$ |
| 32 | A56 A4 | VDKAPYLPRPRPPRRIYNR-NH$_2$ |
| 33 | A56 A5 | VDKPAYLPRPRPPRRIYNR-NH$_2$ |
| 34* | A56 A6 | VDKPPALPRPRPPRRIYNR-NH$_2$ |
| 35* | A56 B1 | VDKPPYAPRPRPPRRIYNR-NH$_2$ |
| 36 | A56 B2 | VDKPPYLARPRPPRRIYNR-NH$_2$ |
| 37* | A56 B3 | VDKPPYLPAPRPPRRIYNR-NH$_2$ |

TABLE 3-continued

Review of the synthesized peptide sequences

| SEQ ID NO. | Synthesis number | Sequence |
|---|---|---|
| 38 | A56 B4 | VDKPPYLPRARPPRRIYNR-NH$_2$ |
| 39* | A56 B5 | VDKPPYLPRPAPPRRIYNR-NH$_2$ |
| 40 | A56 B6 | VDKPPYLPRPRAPRRIYNR-NH$_2$ |
| 41 | A56 C1 | VDKPPYLPRPRPARRIYNR-NH$_2$ |
| 42* | A57 D5 | VDKPPYLPRPRPPARIYNR-NH$_2$ |
| 43* | A57 D6 | VDKPPYLPRPRPPRAIYNR-NH$_2$ |
| 44 | A56 C4 | VDKPPYLPRPRPPRRAYNR-NH$_2$ |
| 45 | A56 C5 | VDKPPYLPRPRPPRRIANR-NH$_2$ |
| 46 | A56 C6 | VDKPPYLPRPRPPRRIYAR-NH$_2$ |
| 47* | A56 D1 | VDKPPYLPRPRPPRRIYNA-NH$_2$ |
| 48* | A35 B1 | VDKPPYLPRPRPPRPIRV-OH |
| 49 | A70 A1 | VDKPPYLPRPRPPRRIYPQPRPPHPRL-NH$_2$ |
| 50 | A51 B1 | VDKPPYLPRPRPPRRIYNO-NH$_2$ |
| 51* | A51 B2 | VDKPPYLPRPRPPRRIYNN-NH$_2$ |
| 52 | A51 B3 | VDKPPYLPRPRPPRRIYNDap(Ac)-NH$_2$ |
| 53 | A56 E1 | VDKPPYLPRPRPPRRIYNH-NH$_2$ |
| 54 | A59 A2 | VDKPPYLPRPRPPRRIYNAgp-NH$_2$ |
| 55 | A59 A3 | VDKPPYLPRPRPPRRIYNArg(NO$_2$)-NH$_2$ |
| 56 | A59 A4 | VDKPPYLPRPRPPRRIYN(N—Me-Arg)-NH$_2$ |
| 57 | A59 A5 | VDKPPYLPRPRPPRRIYNHar-NH$_2$ |
| 58 | A66 D2 propyl. | VDKPPYLPRPRPPRRIYNR-NHC$_3$H$_7$ |
| 59 | A45 A6 | VDKPPYLPRPRPRPRIYNR-NH$_2$ |
| 60* | A45 A5 | VDKPPYLPRPRPPRPIYNR-NH2 |
| 61 | A45 A3 | VDKPPYLPRPRPPROIYNR-NH$_2$ |
| 62 | A51 B4 | VDKPPYLPRPRPPR-betaHArg-IYNR-NH$_2$ |
| 63 | A53 F1 | VDKPPYLPRPRPPR-4tHyp-IYNO-NH$_2$ |
| 64 | A66 C5 | VDKPPYLPRPRPPRHIYNH-NH$_2$ |
| 65 | A70 B4 | VDKPPYLPRPRPPRAgpIYNHar-NH$_2$ |
| 66 | A70 C1 | VDKPPYLPRPRPPRAgpIYNAgp-NH$_2$ |
| 67 | A70 B5 | VDKPPYLPRPRPPRHarIYNHar-NH$_2$ |
| 68 | A70 C2 | VDKPPYLPRPRPPRHarIYNAgp-NH$_2$ |
| 69 | A70 C3 | VDKPPYLPRPRPPROIYNAgp-NH$_2$ |
| 70 | A70 B6 | VDKPPYLPRPRPPROIYNHar-NH$_2$ |
| 71 | A66 D3 propyl. | VDKPPYLPRPRPPROIYNR-NHC$_3$H$_7$ |
| 72 | A53 F2 | VDKPPYLPRPRPPROIYNO-NH$_2$ |
| 73 | A66 C6 | VDKPPYLPRPRPPROLYNO-NH$_2$ |
| 74 | A66 D1 | VDKPPYLPRPRPPROIYQO-NH$_2$ |

TABLE 3-continued

Review of the synthesized peptide sequences

| SEQ ID NO. | Synthesis number | Sequence |
|---|---|---|
| 75 | A56 D2 | VEKPPYLPRPRPPRRIYNR-NH$_2$ |
| 76 | A56 D3 | VDRPPYLPRPRPPRRIYNR-NH$_2$ |
| 77 | A56 D4 | VDKPPYIPRPRPPRRIYNR-NH$_2$ |
| 78 | A56 D5 | VDKPPYLPRPRPPRRLYNR-NH$_2$ |
| 79 | A56 D6 | VDKPPYLPRPRPPRRIYQR-NH$_2$ |
| 80 | A32 D3 ac. | Ac-VDKPPYLPRPRPPRRIYNR-OH |
| 81 | A32 D3 fo. | For-VDKPPYLPRPRPPRRIYNR-OH |
| 82 | A45 A2 | ODKPPYLPRPRPPRRIYNR-NH$_2$ |
| 83 | A45 A2 ac. | Ac-ODKPPYLPRPRPPRRIYNR-NH$_2$ |
| 84 | A45 A4 guan. | Guan-VDKPPYLPRPRPPRRIYNR-NH$_2$ |
| 85 | A62 B3 guan. | Guan-VDKPPYLPRPRPPROIYNO-NH$_2$ |
| 86* | A35 A5 | DKPPYLPRPRPPRRIYNR-NH$_2$ |
| 87* | A54 E1 | GNNRPVYIPQPRPPHPRL-OH |
| 88* | A60 E4 CF | *CF*-GNNRPVYIPQPRPPHPRL-OH |
| 89* | A34 B3 | GKPRPYSPRPTSHPRPIRV-OH |
| 90* | A60 E2 CF | *CF*-GKPRPYSPRPTSHPRPIRV-OH |
| 91* | A35 A1 | VDKGSYLPRPTPPRPIYNRN-NH$_2$ |
| 92* | A60 E6 CF | *CF*-VDKGSYLPRPTPPRPIYNRN-NH$_2$ |
| 93 | A33 B3 | VDKPPYLPRPRPPRRIYNR-NH$_2$ |
| 94 | A60 F2 CF | *CF*-VDKPPYLPRPRPPRRIYNR-NH$_2$ |
| 95 | A60 E4 F5 | RQIKIWFQNRRMKWKKC-(CH$_2$CO-GNNRPVYIPQPRPPHPRL-OH)-OH |
| 96 | A60 E4 F6 CF | *CF*-RQIKIWFQNRRMKWKKC-(CH$_2$CO-GNNRPVYIPQPRPPHPRL-OH)-OH |
| 97 | A60 E2 F5 | RQIKIWFQNRRMKWKKC-(CH$_2$CO-GKPRPYSPRPTSHPRPIRV-OH)-OH |
| 98 | A60 E2 F6 CF | *CF*-RQIKIWFQNRRMKWKKC-(CH$_2$CO-GKPRPYSPRPTSHPRPIRV-OH)-OH |
| 99 | A60 E6 F5 | RQIKIWFQNRRMKWKKC-(CH$_2$CO-VDKGSYLPRPTPPRPIYNRN-NH$_2$)-OH |
| 100 | A60 E6 F6 CF | *CF*-RQIKIWFQNRRMKWKKC-(CH$_2$CO-VDKGSYLPRPTPPRPIYNRN-NH$_2$)-OH |
| 101 | A60 F2 F5 | RQIKIWFQNRRMKWKKC-(CH$_2$CO-VDKPPYLPRPRPPRRIYNR-NH$_2$)-OH |
| 102 | A60 F2 F6 CF | *CF*-RQIKIWFQNRRMEWKKC-(CH$_2$CO-VDKPPYLPRPRPPRRIYNR-NH$_2$)-OH |
| 103* | A60 F5 | (RQIKIWFQNRRMKWKKC-OH)$_2$ |
| 104* | A60 F5 CF | (*CF*-RQIKIWFQNRRMKWKKC-OH)$_2$ |
| 105* | A60 G1 | RQIKIWFQNRRMKWKK-OH |
| 106* |  | RQIKIWFQNRRMKWKKC(CH$_2$CO-ffSGDRSGYSSRGS-OH)-OH |
| 107 | A74 C6 | VDKPPYLPRPRP-4tHyp-ROIYNO-NH$_2$ |
| 108 | A74 D1 | VDKPPYLPRPRP-4tHyp-R-4tHyp-IYNO-NH$_2$ |
| 109 | A76 B3 | VDKPPYLPRPRPPRO-Tle-YNO-NH$_2$ |
| 110 | A76 B5 | VDKPPYLPRPRP-4tHyp-R-4tHyp-Tle-YNO-NH$_2$ |
| 111 | T1 D9 | VDKPPYLPRPRPPRrIYNR-NH$_2$ |

TABLE 3-continued

Review of the synthesized peptide sequences

| SEQ ID NO. | Synthesis number | Sequence |
|---|---|---|
| 112 | T1 DI1 | VDKPPYLPRPRPPRrIYNr-NH$_2$ |
| 113* | A82 A4 | ONYIORPPRPRPLYPPKDV-NH$_2$ |
| 114* | A82 A5 | ONYI-4tHyp-RPPRPRPLYPPKDV-NH$_2$ |
| 115* | T1 C7 | vdkppylprprpprriynr-NH$_2$ |
| 116* | T1 C9 | vdkppylprprpproiyno-NH$_2$ |
| 117* | T1 C11 | rnyirrpprprplyppkdv-NH$_2$ |
| 118* | T1 D1 | onyiorpprprplyppkdv-NH$_2$ |

The single-letter code was used for the amino acid residues, with O in the amino acid chain standing for ornithine;

Propyl stands for a propylamide on the C-terminus (Sub$_2$=OR$_3$=NHC$_3$H$_7$); Ac=acetyl group, for=formyl group, guan=guanidino group and CF=5,6-carboxyfluorescein Examples of modified N-termini (modified alpha-amino group of the N-terminal amino acid, Sub$_1$=acetyl-NH, formyl-NH, guanidino or 5,6-carboxyfluorescein), βHar: β-homoarginine, the beta-amino acid homologs to arginine, Agp: 2-amino-3-guanidinopropionic acid, Har: homoarginine and Arg(NO$_2$): nitroarginine are homologs of arginine, N-Me-Arg: N-methyl-arginine—an arginine methylated on the peptide bond, 4tHyp: trans-4-hydroxyproline, Tle: tert-butyl glycine Dap(Ac): 2,3-diaminopropionic acid with acetylated amino function in the side chain, (CH$_2$CO): acetyl linker to SH group of cysteine, f: α-aminocapronic acid, lower-case letters stand for the corresponding D-amino acids, comparative examples are marked with *.

Example 2

Stability

Serum Stability in 25% Mouse Serum

The serum stability studies were performed as double determination according to Hoffmann et al. (Hoffmann R, Vasko M, & Otvos L. Serum stability of phosphopeptides. *Analytica Chimica Acta* 352: 319-25, 1997) in mouse serum and 25% aqueous mouse serum (PAA Laboratories GmbH; Pasching, Austria). For this, the peptides and peptidomimetics were dissolved in water, mouse serum was added and the peptide concentration was adjusted to 75 µg/mL. While shaking continuously, the mixture was incubated at 37° C. After 0, 30, 60, 120, 240 and 360 minutes, in each case an aliquot was taken and mixed with 15% aqueous trichloroacetic acid (Carl Roth GmbH & Co. KG; Karlsruhe, Germany). After incubation on ice for a further 10 minutes, the precipitated serum proteins were centrifuged off (5 min, 13400 rpm, MiniSpin, Eppendorf AG, Hamburg, Germany). The supernatant was removed, neutralized with 1 mol/L aqueous sodium hydroxide solution (Fluke Chemie GmbH, Buchs, Switzerland) and stored at −20° C. until analysis.

The supernatants were analyzed by RP-HPLC with a linear acetonitrile gradient (Biosolve BV, Valkenswaard, The Netherlands) in the presence of 0.1% trifluoroacetic acid (TFA, UV-grade, Fluka Chemie GmbH, Buchs, Switzerland) as ion-pairing reagent. The fractions were co-crystallized with α-cyanohydroxycinnamic acid (Bruker Daltonik GmbH; Bremen, Germany) as matrix (5.3 mg/mL in 50% acetonitrile in 0.1% aqueous TFA) and were analyzed with a tandem mass spectrometer (MALDI-TOF/TOF-MS, 4700 Proteomics Analyzer; Applied Biosystems GmbH, Weiterstadt, Germany) in the positive-ion reflector mode. The proportion of intact peptides and their degradation products or metabolites could thus be identified and quantified at the individual time points. The control used was 25% aqueous mouse serum, which was analyzed in parallel for the same time intervals.

Table 4 shows the half-lives of oncocin (SEQ ID NO. 18) and selected oncocin derivatives in 25% mouse serum. The listed Oncopeltus 4 derivatives with SEQ ID NO. 14 and 19 have the lowest stability, with a half-life of less than 30 min. Here, the arginine at position 19 (residue X$_4$) is cleaved first. The stability of the degradation product VDKPPYLPRPRP-PRRIYN-OH (SEQ ID NO. 28) then increases to 120 min, but this fragment still only has very low antimicrobial activity (64 µg/mL, *E. coli*). On amidation of the C-terminus (Sub$_2$) in oncocin, besides the activity against *E. coli* and *M. luteus* (4 and 8 µg/mL, respectively), the stability also increases to 60 min, a surprisingly high value for peptide derivatives. Through amidation with propylamide (SEQ ID NO. 58), the half-life of oncocin was even lengthened to 120 min.

TABLE 4

Serum stability: half-lives of oncocin and selected oncocin derivatives in 25% mouse serum

| SEQ ID NO. | Synthesis No. | Sequence | E. coli BL21 A1 | M. Luteus 10240 | Half-life |
|---|---|---|---|---|---|
| 14 | A25 A6 | VDKPPYLPRPRPPRRIYNNR-OH | 8 | 16 | <30 min |
| 19 | A35 A4 | VDKPPYLPRPRPPRRIYNR-OH | 32 | 64 | <30 min |
| 17 | A35 A2 | VDKPPYLPRPRPPRRIYNRN-NH$_2$ | 16 | 128 | 45 min |
| 18 | A33 B3 | VDKPPYLPRPRPPRRIYNR-NH$_2$ | 4 | 8 | 60 min |
| 24 | A34 A3 | VDKPPYLPRPRP-4tHyp-RRIYNR-NH$_2$ | 8 | 8 | 60 min |
| 61 | A45 A3 | VDKPPYLPRPRPPROIYNR-NH$_2$ | 8 | 16 | 90 min |
| 28* | A51 A6 | VDKPPYLPRPRPPRRIYN-OH | 64 | 128 | 120 min |
| 50 | A51 B1 | VDKPPYLPRPRPPRRIYNO-NH$_2$ | 8 | 16 | 120 min |
| 51* | A51 B2 | VDKPPYLPRPRPPRRIYNN-NH$_2$ | 16 | 64 | 120 min |
| 58 | A66 D2 propyl. | VDKPPYLPRPRPPRRIYNR-NHC$_3$H$_7$ | 4 | 8 | >120 min |
| 60* | A45 A5 | VDKPPYLPRPRPPRPIYNR-NH$_2$ | 8 | 64 | 120 min |
| 62 | A51 B4 | VDKPPYLPRPRPPR-betaHArg-IYNR-NH$_2$ | 4 | 16 | 150 min |
| 63 | A53 F1 | VDKPPYLPRPRPPR-4tHyp-IYNO-NH$_2$ | 4 | 8 | >360 min |
| 71 | A66 D3 propyl. | VDKPPYLPRPRPPROIYNR-NHC$_3$H$_7$ | 4 | 8 | >360 min |
| 72 | A53 F2 | VDKPPYLPRPRPPROIYNO-NH$_2$ | 8 | 16 | >360 min |

*comparative examples.

The substitution of position 19 (residue $X_4$) for the non-proteinogenic amino acid ornithine (SEQ ID NO. 61) increased the stability to 120 min half-life. The substitution of Arg15 for ornithine increased the stability of this oncocin derivative (SEQ ID NO. 50) to 90 min half-life. The derivatives with proline (SEQ ID NO. 60) or β-homoarginine (SEQ ID NO. 62) at position 15 (residue $X_3$) were not degraded to half until after 120 or 150 min. The substitution of the proline at position 13 in 4-trans-hydroxyproline (SEQ ID NO. 24) did not have any negative effect on the stability of oncocin.

By combining these modifications at position 15 and 19 (residues $X_1$ and $X_4$) it was possible to synthesize very stable peptide derivatives, for which half-lives of over 360 min were determined. The activity of the preferred examples SEQ ID NO. 63 and 72 with Orn19 and Hyp15 or Orn15 with MIC values of 4 or 8 mg/ml, against E. coli was comparable to oncocin. The combination of Orn15 with propylamidated C-terminus (SEQ ID NO. 71) represents another very preferred example of the invention.

Serum Stability in 100% Mouse Serum

TABLE 5

Serum stability: half-lives of oncocin and selected oncocin derivatives in 100% mouse serum

| SEQ ID NO. | Synthesis No. | Sequence | E. coli BL21 A1 | M. luteus 10240 | Half-life |
|---|---|---|---|---|---|
| 18 | A33 B3 | VDKPPYLPRPRPPRRIYNR-NH$_2$ | 4 | 8 | 30 min |
| 24 | A34 A3 | VDKPPYLPRPRP-4tHyp-RRIYNR-NH$_2$ | 8 | 8 | 35 min |
| 61 | A45 A3 | VDKPPYLPRPRPPROIYNR-NH$_2$ | 8 | 16 | 65 min |
| 58 | A66 D2 propyl. | VDKPPYLPRPRPPRRIYNR-NHC$_3$H$_7$ | 4 | 8 | 60 min |
| 67 | A70 B5 | VDKPPYLPRPRPPR-Har-IYN-Har-NH$_2$ | 4 | 4 | 55 min |
| 63 | A53 F1 | VDKPPYLPRPRPPR-4tHyp-IYNO-NH$_2$ | 4 | 8 | >480 min 60% |

TABLE 5-continued

Serum stability: half-lives of oncocin and
selected oncocin derivatives in 100% mouse serum

| SEQ ID NO. | Synthesis No. | Sequence | E. coli BL21 A1 | M. luteus 10240 | Half-life |
|---|---|---|---|---|---|
| 71 | A66 D3 propyl. | VDKPPYLPRPRPPROIYNR-NHC$_3$H$_7$ | 4 | 8 | 105 min |
| 72 | A53 F2 | VDKPPYLPRPRPPROIYNO-NH$_2$ | 8 | 16 | 175 min |
| 25 | A53 E6 | VDKPPYLPRPRPPR-4tHyp-IYNR-NH$_2$ | 16 | 8 | 240 min |
| 107 | A74 C6 | VDKPPYLPRPRP-4tHyp-ROIYNO-NH$_2$ | 4 | 4 | n.d. |
| 108 | A74 D1 | VDKPPYLPRPRP-4tHyp-R-4tHyp-IYNO-NH$_2$ | 2 | 32 | 150 min |
| 109 | A76 B3 | VDKPPYLPRPRPPRO-Tle-YNO-NH$_2$ | 4 | 4 | 130 min |
| 110 | A76 B5 | VDKPPYLPRPRP-4tHyp-R-4tHyp-Tle-YNO-NH$_2$ | 2 | 16 | >480 min 70% |

By exchanging the arginine residues at position 15 and 19 with ornithine or trans-4-hydroxyproline (SEQ ID NO. 63 and 72), the half-life in 25% aqueous mouse serum could be increased to more than 6 hours (see above). After incubation in 100% mouse serum, on exchanging $R_{15}O$ and $R_{19}O$ a half-life of 175 minutes was determined for these sequences. By exchanging $R_{15}$Hyp and $R_{19}O$ (SEQ ID NO. 63), 60% of the amount of peptide used was still detected after 480 min. Another derivative of oncocin with $P_{13}$Hyp, $R_{15}$Hyp, $R_{19}O$ and $I_{16}$Tle (SEQ ID NO. 110) still contained even 60% or 70% of the original amount of peptide after 480 min. The activity of both derivatives against *E. coli* was very good, at 4 and 2 µg/mL.

Stability Against Bacterial Proteases

Preparation of Bacterial Lysate

For the bacterial lysate, 500 mL of nutrient broth (Carl Roth GmbH+Co. KG, Karlsruhe) was inoculated with *E. coli* BL21 A1 and incubated overnight at 37° C. 2×250 mL bacterial suspension were centrifuged for 25 min at 5000 rpm and 4° C. in a Beckman Avanti™ J-20-XP centrifuge with JLA-10.500 rotor (Beckman Coulter, Fullerton, U.S.A.). The pellets were each suspended in 30 mL PBS (pH 7.4) and centrifuged again in a Beckman Allegra™ 2IR centrifuge (Beckman Coulter, Fullerton, U.S.A.). The pellets were each suspended in 10 mL PBS and were disrupted with ultrasound (Vibra-cell™ microtip, Fisher Bioblock Scientific, Illkirch, France) 2×5 min (750 W; amplitude 40%; 2 s on/3 s off) on ice. The bacterial lysates were combined and 1 mL aliquots were centrifuged at 15400 rpm for 20 min at 4° C. (Beckman Allegra™). The supernatants were removed and stored at −20° C. The protein content of the bacterial lysate was determined by protein determination according to Bradford.

*Protein determination according to Bradford* [M. M. Bradford; (1976): *Analytische Biochemie*, 72, 248-254]

A 2 mg/mL BSA solution in PBS was prepared as the stock solution for the standard series. This was diluted with PBS, to give 6 standard solutions from 10 to 100 µg/mL BSA. A dilution series in PBS was prepared from the sample to be analyzed. In each case 50 µL of sample or standard solution was pipetted into a polystyrene microplate. For the Bradford reagent, 0.01% Coomassie Brilliant Blue G250 was dissolved in 5% ethanol, 8.5% o-phosphoric acid was added and it was topped up with doubly-distilled water. The mixture was then incubated for 1 h at 60° C. and left to stand for a further 12 h at RT, and then filtered. 200 µL of the Bradford reagent was added to each well and incubated in the dark for 15 min. The absorption was measured at 595 nm against a blank value (50 µL PBS+200 µL Bradford reagent).

Determination of the Stability in Bacterial Lysate

A solution of 0.15 µg/mL peptide in bacterial lysate with protein content of 1.5 mg/mL or 0.5 mg/mL was incubated at 37° C. After 0, 30, 60, 120, 240 or 360 min, 200 µL was taken from each and the proteins were precipitated with 50 µL of 15% trichloroacetic acid. Then it was incubated for 10 min at 4° C. and then centrifuged for 5 min at 13000 rpm in a Minispin desktop centrifuge. 210 µL was taken from the supernatant and neutralized with 1 mol/L sodium hydroxide solution. The intact peptide and the degradation products were analyzed by HPLC. 60 µL of 3% aqueous acetonitrile with 0.1% trifluoroacetic acid (TFA) was added to the solution and 250 µL of the mixture was injected. After chromatographic separation, the constituents were identified by MALDI-TOF-MS,

TABLE 6

Stability against bacterial proteases: half-lives of oncocin and selected oncocin derivatives after incubation in *E. coli* lysate with 0.5 mg/mL protein concentration

| SEQ ID NO. | Synthesis No. | Sequence | *E. coli* BL21 AI | *M. luteus* 10240 | Half-life |
|---|---|---|---|---|---|
| 18 | A33 B3 | VDKPPYLPRPRPPRRIYNR-NH$_2$ | 4 | 8 | 60 min |
| 25 | A53 E6 | VDKPPYLPRPRPPR-4tHyp-IYNR-NH$_2$ | 16 | 8 | n.d. |
| 72 | A53 F2 | VDKPPYLPRPRPPROIYNO-NH$_2$ | 8 | 16 | 125 min |
| 73 | A66 C6 | VDKPPYLPRPRPPROLYNO-NH$_2$ | 8 | 16 | 90 min |
| 107 | A74 C6 | VDKPPYLPRPRP-4tHyp-ROIYNO-NH$_2$ | 4 | 4 | 215 min |
| 108 | A74 D1 | VDKPPYLPRPRP-4tHyp-R-4tHyp-IYNO-NH$_2$ | 2 | 32 | >240 min 60% |
| 109 | A76 B3 | VDKPPYLPRPRPPRO-Tle-YNO-NH$_2$ | 4 | 4 | >240 min 90% |
| 110 | A76 B5 | VDKPPYLPRPRP-4tHyp-R-4tHyp-Tle-YNO-NH$_2$ | 2 | 16 | >240 min 90% |

In order to investigate the stability against bacterial proteases, a lysate was prepared from an overnight culture of *E. coli* BL21 A1 and the peptides were incubated in it. Using Bradford protein determination, the protein concentration was adjusted to 0.5 or 1.5 mg/mL.

For the native oncocin (SEQ ID NO. 18), a half-life of 60 minutes was determined in the lysate with a total protein concentration of 0.5 mg/mL. By exchanging $R_{15}O$ and $R_{19}O$ (SEQ ID NO. 72) the half-life was doubled to 115 min. In the next step, the proline at position 13 of a cleavage site of the proline endopeptidase was exchanged for trans-4-hydroxyproline (SEQ ID NO. 107), with further increase in stability to 215 min. By combining $P_{13}Hyp$, $R_{15}Hyp$ and $R_{19}O$, a half-life of more than 240 min was achieved.

In another derivative with $R_{15}O$ and $R_{19}O$, the isoleucine at position 16 was exchanged for tert-butylglycine (SEQ ID NO. 109), increasing the stability to more than 240 min. The derivatives with the combination $P_{13}Hyp$, $R_{15}Hyp$, $R_{19}O$ and $I_{16}Tle$ (SEQ ID NO. 110) also attained half-lives of more than 240 min in lysate with protein concentration of 0.5 mg/mL. Surprisingly, the oncocin derivative had positive effects on the antibacterial activity against *E. coli* and reduced the MIC value for SEQ ID NO. 108 and 110 to 2 µg/mL.

Example 3

Antibacterial Tests

Inhibition Zone Test (Agar Diffusion Assay)

The purified peptides and peptide derivatives were diluted in water to a final concentration of 500 µg/mL. The test microbes were plated out from a culture in the logarithmic growth phase at a concentration of approx. 3×10$^5$ cells/mL in 1% tryptic soy broth and 1.2% agarose (Fluka Chemie GmbH, Buchs, Switzerland). With spacing of 3 cm, in each case 10 µL of aqueous peptide solution (500 µg/mL) or 10 µL of water and antibiotic solution as controls were added dropwise. After incubation for 20 h at 37° C., the inhibition zone diameter (IZD) was determined. All tests were performed in aerobic conditions.

Using the alanine scan of the oncocin sequence, various residues were identified, whose exchange for alanine led to a marked decrease in antimicrobial activity against *E. coli* BL21 A1 (FIG. 1) and *M. luteus* 10240 (FIG. 2).

In FIG. 1 and FIG. 2, the sequence of oncocin VDKPPYL-PRPRPPRRIYNR (SEQ ID NO. 18) is plotted on the X-axis. Each amino acid represents the corresponding peptide with the alanine exchanged at this position. For example, the column Val1 stands for the peptide ADKPPYLPRPRP-PRRIYNR-NH$_2$ (SEQ ID NO. 29), to which the value of the IZD is assigned on the Y-axis. The larger the diameter of the inhibition zone, the higher the activity of the peptide.

In the agar diffusion assays against, *E. coli* BL21 A1 (FIG. 1) it was found that both the alanine exchange at positions Lys3, Tyr6-Arg9 and Arg11 reduced the activity markedly compared with oncocin (IZD 1.7 cm). These derivatives (SEQ ID NO. 31, 34 to 37 and 39) only partially inhibit the growth of *E. coli* on the agar plate, sometimes with grown-over inhibition zones with 1.0 to 1.2 cm diameter. The peptide Ala15 had the smallest inhibition zone without growth (1.3 cm; SEQ ID NO. 43). All other positions can be altered without reducing the activity, wherein however an increase in activity, expansion of the spectrum, stabilization and a better in-vivo distribution can be achieved. Positive effects were achieved here mainly at the N-terminal Val1 and at the C-terminal Arg19, when protease-stable amine acids are incorporated and the serum stability is thus increased, without losing the antimicrobial activity.

The agar diffusion assays against the Gram-positive bacterium *M. luteus* (FIG. 2) showed that as a result of alanine exchange, there are both positive and negative effects on antimicrobial activity. Positions important for activity are distributed over the whole sequence; here, the peptides inhibit growth completely with minimally smaller inhibition zones relative to oncocin (1.8 cm). Mainly the exchange of Lys or Arg and therefore the loss of a positive charge in the peptide reduces the antimicrobial activity. The largest increase in activity, at 0.7 cm, was achieved by exchanging Ile16 and Asn18 (SEQ ID NO. 44, 46). Changes at these positions are found in examples with in each case Orn15 and Orn19 and a substitution in position 16 for Leu (SEQ ID NO. 73) or position 18 for Gln (SEQ ID NO. 74). SEQ ID NO. 74 attains, by these three substitutions, an activity that corresponds to that of oncocin, wherein the Gln18 can compensate the small negative effect of the ornithine substitution.

Growth Inhibition Assay

The minimum inhibitory concentrations (MIC) of the antimicrobial peptides and peptide derivatives were determined in microdilution assays. These used a continuous peptide dilution in sterile flat-bottomed 96-well microtiter plates (polystyrene, Greiner Bio-One GmbH, Frickenhausen, Germany) and a total volume of 100 µL per well. The aqueous peptide or peptidomimetic solutions were diluted with 1% TSB water, to obtain a final concentration of 256 µg/mL. 50 µL of the peptide or peptidomimetic solution was pipetted into the first well of each series and stirred. From this solution, 50 µL was transferred to the second well, stirred and again 50 µL was transferred to the next well, and so on. A double dilution series is obtained, beginning at 256 µg/mL in the first well to 125 ng/mL in the twelfth well. The bacteria, e.g. *E. coli* BL21 A1, were cultured overnight at 37° C. in nutrient broth (NB, Carl Roth GmbH+Co. KG, Karlsruhe, Germany). 50 µL of a $5 \times 10^6$ bacteria/mL suspension in 1% TSB was added to each well of the microtiter plate and thus a final concentration of the peptides or peptidomimetics from 128 µg/mL (well 1) to 62.5 ng/mL (well 12) was established in each series. The plates were incubated at 37° C. for 20 h and then the absorption was measured at 595 nm with a TECAN microtiter plate spectrophotometer (Tecan Trading AG, Mannedorf, Switzerland). The MIC values of all peptides and peptidomimetics were determined in triplicate. Sterile water was used as negative control. The MIC value represents the lowest peptide concentration at which no bacterial growth is observed after an incubation time of 20 h at 37° C.

The MIC values of the peptides and peptide derivatives against *Escherichia coli* BL21 A1 and *Micrococcus luteus* ATCC 10240 are given in Table 7.

TABLE 7

Antimicrobial activity against *E. coli* BL21 A1 and *M. luteus* 10240. Minimum inhibitory concentration (MIC) determined in 1% TSB.

| SEQ ID NO. | Synthesis number | Sequence | *E. coli* BL21 AI | *M. luteus* 10240 |
|---|---|---|---|---|
| 1* | A21 B2 | VDKPPYLPRPPPPRRIYN-NH₂ | 128 | n.d. |
| 2* | A25 A4 | VDKPPYLPRPPPPRRIYNNR-OH | 128 | 64 |
| 3* | A33 B1 | VDKPPYLPRP-4tHyp-PPRRIYNR-OH | 128 | 32 |
| 4* | A25 A5 | VDKPPYLPRPTPPRRIYNNR-OH | 128 | 64 |
| 5 | A29 B1 | VDKPPYLPRPKPPRRIYNNR-OH | 16 | 16 |
| 6 | A28 B1 | VDKPPYLPRPKPPRRIYNRN-OH | 32 | 16 |
| 7 | A35 A3 | VDKPPYLPRPKPPRRIYNR-NH₂ | 8 | 16 |
| 8 | A28 B2 | VDKPPYLPRPHPPRRIYNNR-OH | 64 | 32 |
| 9 | A28 B3 | VDKPPYLPRPHPPRRIYNRN-OH | 64 | 16 |
| 10* | A31 B2 | VDKPPYLPRPYPPRRIYNR-OH | 128 | 16 |
| 11* | A31 B3 | VDKPPYLPRPNPPRRIYNR-OH | 64 | 64 |
| 12* | A31 B4 | VDKPPYLPRPQPPRRIYNR-OH | 64 | 64 |
| 13* | A31 B5 | VDKPPYLPRPFPPRRIYNR-OH | 64 | 32 |
| 14 | A25 A6 | VDKPPYLPRPRPPRRIYNNR-OH | 8 | 16 |
| 15 | A29 A2 | VDKPPYLPRPRPPRRIYNNR-NH₂ | 8 | 8 |
| 16 | A29 A6 | VDKPPYLPRPRPPRRIYNRN-OH | 8 | 16 |
| 17 | A35 A2 | VDKPPYLPRPRPPRRIYNRN-NH₂ | 16 | 128 |
| 18 | A28 A4/A33 B3 | VDKPPYLPRPRPPRRIYNR-NH₂ | 4 | 8 |
| 19 | A35 A4 | VDKPPYLPRPRPPRRIYNR-OH | 32 | 64 |
| 20 | A31 A4 | VDKPPYLPRPRPPRPIYNR-OH | 8 | 16 |
| 21 | A31 B1 | VDKPPYL-4tHyp-RPRPPRRIYNR-OH | 16 | 16 |
| 22 | A34 A2 | VDKPPYL-4tHyp-RPRPPRRIYNR-NH₂ | 8 | 4 |
| 23 | A33 A6 | VDK-4tHyp-PYLPRPRPPRRIYNR-OH | 8 | 16 |
| 24 | A34 A3 | VDKPPYLPRPRP-4tHyp-RRIYNR-NH₂ | 8 | 8 |
| 25 | A53 E6 | VDKPPYLPRPRPPR-4tHyp-IYNR-NH₂ | 16 | 8 |

TABLE 7-continued

Antimicrobial activity against *E. coli* BL21
A1 and *M. luteus* 10240. Minimum inhibitory concentration
(MIC) determined in 1% TSB.

| SEQ ID NO. | Synthesis number | Sequence | E. coli BL21 AI | M. luteus 10240 |
|---|---|---|---|---|
| 26 | A53 F3 | VDKPPYLPRPRPPPRRIYNON-NH$_2$ | 8 | 8 |
| 27* | A35 A6 | VDKPPYLPRPRPPPRRIYN-NH$_2$ | 32 | 64 |
| 28* | A51 A6 | VDKPPYLPRPRPPPRRIYN-OH | 64 | 128 |
| 29 | A56 A1 | ADKPPYLPRPRPPPRRIYNR-NH$_2$ | 8 | 4 |
| 30 | A56 A2 | VAKPPYLPRPRPPPRRIYNR-NH$_2$ | 16 | 4 |
| 31* | A56 A3 | VDAPPYLPRPRPPPRRIYNR-NH$_2$ | 64 | 32 |
| 32 | A56 A4 | VDKAPYLPRPRPPPRRIYNR-NH$_2$ | 8 | 8 |
| 33 | A56 A5 | VDKPAYLPRPRPPPRRIYNR-NH$_2$ | 8 | 8 |
| 34* | A56 A6 | VDKPPALPRPRPPPRRIYNR-NH$_2$ | 128 | 16 |
| 35* | A56 B1 | VDKPPYAPRPRPPPRRIYNR-NH$_2$ | 128 | 16 |
| 36 | A56 B2 | VDKPPYLARPRPPPRRIYNR-NH$_2$ | 32 | 8 |
| 37* | A56 B3 | VDKPPYLPAPRPPPRRIYNR-NH$_2$ | 32 | 32 |
| 38 | A56 B4 | VDKPPYLPRAPPPRRIYNR-NH$_2$ | 32 | 8 |
| 39* | A56 B5 | VDKPPYLPRPAPPRRIYNR-NH$_2$ | 64 | 16 |
| 40 | A56 B6 | VDKPPYLPRPRAPRRIYNR-NH$_2$ | 16 | 8 |
| 41 | A56 C1 | VDKPPYLPRPRPARRIYNR-NH$_2$ | 16 | 8 |
| 42* | A57 D5 | VDKPPYLPRPRPPARIYNR-NH$_2$ | 16 | 32 |
| 43* | A57 D6 | VDKPPYLPRPRPPRAIYNR-NH$_2$ | 32 | 16 |
| 44 | A56 C4 | VDKPPYLPRPRPPRRAYNR-NH$_2$ | 16 | 16 |
| 45 | A56 C5 | VDKPPYLPRPRPPRRIANR-NH$_2$ | 8 | 16 |
| 46 | A56 C6 | VDKPPYLPRPRPPRRIYAR-NH$_2$ | 8 | 8 |
| 47* | A56 D1 | VDKPPYLPRPRPPPRRIYNA-NH$_2$ | 32 | 16 |
| 48* | A35 B1 | VDKPPYLPRPRPPRPIRV-OH | 128 | 8 |
| 49 | A70 A1 | VDKPPYLPRPRPPPRRIYPQPRPPHPRL-NH$_2$ | 4 | 4 |
| 50 | A51 B1 | VDKPPYLPRPRPPPRRIYNO-NH$_2$ | 8 | 16 |
| 51* | A51 B2 | VDKPPYLPRPRPPPRRIYNN-NH$_2$ | 16 | 64 |
| 52* | A51 B3 | VDKPPYLPRPRPPPRRIYNDap(Ac)-NH$_2$ | 32 | 64 |
| 53 | A56 E1 | VDKPPYLPRPRPPPRRIYNH-NH$_2$ | 16 | 16 |
| 54 | A59 A2 | VDKPPYLPRPRPPPRRIYNAgp-NH$_2$ | 8 | 8 |
| 55 | A59 A3 | VDKPPYLPRPRPPPRRIYNArg(NO$_2$)-NH$_2$ | 8 | 16 |
| 56 | A59 A4 | VDKPPYLPRPRPPPRRIYN(N—Me-Arg)-NH$_2$ | 8 | 4 |
| 57 | A59 A5 | VDKPPYLPRPRPPPRRIYNHar-NH$_2$ | 8 | 8 |
| 58 | A66 D2 propyl. | VDKPPYLPRPRPPPRRIYNR-NHC$_3$H$_7$ | 4 | 8 |
| 59 | A45 A6 | VDKPPYLPRPRPPRPRIYNR-NH$_2$ | 8 | 16 |
| 60* | A45 A5 | VDKPPYLPRPRPPRPIYNR-NH$_2$ | 8 | 64 |
| 61 | A45 A3 | VDKPPYLPRPRPPPROIYNR-NH$_2$ | 8 | 16 |

TABLE 7-continued

Antimicrobial activity against *E. coli* BL21
AI and *M. luteus* 10240. Minimum inhibitory concentration
(MIC) determined in 1% TSB.

| SEQ ID NO. | Synthesis number | Sequence | *E. coli* BL21 AI | *M. luteus* 10240 |
|---|---|---|---|---|
| 62 | A51 B4 | VDKPPYLPRPRPPRbetaHArgIYNR-NH$_2$ | 4 | 16 |
| 63 | A53 F1 | VDKPPYLPRPRPPR-4tHyp-IYNO-NH$_2$ | 4 | 8 |
| 64 | A66 C5 | VDKPPYLPRPRPPRHIYNH-NH$_2$ | 8 | 32 |
| 65 | A70 B4 | VDKPPYLPRPRPPRAgpIYNHar-NH$_2$ | 4 | 2 |
| 66 | A70 C1 | VDKPPYLPRPRPPRAgpIYNAgp-NH$_2$ | 8 | 4 |
| 67 | A70 B5 | VDKPPYLPRPRPPRHarIYNHar-NH$_2$ | 4 | 4 |
| 68 | A70 C2 | VDKPPYLPRPRPPRHarIYNAgp-NH$_2$ | 4 | 4 |
| 69 | A70 C3 | VDKPPYLPRPRPPROIYNAgp-NH$_2$ | 4 | 4 |
| 70 | A70 B6 | VDKPPYLPRPRPPROIYNHar-NH$_2$ | 4 | 4 |
| 71 | A66 D3 propyl. | VDKPPYLPRPRPPROIYNR-NHC$_3$H$_7$ | 4 | 8 |
| 72 | A53 F2 | VDKPPYLPRPRPPROIYNO-NH$_2$ | 8 | 8 |
| 73 | A66 C6 | VDKPPYLPRPRPPROLYNO-NH$_2$ | 8 | 16 |
| 74 | A66 D1 | VDKPPYLPRPRPPROIYQO-NH$_2$ | 4 | 8 |
| 75 | A56 D2 | VEKPPYLPRPRPPRRIYNR-NH$_2$ | 16 | 8 |
| 76 | A56 D3 | VDRPPYLPRPRPPRRIYNR-NH$_2$ | 16 | 8 |
| 77 | A56 D4 | VDKPPYIPRPRPPRRIYNR-NH$_2$ | 32 | 8 |
| 78 | A56 D5 | VDKPPYLPRPRPPRRLYNR-NH$_2$ | 8 | 16 |
| 79 | A56 D6 | VDKPPYLPRPRPPRRIYQR-NH$_2$ | 8 | 8 |
| 80 | A32 D3 ac. | Ac-VDKPPYLPRPRPPRRIYNR-OH | >256 | 16 |
| 81 | A32 D3 fo. | For-VDKPPYLPRPRPPRRIYNR-OH | 128 | 32 |
| 82 | A45 A2 | ODKPPYLPRPRPPRRIYNR-NH$_2$ | 8 | 8 |
| 83 | A45 A2 ac. | Ac-ODKPPYLPRPRPPRRIYNR-NH$_2$ | 16 | 16 |
| 84 | A45 A4 guan. | Guan-VDKPPYLPRPRPPRRIYNR-NH$_2$ | 32 | n.d. |
| 85 | A62 B3 guan. | Guan-VDKPPYLPRPRPPROIYNO-NH$_2$ | 64 | n.d. |
| 86* | A35 A5 | DKPPYLPRPRPPRRIYNR-NH$_2$ | 32 | 8 |
| 87* | A54 E1 | GNNRPVYIPQPRPPHPRL-OH | 2 | 64 |
| 89* | A34 B3 | GKPRPYSPRPTSHPRPIRV-OH | 4 | 0.5 |
| 91* | A35 A1 | VDKGSYLPRPTPPRPIYNRN-NH$_2$ | 16 | 128 |
| 95 | A60 E4 F5 | RQIKIWFQNRRMKWKKC(CH$_2$CO-GNNRPVYIPQPRPPHPRL-OH)-OH | 8 | 8 |
| 97 | A60 E2 F5 | RQIKIWFQNRRMKWKKC(CH$_2$CO-GKPRPYSPRPTSHPRPIRV-OH)-OH | 16 | 1 |
| 99 | A60 E6 F5 | RQIKIWFQNRRMKWKKC(CH$_2$CO-VDKGSYLPRPTPPRPIYNRN-NH$_2$)-OH | 32 | 4 |
| 101 | A60 F2 F5 | RQIKIWFQNRRMKWKKC(CH$_2$CO-VDKPPYLPRPRPPRRIYNR)-NH$_2$)-OH | 32 | 4 |
| 103* | A60 F5 | (RQIKIWFQNRRMKWKKC-OH)$_2$ | >128 | >128 |
| 107 | A74 C6 | VDKPPYLPRPRP-4tHyp-ROIYNO-NH$_2$ | 4 | 4 |

TABLE 7-continued

Antimicrobial activity against *E. coli* BL21 A1 and *M. luteus* 10240. Minimum inhibitory concentration (MIC) determined in 1% TSB.

| SEQ ID NO. | Synthesis number | Sequence | *E. coli* BL21 AI | *M. luteus* 10240 |
|---|---|---|---|---|
| 108 | A74 D1 | VDKPPYLPRPRP-4tHyp-R-4tHyp-IYNO-NH$_2$ | 2 | 32 |
| 109 | A76 B3 | VDKPPYLPRPRPPRO-Tle-YNO-NH$_2$ | 4 | 4 |
| 110 | A76 B5 | VDKPPYLPRPRP-4tHyp-R-4tHyp-Tle-YNO-NH$_2$ | 2 | 16 |
| 111 | T1 D9 | VDKPPYLPRPRPPRrIYNR-NH$_2$ | 4 | 4 |
| 112 | T1 D11 | VDKPPYLPRPRPPRrIYNr-NH$_2$ | 4 | n.d. |
| 113 | A82 A4 | ONYIORPPRPRPLYPPKDV-NH$_2$ | >256 | 64 |
| 114 | A82 A5 | ONYI-4tHyp-RPPRPRPLYPPKDV-NH$_2$ | >256 | 128 |
| 115 | T1 C7 | vdkppylprprpprriynr-NH$_2$ | 64 | 16 |
| 116 | T1 C9 | vdkppylprprpproiyno-NH$_2$ | 64 | 32 |
| 117 | T1 C11 | rnyirrpprprplyppkdv-NH$_2$ | 64 | 32 |
| 118 | T1 D1 | onyiorpprprplyppkdv-NH$_2$ | 256 | 32 |

Propyl stands for a propylamide on the C-terminus (Sub$_2$=OR$_3$=NHC$_3$H$_7$); Ac=acetyl group, for=formyl group, guan=guanidino group and CF=5,6-carboxyfluorescein are examples of modified N-termini (modified alpha-amino group of the N-terminal amino acid, Sub$_1$=acetyl-NH, formyl-NH, guanidine or 5,6-carboxyfluorescein), βHar: β-homoarginine, the beta-amino acid homolog to arginine, Agp: 2-amino-3-guanidinopropionic acid, Har: homoarginine and Arg(NO$_2$): nitroarginine are homologs of arginine, N-Me-Arg: N-methyl-arginine—an arginine methylated at the peptide bond, 4tHyp: trans-4-hydroxyproline, Tle: tert-butylglycine Dap(Ac): 2,3-diaminopropionic acid with acetylated amino function in the side chain, (CH$_2$CO): acetyl linker on SH group of cysteine, f: α-aminocaproic acid, lower-case letters stand for the corresponding D-amino acids.

SEQ ID NO. 2 corresponds to the native Oncopeltus 4 sequence. SEQ ID NO. 1 is an N-terminally shortened derivative of the native Oncopeltus 4 sequence. The sequences with SEQ ID NO. 1, 2, 3, 4, 10 to 13, 17, 28, 31, 34, 35, 39 and 48 are comparative examples, these and others are marked with * in Table 7. The sequences with SEQ ID NO. 8 to 9, 80, 81 and 85 are less preferred examples of the invention. The other sequences shown in Table 7 are peptides or peptide derivatives preferred according to the invention. The examples most preferred are SEQ ID NO. 18, 22, 24, 26, 29, 58, 62, 63, 65 to 71, 74, 79, 82 and 107 to 112.

By exchanging ProII (residue X$_2$) in the initial sequence (SEQ ID NO. 2) for the cationic amino acids Lys and Arg (SEQ ID NO. 8 and 14), surprisingly, higher activity against *E. coli* BL21 AI and *M. luteus* 10240 was achieved. Exchange for His (SEQ ID NO. 5) and a Thr frequently occurring at this position in proline-rich AMP (SEQ ID NO. 4) did not have a positive effect. The derivative with Arg at position 11 had, at 8 μg/mL (*E. coli*), the lowest MIC so far and was accordingly altered C-terminally. Amidation of the C-terminus only altered the activity against *M. luteus* negatively by one dilution step. Peptide derivatives without Arg and thus lacking a positive charge at the last or penultimate position (SEQ ID NO. 27, 28, 47, 51) lost activity by a factor of 8 to 16, mainly against *M. luteus* and are not included among the preferred examples.

SEQ ID NO. 16 with Arg at position 19 (residue X$_4$) and Asn at 20 was as active as SEQ ID NO. 14. Unexpectedly, amidation of the C-terminus (Sub$_2$) does not have a negative influence on the activity (SEQ ID NO. 15). Amidation of the C-terminus (Sub$_2$) even leads to increased activity (cf. SEQ ID NO. 18 with SEQ ID NO. 19). C-terminal amidation has in addition a significantly positive effect on stability. Thus, amidated peptide derivatives have an up to 30 min longer half-life than the corresponding peptide with free acid function (example 2). The peptide derivative SEQ ID NO. 18 had, at 4 or 8 μg/mL against *E. coli* or *M. luteus* respectively, the lowest MIC values, at a half-life of 60 min in 25% aqueous mouse serum and was designated as oncocin (Table 4).

In the serum stability test, oncocin was cleaved C-terminally at position 15 (residue X$_3$) and 19 (residue X$_4$) and the peptides VDKPPYLPRPRPPR-OH (corresponds to SEQ ID NO. 126) and VDPPYLPRPRPPRRIYN-OH (corresponds to SEQ ID NO. 28) were identified as the main degradation products. The derivative shortened by Arg19, with a MIC of 64 μg/mL, still only had very low antimicrobial activity against *E. coli*. Derivatives with arginine or other cationic amino acids at position 19 (residue X$_4$) showed, surprisingly, increased stability. However, a derivative with His at position 19 (residue X$_4$; SEQ ID NO. 53) with a MIC of 16 μg/mL against *E. coli* had 4 times lower activity than oncocin. Preferred examples are substitutions with Agp, Arg(NO$_2$), N-Me-Arg and Har (SEQ ID NO. 54 to 57) at position 19 (residue X$_4$) substituted peptide derivatives whose MIC values correspond to the values of oncocin and therefore unexpectedly do not have a negative influence on the activity of the peptides. The preferred, least expensive example was the substitution of Arg19 for ornithine in SEQ ID NO. 50. This derivative is far more stable than oncocin (60 min) at almost the same activity. Another preferred example for stabilization of the C-terminus was amidation of the carboxyl function ($Sub_2$) as propylamide (SEQ ID NO. 58). The antimicrobial activity is maintained and the half-life is also more than 120 min.

In the derivatives stabilized at position 19 (residue $X_4$), in further examples position 15 (residue $X_3$) was substituted with arginine derivatives or other cationic amino acids. Preferred examples are SEQ ID NO. 65 to 70, with various combinations of Agp, Arg($NO_2$), N-Me-Arg, Har and Orn. The most cost-effective preferred example is SEQ ID NO. 72, with ornithine at position 15 and 19 (residue $X_3$ and $X_4$) and a half-life of more than 360 min, with activity comparable to oncocin (MIC 8 µg/mL E. coli). SEQ ID NO. 74 had, additionally to Orn15 and Orn16, a substitution of glutamine at position 18 for asparagine, which resulted in slightly higher activity (MIC 4 µg/mL E. coli). The combination of Orn at position 15 (residue $X_3$) and amidation of the C-terminus ($Sub_2$) with propylamine in SEQ ID NO. 71 is another much preferred example with surprisingly high activity (4 µg/mL E. coli) and very high serum stability (>360 min). A noncationic substitution at position 15 (residue $X_3$) with hydroxyproline was carried out in the preferred SEQ ID NO. 63 in combination with Orn at position 19 (residue $X_4$). This derivative also has high activity (4 µg/mL E. coli, 8 µg/mL M. luteus) and excellent stability (>360 min). Substitution of the proline in position 4, 8 or 13 (SEQ ID NO. 21 to 24) of oncocin with hydroxyproline has no effect on the MIC values, and does not reduce the protease resistance of the second labile cleavage site at position 15 (residue $X_3$). Although this exchange with hydroxyproline has neither an effect on the MIC values nor an effect on serum stability, unexpectedly this exchange reduces cellular toxicity and hemolysis.

A preferred example for modification of the N-terminus in oncocin is SEQ ID NO. 82 with substitution of position 1 (residue $X_1$) in Orn, with the same activity against oncocin. Acetylation, methanoylation (formylation) or guanidation of the N-terminal amino function ($Sub_1$; SEQ ID NO. 80, 81, 83, 84, 85) reduced the activity to e.g. 128 µg/mL or 32. (E. coli or M. luteus; SEQ ID NO. 81).

Penetratin was coupled via a thioether bridge to the amino function of the N-termini of the antimicrobial peptides. This modification was able to extend the activity spectrum of the peptides with up to now little activity against M. luteus, to include this bacterium. The MIC value for pyrrhocoricin (SEQ ID NO. 91) was reduced to the greatest extent from 128 µg/mL to 4 µg/mL for penetratin-pyrrhocoricin (SEQ ID NO. 98), which is equivalent to a 32-fold increase in activity. Penetratin-apidaecin (8 µg/mL, SEQ ID NO. 94) was also 8 times more active than the unmodified apidaecin 1b (64 µg/mL SEQ ID NO. 87). For oncocin (SEQ ID NO. 18) with a MIC value of 8 µg/mL, still a 2-fold increase in activity to 4 µg/mL was observed for penetratin-oncocin (SEQ ID NO. 100). The high activity of drosocin (0.5 µg/mL, SEQ ID NO. 89) was maintained in the pentetratin-drosocin construct (1 µg/mL, SEQ ID NO. 96).

The exchange of proline at position 13 and 15 for trans-4-hydroxyproline and Arg19 for ornithine (SEQ ID NO. 108) leads surprisingly, at 2 µg/mL, to an increase in activity against E. coli compared with the native oncocin sequence (4 µg/ml, SEQ ID NO. 18) while the stability remains high. If the isoleucine at position 16 is replaced with tert-butylglycine (SEQ ID NO. 110), the MIC value of 2 µg/mL against E. coli is maintained. It is mainly the increased stability that is of interest here.

The activity of the peptide with SEQ ID NO. 107 shows the same antibiotic action against M. Luteus as oncocin (SEQ ID NO. 18). The sequences SEQ ID NO. 113 to 118 are comparative examples. The derivatives synthesized with D-amino acids (SEQ ID NO. 115 and 116) show no activity against E. coli and only slight activity against M. luteus (64 or 128 µg/mL).

Both the all D-peptides with D-amino acids in the native order (SEQ ID NO. 115 and 116) and the retro-inverse synthesized peptides (SEQ ID NO. 117 and 118) show only slight activity against E. coli (64-256 µg/mL). However, all peptides synthesized with D-amino acids (SEQ ID NO. 115 to 118) still display, with MIC values between 16-32 µg/mL, relatively good activity against M. luteus, which is located in the region of the L-peptides with five positive net charges. The net charge-dependent activity and the MIC values of the D-peptides against M. luteus might indicate a target protein-nonspecific mechanism of action in this Gram-positive bacterium.

TABLE 8

Antimicrobial activity against pathogenic Escherichia coli DSM 10233, Klebsiella pneumoniae DSM 681 and Pseudomonas aeruginosa DSM 3227. Minimum inhibitory concentration (MIC) determined in 1% TSB.

| SEQ ID NO. | Sequence | E. coli DSM 10233 | K. pneumoniae DSM 681 | P. aeruginosa DSM 3227 |
|---|---|---|---|---|
| 18 | VDKPPYLPRPRPPRRIYNR-$NH_2$ | 16 | 4 | >32 |
| 72 | VDKPPYLPRPRPPROIYNO-$NH_2$ | 32 | 4 | >32 |
| 63 | VDKPPYLPRPRPPR-4tHyp-IYNO-$NH_2$ | 1 | 2 | 16-32 |
| 107 | VDKPPYLPRPRP-4tHyp-ROIYNO-$NH_2$ | 16 | 4 | >32 |
| 108 | VDKPPYLPRPRP-4tHyp-R-4tHyp-IYNO-$NH_2$ | 1 | 2 | 16-32 |
| 111 | VDKPPYLPRPRPPRrIYNR-$NH_2$ | 4 | 4 | n.d. |
| 117 | rnyirrpprprplyppkdv-$NH_2$ | >32 | >32 | n.d. |

The peptides shown in Table 8 were investigated for their MIC against pathogenic bacteria such as E. coli DSM 10233, K. pneumoniae DSM 681 and P. aeruginosa DSM 3227. Ml derivatives with 4-trans-hydroxyproline at position 15 (SEQ ID NO. 63, 108, 113 and 114) have, with MIC values between 1-4 µg/mL, surprisingly up to 16 times higher activity against E. coli DSM 10233 than oncocin (SEQ ID NO. 18).

Table 10 gives the MIC values of some peptides and peptide derivatives against multiresistant bacterial strains. The tests were in this case carried out in Mueller-Hinton medium (¼ concentrated), which is equivalent to 1% TSB. Some of the resistant bacterial strains tested are shown in Table 9 and the peptides tested are shown in Table 11.

TABLE 9

| Multiresistant Gram-negative bacteria tested | |
| --- | --- |
| E. coli D31 (J. Wilson) | β-lactamase overproducer (ESBL+) - resistant to β-lactamase inhibitors |

TABLE 9-continued

| Multiresistant Gram-negative bacteria tested | |
| --- | --- |
| E. coli ATCC BAA-457 | trimethoprim-sulfomethoxazole-resistant |
| E. coli 045-849 SENTRY | ciprofloxacin- and trimethoprim-sulfomethoxazole-resistant |
| K. pneumoniae ATCC 27799 | gentamicin-, cephalothin- and naladixic acid-resistant |
| K. pneumoniae ATCC 700603 | produces β-lactamase SHV-18 (ESBL+) - resistant to β-lactamase inhibitors |
| K. pneumoniae 012-3132 | fluoroquinolone-resistant |
| S. typhimurium ATCC 700408 | multi-resistant (e.g. ampicillin, chloramphenicol) |
| S. typhimurium S5 (J. Weiser) | multi-resistant (e.g. cefotaxime, tobramycin) |

TABLE 10

Antimicrobial activity against multiresistant bacteria. MIC in ¼ Muller-Hinton medium.

| SEQ ID NO. | E. coli D31 J. Wilson | E. coli SEQ 102 ATCC # BAA-457 | E. coli 045-849 SENTRY | K. pneumoniae ATCC 27799 | K. pneumoniae K6 ATCC 700603 | K. pneumoniae 012-3131 | S. typhimurium ATCC 700408 |
| --- | --- | --- | --- | --- | --- | --- | --- |
| 87* | 1 | 1 | 0.5 | 4 | 16 | 16 | 0.13 |
| 89* | 4 | 2 | 2 | 8 | 8 | 4 | 0.5 |
| 18 | 2 | 4 | 4 | 16 | 8 | 4 | 0.25 |
| 24 | 1 | 4 | 2 | 8 | 8 | 2 | 0.13 |
| 15 | 16 | 32 | 4 | 64 | 32 | 16 | 0.5 |
| 22 | 2 | 4 | 4 | 16 | 8 | 4 | 0.5 |
| 14 | 32 | 64 | 4 | 128 | 64 | 32 | n.d |
| 20 | 4 | 32 | 8 | 64 | 128 | 64 | n.d |
| 23 | 8 | 32 | 8 | 64 | 32 | 16 | n.d |
| 21 | 32 | 64 | 16 | 128 | 64 | 32 | n.d |
| 16 | 32 | 32 | 4 | 128 | 64 | 32 | n.d |
| 5 | 64 | 128 | 16 | 128 | 128 | 64 | n.d |

| SEQ ID NO. | S. typhimurium s5 (J. Weiser) | S. typhimurium ATCC 14028 | P. mirabilis ATCC 7002 | P. vulgaris ATCC 6896 | P. aeruginosa 39324 | P. aeruginosa 10 J. Wilson | S. saprophyticus 15305 |
| --- | --- | --- | --- | --- | --- | --- | --- |
| 87* | 0.5 | 0.5 | > | > | 64 | 32 | > |
| 89* | 1 | 8 | > | > | 32 | 16 | >64 |
| 18 | 4 | 2 | 128 | 128 | 4 | 8 | 16 |
| 24 | 2 | 2 | 128 | 128 | 4 | 2 | 16 |
| 15 | 8 | 4 | > | > | n.d | 16 | n.d |
| 22 | 8 | 2 | 128 | 128 | n.d | 16 | n.d |
| 14 | n.d | n.d | n.d | n.d | n.d | n.d | n.d |
| 20 | n.d | n.d | n.d | n.d | n.d | n.d | n.d |
| 23 | n.d | n.d | n.d | n.d | n.d | n.d | n.d |
| 21 | n.d | n.d | n.d | n.d | n.d | n.d | n.d |
| 16 | n.d | n.d | n.d | n.d | n.d | n.d | n.d |
| 5 | n.d | n.d | n.d | n.d | n.d | n.d | n.d | n.d: not determined

*apidaecin 1b (SEQ ID NO. 87) and drosocin (SEQ ID NO. 89) for comparison.

TABLE 11

Sequences tested

| SEQ ID NO. | Sequence |
|---|---|
| 87 | GNNRPVYIPQPRPPHPRL-OH |
| 89 | GKPRPYSPRPTSHPRPIRV-OH |
| 18 | VDKPPYLPRPRPPRRIYNR-NH$_2$ |
| 24 | VDKPPYLPRPRP-4tHyp-RRIYNR-NH$_2$ |

TABLE 11

Antimicrobial activity against pathogenic *Escherichia coli* DSM 10233, *Klebsiella pneumoniae* DSM 681 and *Pseudomonas aeruginosa* DSM 3227. Minimum inhibitory concentration (MIC) determined in 1% TSB.

| SEQ ID NO. | Sequence | E. coli | K. pneumoniae DSM 681 | P. aeruginosa DSM 3227 |
|---|---|---|---|---|
| 18 | VDKPPYLPRPRPPRRIYNR-NH$_2$ | 16 | 4 | >32 |
| 72 | VDKPPYLPRPRPPROIYNO-NH$_2$ | 32 | 4 | >32 |
| 63 | VDKPPYLPRPRPPR-4tHyp-IYNO-NH$_2$ | 1 | 2 | 16-32 |
| 107 | VDKPPYLPRPRP-4tHyp-ROIYNO-NH$_2$ | 16 | 4 | >32 |
| 108 | VDKPPYLPRPRP-4tHyp-R-4tHyp-IYNO-NH$_2$ | 1 | 2 | 16-32 |
| 111 | VDKPPYLPRPRPPRrIYNR-NH$_2$ | 4 | 4 | n.d. |
| 117 | rnyirrpprprplyppkdv-NH$_2$ | >32 | >32 | n.d. |

TABLE 11-continued

Sequences tested

| SEQ ID NO. | Sequence |
|---|---|
| 15 | VDKPPYLPRPRPPRRIYNNR-NH$_2$ |
| 22 | VDKPPYL-4tHyp-RPRPPRRIYNR-NH$_2$ |
| 14 | VDKPPYLPRPRPPRRIYNNR-OH |
| 20 | VDKPPYLPRPRPPRPIYNR-OH |
| 23 | VDK-4tHyp-PYLPRPRPPRRIYNR-OH |
| 21 | VDKPPYL-4tHyp-RPRPPRRIYNR-OH |
| 16 | VDKPPYLPRPRPPRRIYNRN-OH |
| 5 | VDKPPYLPRPKPPRRIYNNR-OH |

The preferred examples SEQ ID NO. 18, 22 and 24 showed, surprisingly, an at least as high or higher activity against the three different Gram-negative multiresistant bacterial species *E. coli, Klebsiella pneumoniae* and *Salmonella typhimurium*. Oncocin (SEQ ID NO. 18) had MIC values of 2 µg/mL against β-lactamase-overproducing *E. coli* D31, 4 µg/mL against fluoroquinolone-resistant *K. pneumoniae* 012-3132 and 0.25 µg/mL against multiresistant *S. typhimurium* ATCC 700408 bacteria. With one exception (SEQ ID NO. 15), all the amidated peptides tested showed good MIC values against the *E. coli* and *K. pneumoniae* strains. Deletion of Asn19 from SEQ ID NO. 2, which leads to oncocin (SEQ ID NO. 18), surprisingly increased the activity of the peptides further. Amidation of the C-terminus not only increases the activity against *E. coli* and *K. pneumoniae*, but in addition increases the stability of the Oncopeltus 4 or oncocin derivatives.

With *Pseudomonas aeruginosa, Proteus mirabilis* and *Proteus vulgaris*, further Gram-negative bacteria were tested and the activity of the preferred examples SEQ ID NO. 18 and 24 was determined. Oncocin (SEQ ID NO. 18) was active both against *P. aeruginosa* 39324 (MIC 4 µg/mL) and against *P. mirabilis* and *P. vulgaris* (128 µg/mL). Oncocin was also active, at 16 µg/mL, against Gram-positive *Staphylococcus saprophyticus* 15305 bacteria. Therefore the peptides according to the invention display a surprisingly broad spectrum of action.

Derivatives of oncocin show very good activity against pathogenic bacteria such as *E. coli* DSM 10233, *K. pneumoniae* DSM 681 and *P. aeruginosa* DSM 3227. Substitution with 4-trans-hydroxyproline at position 15 (SEQ ID NO. 63 and 108) leads to surprisingly high MIC values against *E. coli* DSM 10233 between 1-4 µg/mL, these are 16 times higher than for oncocin (SEQ ID NO. 18). These derivatives also display high activity against *K. pneumoniae* DSM 681 and *P. aeruginosa* DSM 3227, illustrating the broad spectrum of action of the peptides according to the invention.

Example 4

Fluorescence Microscopy

HeLa and SH-SY5Y cells were plated out in 96-well microtiter plates (Greiner Bio-One GmbH, Frickenhausen, Germany) and incubated overnight. On the next day, 5,6-carboxyfluorescein-labeled peptides or penetratin constructs were dissolved in fresh medium (40 µmol/L) and the cells were incubated therein for 2 h. The cells were washed twice with PBS and were investigated in PBS by fluorescence microscopy.

Parameters for Fluorescence Microscopy
Microscope: Leica DMI6000B (Leica Mikrosystems GmbH, Wetzlar, Germany)
Light source: Leica EL6000 with metal-halogen lamp
Objective: N PLAN L 20×0.40 corr
Software: Leica Application Suite 2.1.8.; Adobe Photoshop CS The fluorescence micrographs in FIG. 3 show that after incubation with 40 µmol/L 5,6-carboxyfluorescein-labeled oncocin (SEQ ID NO. 94), fluorescence is not detectable in HeLa or in SH-SY5Y cells (FIGS. 3B and F). Moreover, no fluorescence and therefore no internalization of these antimicrobial proline-rich peptides could be detected for 5,6-carboxyfluorescein-labeled apidaecin 1b, pyrrhocoricin and drosocin (SEQ ID NO. 88, 90 and 92). In contrast, after incubation of both cell lines with 5,6-carboxyfluorescein-labeled penetratin-oncocin (SEQ ID NO. 102), strong fluorescence in the cell interior was observed in the micrographs (FIGS. 3D and E), providing evidence of internalization of the whole construct.

The penetratin constructs with apidaecin 1b, pyrrhocoricin and drosocin (SEQ ID NO. 96, 98 and 100) also internalize in both cell lines and show definite fluorescence.

Example 5

Confocal Laser Scanning Microscopy

Bacteria

A bacterial suspension that had been cultured overnight was diluted to $150 \times 10^6$ cells/mL and the 5,6-carboxyfluorescein-labeled peptides and penetratin constructs were added (final concentration of 30 µmol/L). In order to quench the fluorescence of the molecules outside of the bacteria, 60 eq of 5,6-carboxytetramethylrhodamine (TAMRA; Merck, Darmstadt, Germany) was added. The fluorescence resulting from internalization of the labeled peptides in the bacteria was investigated immediately with a TCS SP5 confocal laser scanning microscope from the company Leica Microsystems GmbH (Wetzlar, Germany).

After incubation for 20 min with 5,6-carboxyfluorescein-labeled oncocin, the peptide had accumulated in the bacterial membrane (FIG. 4B). The quenching effect through fluorescence resonance energy transfer (FRET) between 5,6-carboxyfluorescein and TAMRA, which remains outside the cell, is therefore lost and a fluorescence signal can be detected. After a further 30 min, the peptide had accumulated inside the cell (FIG. 4D). The 5,6-carboxyfluorescein-labeled apidaecin 1b, pyrrhocoricin and drosocin sequences (SEQ ID NO. 96, 98 and 100) also internalize in E. coli and produce a definite fluorescence. In contrast, the labeled penetratin constructs reach the interior of the cell more slowly and cause much weaker fluorescence after comparable incubation times (FIG. 4F). This observation correlates with the minimum inhibitory concentrations determined. Thus, the penetratin construct of oncocin (SEQ ID NO. 100) had, at 32 µg/mL, an 8 times higher MIC value than oncocin (4 µg/mL; SEQ ID NO. 18) and thus considerably lower activity against E. coli (Table 7). Entry of the penetratin homodimer could not be detected by fluorescence microscopy even after 90 min (FIG. 4H). This shows that in the penetratin construct, the respective proline-rich peptide sequence transports penetratin as cargo into the bacterial cell.

In contrast, the 5,6-carboxyfluorescein-labeled penetratin homodimer enters Gram-positive M. luteus cells and produces a definite fluorescence signal there after incubation for 1 h (FIG. 5J). The labeled pyrrhocoricin cannot be detected in M. luteus after the same incubation time (FIG. 5B). With penetratin as transporter in the labeled penetratin-pyrrhocoricin, the derivative accumulates in M. luteus and produces a strong fluorescence signal (FIG. D). The MIC value drops from 128 µg/ml for pyrrhocoricin to 4 µg/mL for penetratin-pyrrhocoricin, which corresponds to a 32-fold increase in activity (Table 7). In parallel, an 8-fold increase in activity for apidaecin 1b (64 µg/mL) was determined in the penetratin-apidaecin derivative (8 µg/mL).

HeLa and SH-SY5Y Cells

The cells were cultured on glass-bottomed culture dishes from the company MatTek Corporation (Ashland, Mass., USA) and were incubated with 5,6-carboxyfluorescein-labeled penetratin constructs (10 µmol/L for SH-SY5Y or 7 µmol/L for HeLa) for 2 h or 24 h. The medium was removed, washed twice with PBS and fresh medium was added. For staining the cell nucleus, the dye Hoechst 33342 (Fluka Chemie GmbH, Buchs, Switzerland) was added and it was incubated for a further 15 min. The fluorescence was analyzed immediately with the TCS SP5 confocal laser scanning microscope. All images were recorded in a sequential scan mode and the batch of images was analyzed with the Leica Application Suite Advanced Fluorescence 1.7.1 software (Leica Microsystems) and Adobe Photoshop CS (Adobe Systems GmbH, Munich, Germany).

The results show that the antimicrobial peptides, which had been extended N-terminally by 5,6-carboxyfluorescein-penetratin, penetrate into the cells within 2 hours. Conversely, the antimicrobial peptides only labeled with 5,6-carboxyfluorescein, without the penetratin sequence, could not be detected in the cells, i.e. these peptides cannot penetrate through the external cell membrane into the tested cell lines. Transport into the interior of the cell only takes place via the penetratin sequence. Staining of the cell nuclei with the dye Hoechst 33342 and of the mitochondria with the dye MitoTracker Red CMXRos ruled out localization of the peptides in these compartments. After quite a long incubation time (24 h) the fluorescence employed by the 5,6-carboxyfluorescein was concentrated near the cell nucleus. By staining the Golgi body, partial co-localization could be detected.

Example 6

Cytotoxicity

MTT Assays with HeLa and SH-SY5Y Cells

The cytotoxicity of the peptides, peptidomimetics and penetratin constructs was determined with the "Cell Proliferation Kit I" from the company Roche Diagnostics GmbH (Mannheim, Germany). The method is based on reduction of the yellow methylthiazolyldiphenyl tetrazolium bromide (MTT) by cellular oxidoreductases of metabolically active cells (Vistica D T et al. Tetrazolium-Based Assays for Cellular Viability—A Critical Examination of Selected Parameters Affecting Formazan Production. *Cancer Research* 51: 2515-20, 1991; Slater T F, Sawyer B, & Strauli U. Studies on Succinate-Tetrazolium Reductase Systems. 3. Points of Coupling of 4 Different Tetrazolium Salts. *Biochimica et Biophysica Acta* 11: 383-&, 1963; Berridge M V & Tan A S. Characterization of the Cellular Reduction of 3-(4,5-Dimethylthiazol-2-yl)-2,5-diphenyltetrazolium bromide (Mtt)—Subcellular Localization, Substrate Dependence, and Involvement of Mitochondrial Electron Transport in Mtt Reduction. *Archives of Biochemistry and Biophysics* 303: 474-82, 1993). The formation of the water-insoluble purple-colored formazan product is proportional to the number of viable cells and can be detected photometrically after cell lysis.

Cell culture was carried out in cell culture bottles (25 cm$^2$) with a filter cap or in 96-well microtiter plates (Greiner Bio-One GmbH, Frickenhausen, Germany) at 37° C. under 5% $CO_2$ and 95% air humidity. All media and additives were obtained from PAA Laboratories (Pasching, Austria). In each case 1% of nonessential amino acids and 1% of penicillin/streptomycin were added to MEM/glutamine medium with 5% fetal calf serum (HeLa) or DMEM/HAM's F-12 medium with 15% fetal calf serum (SH-SY5Y).

HeLa or SH-SY5Y cells were plated out in sterile 96-well microtiter plates with a concentration of $2\times10^4$ cells/well and were incubated overnight. The cells were washed once with sterile PBS and the peptides, dissolved in 100 µL fresh medium, were added. 12% PBS or 12% DMSO in medium served as negative or positive control, respectively. After incubation (24 h), 10 µL of MTT reagent was added to give a final concentration of 0.5 mg and it was incubated at 37° C. for a further four hours. With a 10% sodium dodecylsulfate solution in 0.01 mol/L hydrochloric acid, the cells and the crystalline formazan were dissolved and the absorption was determined after 16 h at 590 and 650 nm with the Paradigm™ Microplate Reader (Beckman Coulter GmbH, Wals, Austria).

The surprising results show that none of the antimicrobial proline-rich peptides tested at 600 µg/mL has toxic effects on SH-SY5Y or HeLa cells (FIG. 6). The experiments were carried out three times independently as triple determination and the proportion of metabolically active cells was normalized to the negative control 12% PBS in medium. The results are confirmed by the fact that the fluorescence-labeled derivatives of these peptides could not be detected in the interior of these cells after an incubation time of one hour (see example 5). Interaction with extracellular target molecules or receptors in the external cell membrane could thus also be ruled out for SH-SY5Y and HeLa cells.

The cytotoxicity tests of the penetratin constructs were carried out in three independent experiments of a dilution series 50-400 µg/mL as triple determination. The penetratin monomer (SEQ ID NO. 105) and a penetratin-tau sequence, which served as control, showed no toxic action against HeLa cells up to the highest concentration of 400 µg/mL (FIG. 6). With the penetratin constructs with antimicrobial peptides, negligibly small toxic effects were observed between 100 and 400 µg/mL. The penetratin homodimer (SEQ ID NO. 103) was almost 100% toxic at 400 µg/mL, whereas penetratin-drosocin and penetratin-oncocin (SEQ ID NO. 97 and 101) displayed slight toxicities. In the investigations with SH-SY5Y cells, at 400 µg/mL the penetratin monomer and the penetratin-tau construct reduced the proportion of growing cells to 70%. All penetratin-AMP constructs showed, surprisingly, no toxic action in the preferred concentrations.

Hemolysis Test

Another possibility for investigating the cytotoxicity of the peptides and peptide derivatives is the hemolysis test. The hemolytic activity is investigated on human erythrocytes (Ryge T S & Hansen P R. Potent antibacterial lysine-peptoid hybrids identified from a positional scanning combinatorial library. *Bioorganic & Medicinal Chemistry* 14: 4444-51, 2006), which the Leipzig University Hospital (Germany) made available as human erythrocyte concentrate in sodium chloride-adenine-glucose-mannitol buffer (stored at 4° C.). The erythrocytes were centrifuged off at 1000 g and washed three times with ten times the volume of cold phosphate-buffered saline (PBS, pH 7.4). The erythrocytes were diluted to a final concentration of 1% in PBS. One hundred microliters of erythrocyte suspension was pipetted into each V-shaped well of a 96-well polypropylene microtiter plate (Greiner Bio-One GmbH). Then 100 µL of the peptides dissolved in PBS was added to each position, to obtain a dilution series from 600 µg/mL to 4.7 µg/mL in seven dilution steps. The microtiter plate was incubated at 37° C. for 1 h and then centrifuged at 1000*g. 100 µL was taken from the supernatant, transferred to a 96-well flat-bottomed polystyrene microtiter plate (Greiner Bio-One GmbH) and the absorption was determined at 405 nm in a Sunrise microtiter plate reader (Tecan Trading AG, Mannedorf, Switzerland), to evaluate the release of the heme group. PBS or 0.1% Triton X-100® ((p-tert-octylphenoxy) polyethoxyethanol; Fluka Chemie GmbH, Buchs, Switzerland) and melittin (SIGMA-Aldrich-Laborchemikalien, Taufkirchen, Germany) were used as negative or positive controls. All hemolysis tests were carried out twice independently as double determination and the degree of hemolysis was determined from the following equation (Park Y et al. A Leu-Lys-rich antimicrobial peptide: activity and mechanism. *Biochimica et Biophysica Acta-Proteins and Proteomics* 1645: 172-82, 2003):

$$(E_{peptide}-E_{PBS})/(E_{Triton}-E_{PBS})\times 100\%\ E=\text{extinction at 405 nm}$$

None of the antimicrobial proline-rich peptides analyzed showed hemolytic activity up to a concentration of 600 µg/mL (Table 12). This means, even at the 100-fold higher concentrations than the MIC values determined, no lysis of human erythrocytes was observed. The hemolysis rates of all the peptides were, relative to Triton X-100®, only about 1%, which is within the error limits of this test. The nonionic surfactant Triton X-100® was used as positive control, as it completely disrupts red blood cells in this test setup within one hour. Melittin, the honeybee venom, has as an α-helical peptide, a strongly lytic action on biological membranes and disrupts both prokaryotic and eukaryotic cell membranes even at concentrations of 5 µg/mL. This cell test shows that the peptides and peptide derivatives can be used in high concentrations in the blood, without having side effects on human erythrocytes.

TABLE 12

Degree of hemolysis of selected antimicrobial peptides

| SEQ ID NO. | Name | Degree of hemolysis [%] at 600 µg/mL |
| --- | --- | --- |
| 18 | Oncocin | 1.5 |
| 87 | Apidaecin 1b | 1.2 |
| 89 | Drosocin | 1.1 |
|  | Melittin | 96.3 |
|  | Triton X-100 ® | 100 |

BRIEF DESCRIPTION OF THE DRAWINGS

FIG. 4 shows confocal laser scanning micrographs of *E. coli* BL21 A1. Peptide concentration 30 µmol/L; TAMRA concentration 180 µmol/L. Top row: phase contrast; bottom row: fluorescence. A, B: 20 min incubation with CF-oncocin; C, D: 50 min incubation with CF-oncocin; E, F: 50 min incubation with CF-penetratin-oncocin; G, H: 90 min incubation with CF-penetratin homodimer. Bars correspond to 5 µm.

FIG. 5 shows confocal laser scanning micrographs of *M. luteus* 10240. Peptide concentration 30 μmol/L; TAMRA concentration 180 μmol/L. Top row: phase contrast; bottom row: fluorescence. A, B: CF-pyrrhocoricin; C, D: CF-penetratin-pyrrhocoricin; E, F: CF-drosocin; G, H: CF-penetratin-drosocin; I, J: CF-penetratin homodimer. Bars correspond to 5 μm

SEQUENCE LISTING

Figure 1:
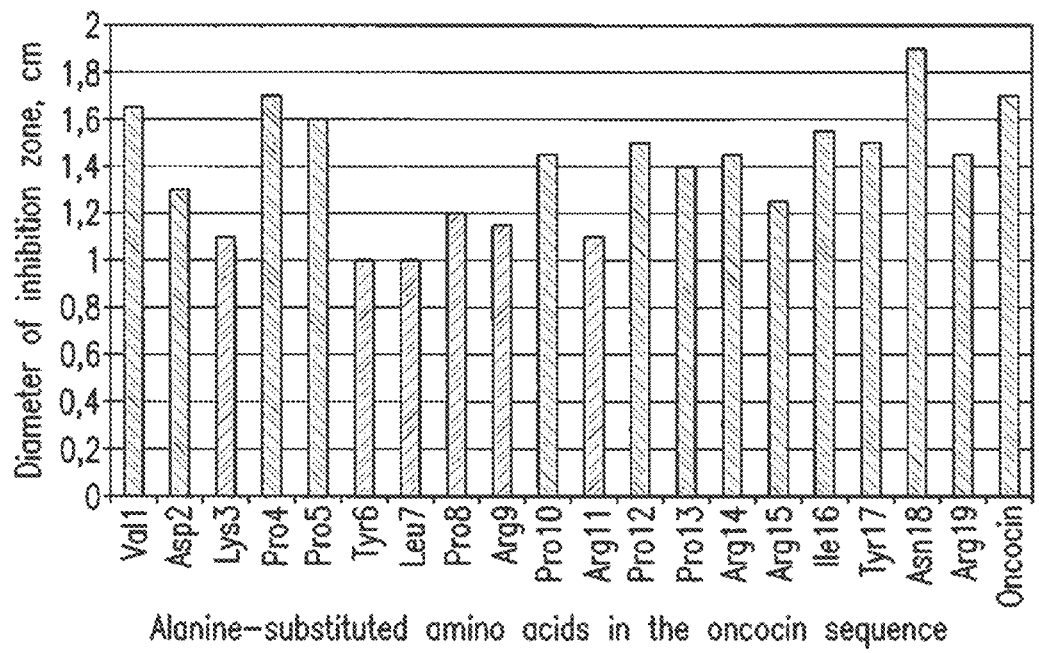
FIG. 1 shows the antibacterial activity of the oncocin analogs (Ala-Scan) against *E. coli* BL21 AI in agar diffusion assays. Cross-hatched bars indicate partial inhibition.
Figure 2:
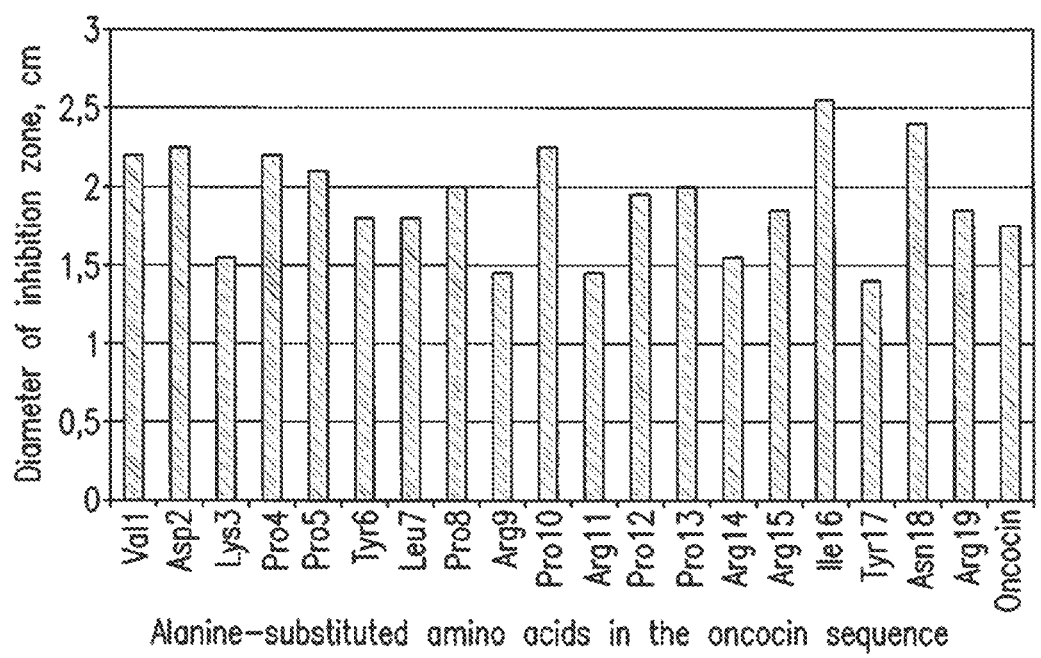
FIG. 2 shows the antibacterial activity of oncocin analogs (alanine scan) against *Micrococcus luteus* ATCC 10240 in agar diffusion assays
Figure 3A:
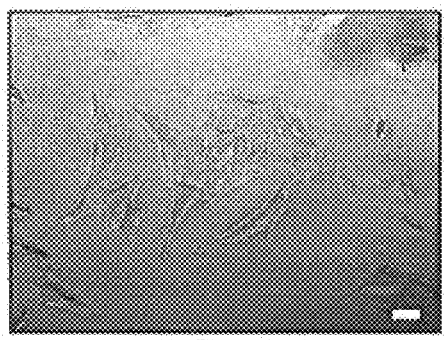
FIG. 3 shows fluorescence micrographs of HeLa and SH-SY5Y cells after incubation with 5,6-carboxyfluorescein-labeled oncocin (CF-oncocin SEQ ID NO. 94) and penetratin-oncocin (CF-penetratin-oncocin SEQ ID NO. 102). Top row: phase contrast; bottom row: fluorescence (517 nm emission). A, B: SH-SY5Y incubated with CF-oncocin; C, D: SH-SY5Y with CF-penetratin-oncocin; E, F: HeLa incubated with CF-oncocin; G, H: HeLa incubated with CF-penetratin-oncocin. Bars correspond to 20 µm.
Figure 3C:
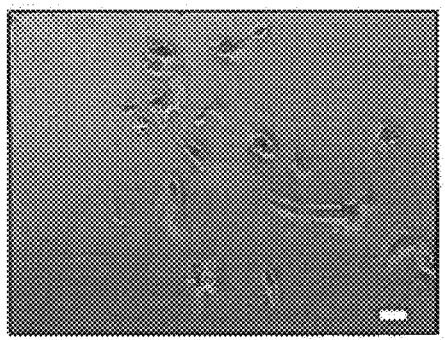
Figure 3B:
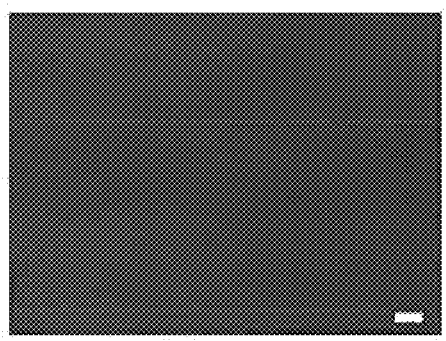
Figure 3D:
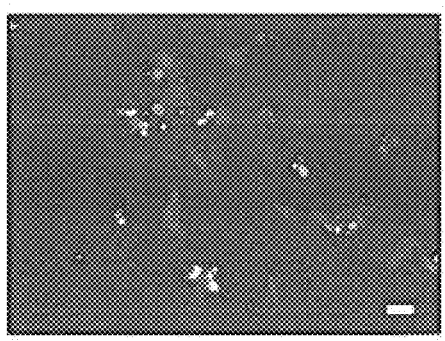
Figure 3E:
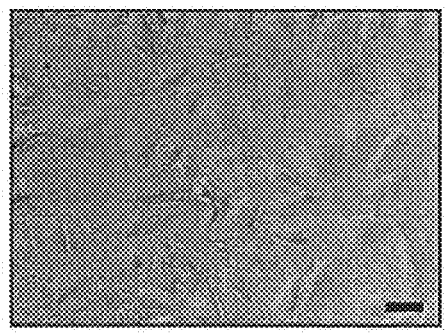
Figure 3G:
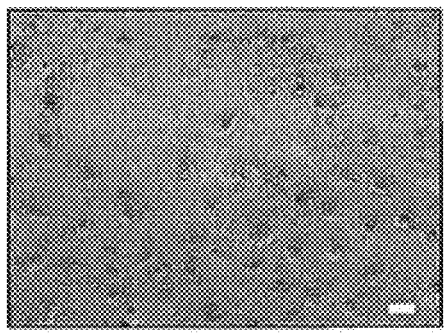
Figure 3F:
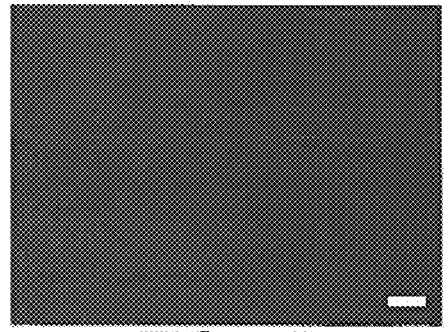
Figure 3H:
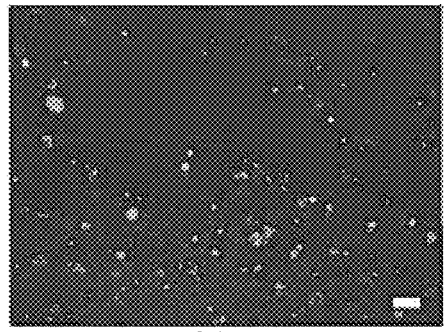
Figure 6:
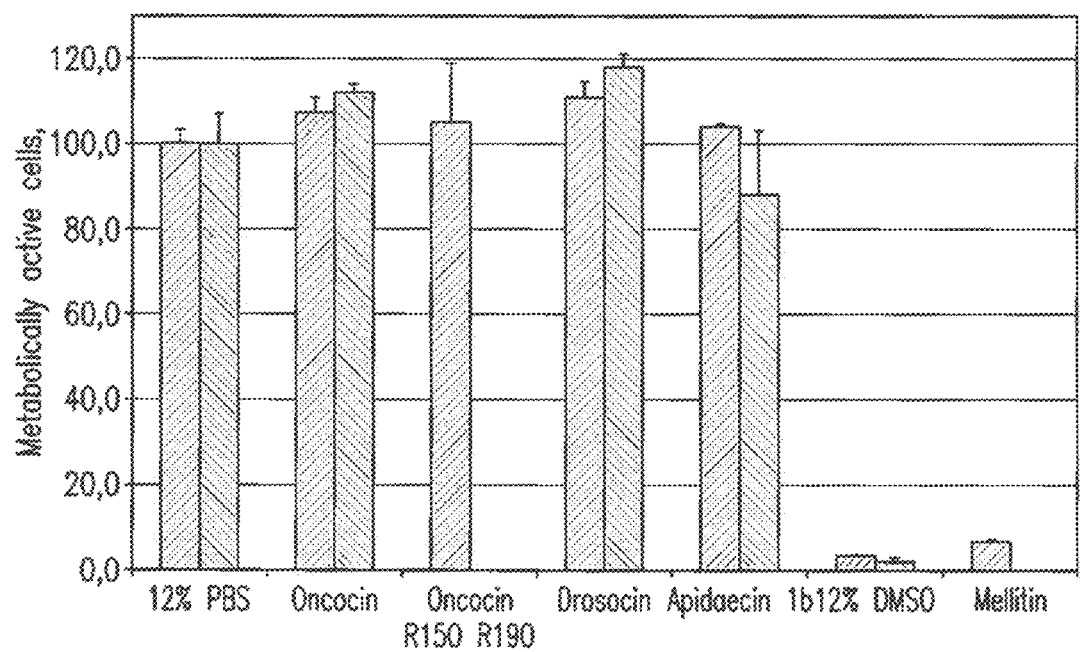
FIG. 6 shows the results of the cytotoxicity test for the antimicrobial peptides against SH-SY5Y (cross-hatched column) and HeLa cells (black column) determined with the "Cell Proliferation Kit I". Test after 24 h incubation with 600 μg/mL oncocin, oncocin R15O R19O, drosocin and apidaecin 1b (SEQ ID NO. 18, 72, 89 and 87) in medium. Positive controls 12% DMSO and 100 μg/mL melittin. Normalized to negative control 12% PBS.
Figure 7:
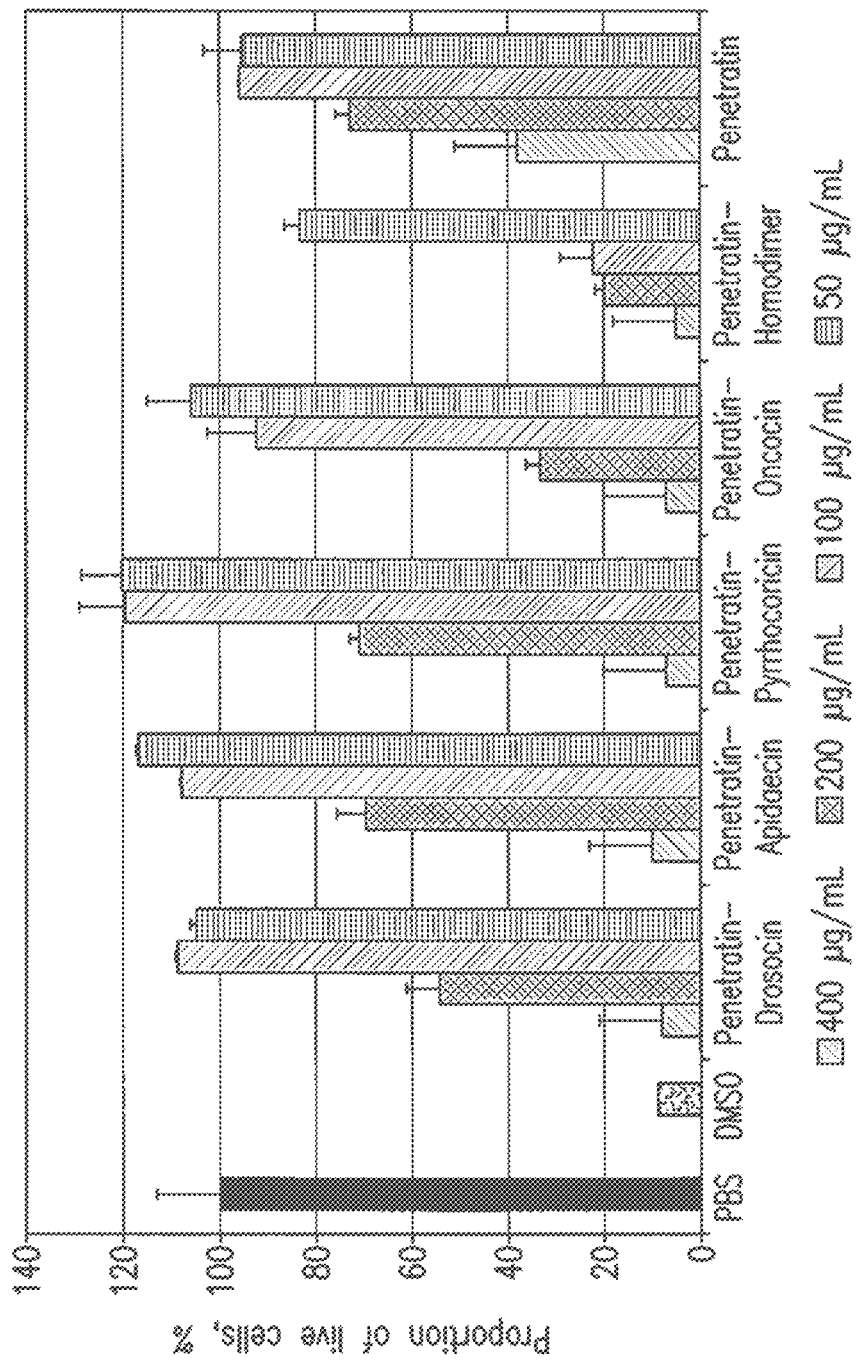
FIG. 7 shows the results of the cytotoxicity test for the penetratin constructs against HeLa cells determined with the "Cell Proliferation Kit I". Test after 24 h incubation with 50-400 μg/mL penetratin-drosocin (SEQ ID NO. 96), penetratin-apidaecin 1b (SEQ ID NO. 94), penetratin-pyrrhocoricin (SEQ ID NO. 98), penetratin-oncocin (SEQ ID NO. 100), penetratin homodimer (SEQ ID NO. 102), penetratin (SEQ ID NO. 105) in medium. Negative control 12% PBS and positive control 12% DMSO.
Figure 8:
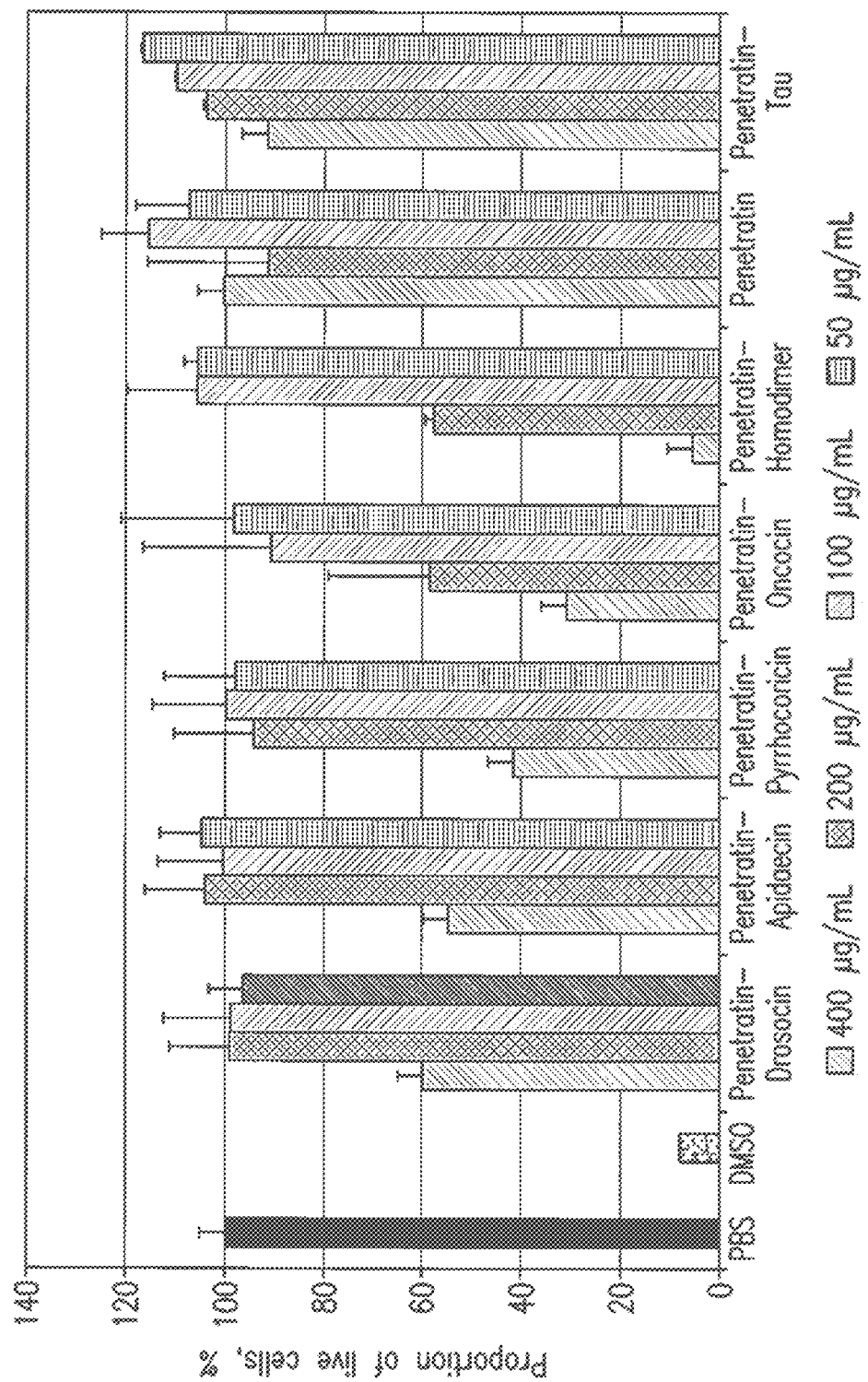
FIG. 8 shows the results of the cytotoxicity test for the penetratin constructs against SH-SY5Y cells determined with the "Cell Proliferation Kit I". Test after 24 h incubation with 50-400 μg/mL penetratin-drosocin (SEQ ID NO. 96), penetratin-apidaecin 1b (SEQ ID NO. 94), penetratin-pyrrhocoricin (SEQ ID NO. 98), penetratin-oncocin (SEQ ID NO. 100), penetratin homodimer (SEQ ID NO. 102), penetratin (SEQ ID NO. 105), penetratin-tau (SEQ ID NO. 106) in medium. 12% PBS used as negative control and 12% DMSO as positive control.
Figure 9:
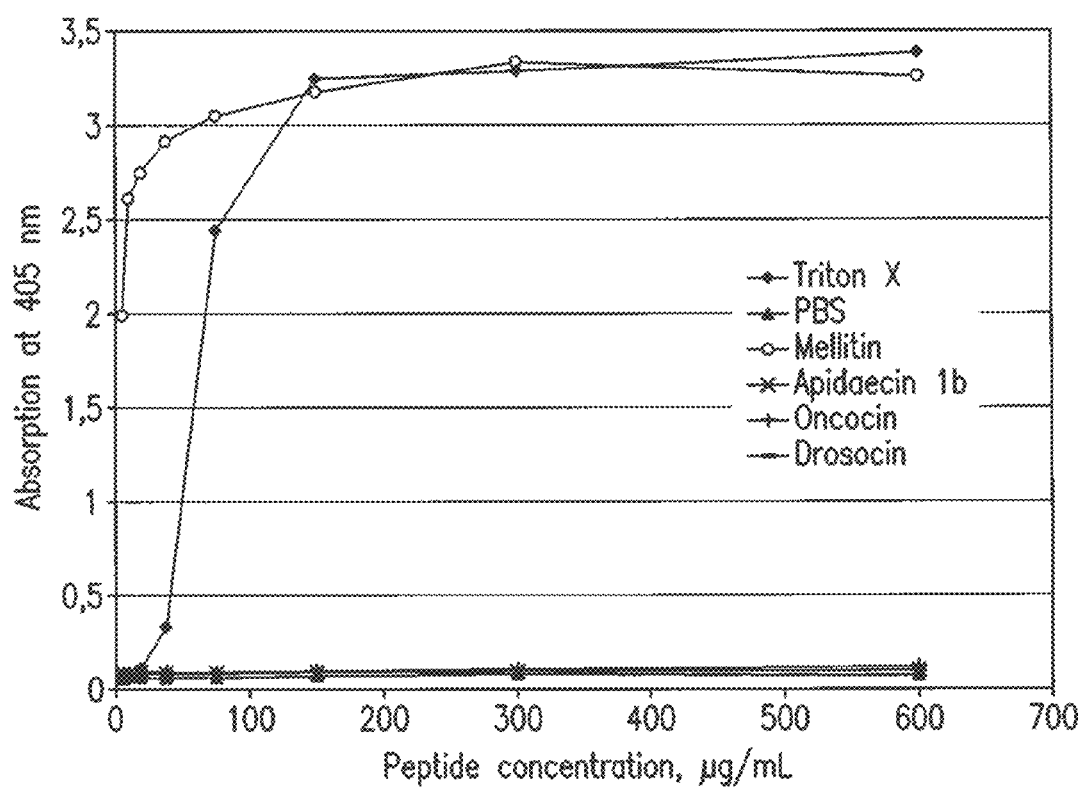
FIG. 9 shows the results of the hemolysis test for the peptides oncocin, drosocin and apidaecin 1b (SEQ ID NO. 18, 89 and 87). Peptide dilution series 4.7-600 μg/mL. Positive controls: melittin and Triton X-100®, negative control PBS.
Figure 10:
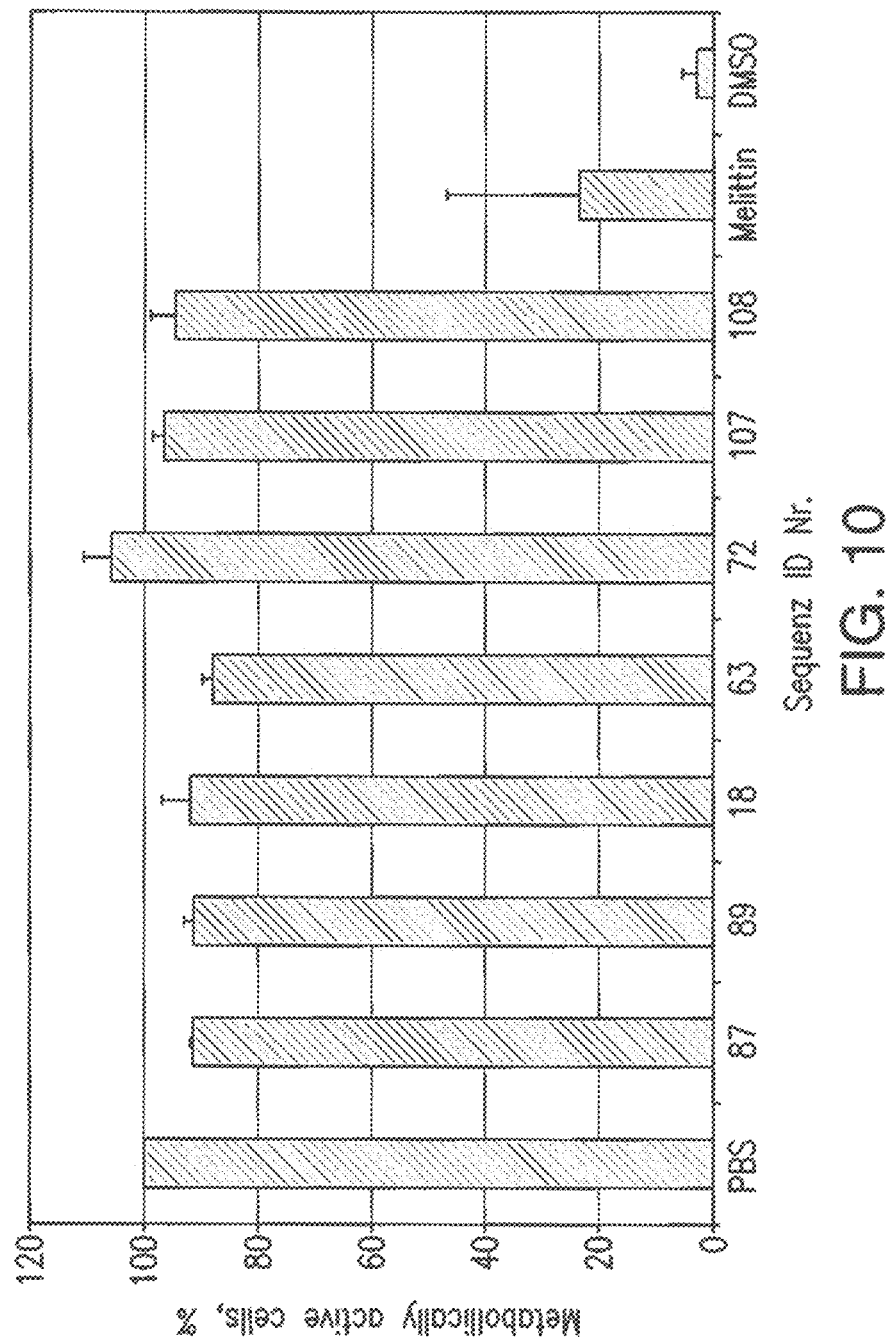
FIG. 10: shows the results of the cytotoxicity test for the antimicrobial peptides against HeLa cells determined with the "Cell Proliferation Kit I". Test after 24 h incubation with 600 μg/mL oncocin and oncocin derivatives (SEQ ID NO. 18, 63, 72, 107 to 110), and the comparative examples apidaecin 1b and drosocin (SEQ ID NO. 87 and 89) in medium. Positive controls 12% DMSO and 100 μg/mL melittin. Normalized to negative control 12% PBS. The diagram shows the mean value of two independent tests with triplicates.

```
<160> NUMBER OF SEQ ID NOS: 126

<210> SEQ ID NO 1
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (18)..(18)
<223> OTHER INFORMATION: Xaa is Asparagine amide

<400> SEQUENCE: 1

Val Asp Lys Pro Pro Tyr Leu Pro Arg Pro Pro Pro Pro Arg Arg Ile
1               5                   10                  15

Tyr Xaa

<210> SEQ ID NO 2
<211> LENGTH: 20
<212> TYPE: PRT
<213> ORGANISM: Artificial Sequence
<220> FEATURE:
<223> OTHER INFORMATION: Artificial Peptide

<400> SEQUENCE: 2

Val Asp Lys Pro Pro Tyr Leu Pro Arg Pro Pro Pro Pro Arg Arg Ile
1               5                   10                  15

Tyr Asn Asn Arg
            20

<210> SEQ ID NO 3
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (11)..(11)
```

<223> OTHER INFORMATION: Xaa is 4Hyp

<400> SEQUENCE: 3

Val Asp Lys Pro Pro Tyr Leu Pro Arg Pro Xaa Pro Pro Arg Arg Ile
1               5                   10                  15

Tyr Asn Arg

<210> SEQ ID NO 4
<211> LENGTH: 20
<212> TYPE: PRT
<213> ORGANISM: Artificial Sequence
<220> FEATURE:
<223> OTHER INFORMATION: Artificial Peptide

<400> SEQUENCE: 4

Val Asp Lys Pro Pro Tyr Leu Pro Arg Pro Thr Pro Pro Arg Arg Ile
1               5                   10                  15

Tyr Asn Asn Arg
            20

<210> SEQ ID NO 5
<211> LENGTH: 20
<212> TYPE: PRT
<213> ORGANISM: Artificial Sequence
<220> FEATURE:
<223> OTHER INFORMATION: Artificial Peptide

<400> SEQUENCE: 5

Val Asp Lys Pro Pro Tyr Leu Pro Arg Pro Lys Pro Pro Arg Arg Ile
1               5                   10                  15

Tyr Asn Asn Arg
            20

<210> SEQ ID NO 6
<211> LENGTH: 20
<212> TYPE: PRT
<213> ORGANISM: Artificial Sequence
<220> FEATURE:
<223> OTHER INFORMATION: Artificial Peptide

<400> SEQUENCE: 6

Val Asp Lys Pro Pro Tyr Leu Pro Arg Pro Lys Pro Pro Arg Arg Ile
1               5                   10                  15

Tyr Asn Arg Asn
            20

<210> SEQ ID NO 7
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 7

Val Asp Lys Pro Pro Tyr Leu Pro Arg Pro Lys Pro Pro Arg Arg Ile
1               5                   10                  15

Tyr Asn Xaa

<210> SEQ ID NO 8
<211> LENGTH: 20
<212> TYPE: PRT

<213> ORGANISM: Artificial Sequence
<220> FEATURE:
<223> OTHER INFORMATION: Artificial Peptide

<400> SEQUENCE: 8

Val Asp Lys Pro Pro Tyr Leu Pro Arg Pro His Pro Pro Arg Arg Ile
1               5                   10                  15

Tyr Asn Asn Arg
            20

<210> SEQ ID NO 9
<211> LENGTH: 20
<212> TYPE: PRT
<213> ORGANISM: Artificial Sequence
<220> FEATURE:
<223> OTHER INFORMATION: Artificial Peptide

<400> SEQUENCE: 9

Val Asp Lys Pro Pro Tyr Leu Pro Arg Pro His Pro Pro Arg Arg Ile
1               5                   10                  15

Tyr Asn Arg Asn
            20

<210> SEQ ID NO 10
<211> LENGTH: 19
<212> TYPE: PRT
<213> ORGANISM: Artificial Sequence
<220> FEATURE:
<223> OTHER INFORMATION: Artificial peptide

<400> SEQUENCE: 10

Val Asp Lys Pro Pro Tyr Leu Pro Arg Pro Tyr Pro Pro Arg Arg Ile
1               5                   10                  15

Tyr Asn Arg

<210> SEQ ID NO 11
<211> LENGTH: 19
<212> TYPE: PRT
<213> ORGANISM: Artificial Sequence
<220> FEATURE:
<223> OTHER INFORMATION: Artificial Peptide

<400> SEQUENCE: 11

Val Asp Lys Pro Pro Tyr Leu Pro Arg Pro Asn Pro Pro Arg Arg Ile
1               5                   10                  15

Tyr Asn Arg

<210> SEQ ID NO 12
<211> LENGTH: 19
<212> TYPE: PRT
<213> ORGANISM: Artificial Sequence
<220> FEATURE:
<223> OTHER INFORMATION: Artificial Peptide

<400> SEQUENCE: 12

Val Asp Lys Pro Pro Tyr Leu Pro Arg Pro Gln Pro Pro Arg Arg Ile
1               5                   10                  15

Tyr Asn Arg

<210> SEQ ID NO 13
<211> LENGTH: 19
<212> TYPE: PRT
<213> ORGANISM: Artificial Sequence
<220> FEATURE:
<223> OTHER INFORMATION: Artificial Peptide

```
<400> SEQUENCE: 13

Val Asp Lys Pro Pro Tyr Leu Pro Arg Pro Phe Pro Arg Arg Ile
1               5                   10                  15

Tyr Asn Arg

<210> SEQ ID NO 14
<211> LENGTH: 20
<212> TYPE: PRT
<213> ORGANISM: Artificial Sequence
<220> FEATURE:
<223> OTHER INFORMATION: Artificial Peptide

<400> SEQUENCE: 14

Val Asp Lys Pro Pro Tyr Leu Pro Arg Pro Arg Pro Arg Arg Ile
1               5                   10                  15

Tyr Asn Asn Arg
            20

<210> SEQ ID NO 15
<211> LENGTH: 20
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (20)..(20)
<223> OTHER INFORMATION: Xaa is Arginine amide

<400> SEQUENCE: 15

Val Asp Lys Pro Pro Tyr Leu Pro Arg Pro Arg Pro Arg Arg Ile
1               5                   10                  15

Tyr Asn Asn Xaa
            20

<210> SEQ ID NO 16
<211> LENGTH: 20
<212> TYPE: PRT
<213> ORGANISM: Artificial Sequence
<220> FEATURE:
<223> OTHER INFORMATION: Artificial Peptide

<400> SEQUENCE: 16

Val Asp Lys Pro Pro Tyr Leu Pro Arg Pro Arg Pro Arg Arg Ile
1               5                   10                  15

Tyr Asn Arg Asn
            20

<210> SEQ ID NO 17
<211> LENGTH: 20
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (20)..(20)
<223> OTHER INFORMATION: Xaa is Asparagine amide

<400> SEQUENCE: 17

Val Asp Lys Pro Pro Tyr Leu Pro Arg Pro Arg Pro Arg Arg Ile
1               5                   10                  15

Tyr Asn Arg Xaa
            20
```

```
<210> SEQ ID NO 18
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 18

Val Asp Lys Pro Pro Tyr Leu Pro Arg Pro Arg Pro Arg Arg Ile
1               5                   10                  15

Tyr Asn Xaa

<210> SEQ ID NO 19
<211> LENGTH: 19
<212> TYPE: PRT
<213> ORGANISM: Artificial Sequence
<220> FEATURE:
<223> OTHER INFORMATION: Artificial Peptide

<400> SEQUENCE: 19

Val Asp Lys Pro Pro Tyr Leu Pro Arg Pro Arg Pro Arg Arg Ile
1               5                   10                  15

Tyr Asn Arg

<210> SEQ ID NO 20
<211> LENGTH: 19
<212> TYPE: PRT
<213> ORGANISM: Artificial Sequence
<220> FEATURE:
<223> OTHER INFORMATION: Artificial Peptide

<400> SEQUENCE: 20

Val Asp Lys Pro Pro Tyr Leu Pro Arg Pro Arg Pro Arg Pro Ile
1               5                   10                  15

Tyr Asn Arg

<210> SEQ ID NO 21
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (8)..(8)
<223> OTHER INFORMATION: Xaa is 4Hyp

<400> SEQUENCE: 21

Val Asp Lys Pro Pro Tyr Leu Xaa Arg Pro Arg Pro Arg Arg Ile
1               5                   10                  15

Tyr Asn Arg

<210> SEQ ID NO 22
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (8)..(8)
<223> OTHER INFORMATION: Xaa is 4Hyp
<220> FEATURE:
```

```
<221> NAME/KEY: misc_feature
<222> LOCATION: (19)..(19)
<223> OTHER INFORMATION: Xaa is Arginine amide

<400> SEQUENCE: 22

Val Asp Lys Pro Pro Tyr Leu Xaa Arg Pro Arg Pro Pro Arg Arg Ile
1               5                   10                  15

Tyr Asn Xaa

<210> SEQ ID NO 23
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (4)..(4)
<223> OTHER INFORMATION: Xaa is 4Hyp

<400> SEQUENCE: 23

Val Asp Lys Xaa Pro Tyr Leu Pro Arg Pro Arg Pro Pro Arg Arg Ile
1               5                   10                  15

Tyr Asn Arg

<210> SEQ ID NO 24
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (13)..(13)
<223> OTHER INFORMATION: Xaa is 4Hyp
<220> FEATURE:
<221> NAME/KEY: misc_feature
<222> LOCATION: (19)..(19)
<223> OTHER INFORMATION: Xaa is Arginine amide

<400> SEQUENCE: 24

Val Asp Lys Pro Pro Tyr Leu Pro Arg Pro Arg Pro Xaa Arg Arg Ile
1               5                   10                  15

Tyr Asn Xaa

<210> SEQ ID NO 25
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is 4Hyp
<220> FEATURE:
<221> NAME/KEY: misc_feature
<222> LOCATION: (19)..(19)
<223> OTHER INFORMATION: Xaa is Arginine amide

<400> SEQUENCE: 25

Val Asp Lys Pro Pro Tyr Leu Pro Arg Pro Arg Pro Pro Arg Xaa Ile
1               5                   10                  15

Tyr Asn Xaa

<210> SEQ ID NO 26
<211> LENGTH: 20
<212> TYPE: PRT
```

<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Orn
<220> FEATURE:
<221> NAME/KEY: misc_feature
<222> LOCATION: (20)..(20)
<223> OTHER INFORMATION: Xaa is Asparagine amide

<400> SEQUENCE: 26

Val Asp Lys Pro Pro Tyr Leu Pro Arg Pro Arg Pro Arg Arg Ile
1               5                   10                  15

Tyr Asn Xaa Xaa
            20

<210> SEQ ID NO 27
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (18)..(18)
<223> OTHER INFORMATION: Xaa is Asparagine amide

<400> SEQUENCE: 27

Val Asp Lys Pro Pro Tyr Leu Pro Arg Pro Arg Pro Arg Arg Ile
1               5                   10                  15

Tyr Xaa

<210> SEQ ID NO 28
<211> LENGTH: 18
<212> TYPE: PRT
<213> ORGANISM: Artificial Sequence
<220> FEATURE:
<223> OTHER INFORMATION: Artificial Peptide

<400> SEQUENCE: 28

Val Asp Lys Pro Pro Tyr Leu Pro Arg Pro Arg Pro Arg Arg Ile
1               5                   10                  15

Tyr Asn

<210> SEQ ID NO 29
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 29

Ala Asp Lys Pro Pro Tyr Leu Pro Arg Pro Arg Pro Arg Arg Ile
1               5                   10                  15

Tyr Asn Xaa

<210> SEQ ID NO 30
<211> LENGTH: 19
<212> TYPE: PRT
<213> ORGANISM: Artificial Sequence
<220> FEATURE:
<223> OTHER INFORMATION: Artificial Peptide

```
<220> FEATURE:
<221> NAME/KEY: misc_feature
<222> LOCATION: (19)..(19)
<223> OTHER INFORMATION: Xaa is Arginine amide

<400> SEQUENCE: 30

Val Ala Lys Pro Pro Tyr Leu Pro Arg Pro Arg Pro Pro Arg Arg Ile
1               5                   10                  15

Tyr Asn Xaa

<210> SEQ ID NO 31
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 31

Val Asp Ala Pro Pro Tyr Leu Pro Arg Pro Arg Pro Pro Arg Arg Ile
1               5                   10                  15

Tyr Asn Xaa

<210> SEQ ID NO 32
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 32

Val Asp Lys Ala Pro Tyr Leu Pro Arg Pro Arg Pro Pro Arg Arg Ile
1               5                   10                  15

Tyr Asn Xaa

<210> SEQ ID NO 33
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 33

Val Asp Lys Pro Ala Tyr Leu Pro Arg Pro Arg Pro Pro Arg Arg Ile
1               5                   10                  15

Tyr Asn Xaa

<210> SEQ ID NO 34
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide
```

```
<400> SEQUENCE: 34

Val Asp Lys Pro Pro Ala Leu Pro Arg Pro Arg Pro Pro Arg Arg Ile
1               5                   10                  15

Tyr Asn Xaa

<210> SEQ ID NO 35
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 35

Val Asp Lys Pro Pro Tyr Ala Pro Arg Pro Arg Pro Pro Arg Arg Ile
1               5                   10                  15

Tyr Asn Xaa

<210> SEQ ID NO 36
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 36

Val Asp Lys Pro Pro Tyr Leu Ala Arg Pro Arg Pro Pro Arg Arg Ile
1               5                   10                  15

Tyr Asn Xaa

<210> SEQ ID NO 37
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 37

Val Asp Lys Pro Pro Tyr Leu Pro Ala Pro Arg Pro Pro Arg Arg Ile
1               5                   10                  15

Tyr Asn Xaa

<210> SEQ ID NO 38
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 38

Val Asp Lys Pro Pro Tyr Leu Pro Arg Ala Arg Pro Pro Arg Arg Ile
```

-continued

```
1               5                   10                  15
Tyr Asn Xaa

<210> SEQ ID NO 39
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 39

Val Asp Lys Pro Pro Tyr Leu Pro Arg Pro Ala Pro Arg Arg Ile
1               5                   10                  15

Tyr Asn Xaa

<210> SEQ ID NO 40
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 40

Val Asp Lys Pro Pro Tyr Leu Pro Arg Pro Arg Ala Pro Arg Ile
1               5                   10                  15

Tyr Asn Xaa

<210> SEQ ID NO 41
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 41

Val Asp Lys Pro Pro Tyr Leu Pro Arg Pro Arg Pro Ala Arg Ile
1               5                   10                  15

Tyr Asn Xaa

<210> SEQ ID NO 42
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 42

Val Asp Lys Pro Pro Tyr Leu Pro Arg Pro Arg Pro Pro Ala Ile
1               5                   10                  15

Tyr Asn Xaa
```

```
<210> SEQ ID NO 43
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 43

Val Asp Lys Pro Pro Tyr Leu Pro Arg Pro Arg Pro Arg Ala Ile
1               5                   10                  15

Tyr Asn Xaa

<210> SEQ ID NO 44
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 44

Val Asp Lys Pro Pro Tyr Leu Pro Arg Pro Arg Pro Arg Arg Ala
1               5                   10                  15

Tyr Asn Xaa

<210> SEQ ID NO 45
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 45

Val Asp Lys Pro Pro Tyr Leu Pro Arg Pro Arg Pro Arg Arg Ile
1               5                   10                  15

Ala Asn Xaa

<210> SEQ ID NO 46
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 46

Val Asp Lys Pro Pro Tyr Leu Pro Arg Pro Arg Pro Arg Arg Ile
1               5                   10                  15

Tyr Ala Xaa

<210> SEQ ID NO 47
<211> LENGTH: 19
<212> TYPE: PRT
```

```
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Alanine amide

<400> SEQUENCE: 47

Val Asp Lys Pro Pro Tyr Leu Pro Arg Pro Arg Pro Pro Arg Arg Ile
1               5                   10                  15

Tyr Asn Xaa

<210> SEQ ID NO 48
<211> LENGTH: 18
<212> TYPE: PRT
<213> ORGANISM: Artificial Sequence
<220> FEATURE:
<223> OTHER INFORMATION: Artificial Peptide

<400> SEQUENCE: 48

Val Asp Lys Pro Pro Tyr Leu Pro Arg Pro Arg Pro Pro Arg Pro Ile
1               5                   10                  15

Arg Val

<210> SEQ ID NO 49
<211> LENGTH: 27
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (27)..(27)
<223> OTHER INFORMATION: Xaa is Leucine amide

<400> SEQUENCE: 49

Val Asp Lys Pro Pro Tyr Leu Pro Arg Pro Arg Pro Pro Arg Arg Ile
1               5                   10                  15

Tyr Pro Gln Pro Arg Pro Pro His Pro Arg Xaa
            20                  25

<210> SEQ ID NO 50
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Ornithine amide

<400> SEQUENCE: 50

Val Asp Lys Pro Pro Tyr Leu Pro Arg Pro Arg Pro Pro Arg Arg Ile
1               5                   10                  15

Tyr Asn Xaa

<210> SEQ ID NO 51
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Asparagine amide
```

<400> SEQUENCE: 51

Val Asp Lys Pro Pro Tyr Leu Pro Arg Pro Arg Pro Pro Arg Arg Ile
1               5                   10                  15

Tyr Asn Xaa

<210> SEQ ID NO 52
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is 2,3-Diamino-3-N-acetylpropionic acid
      amide

<400> SEQUENCE: 52

Val Asp Lys Pro Pro Tyr Leu Pro Arg Pro Arg Pro Pro Arg Arg Ile
1               5                   10                  15

Tyr Asn Xaa

<210> SEQ ID NO 53
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Histidine amide

<400> SEQUENCE: 53

Val Asp Lys Pro Pro Tyr Leu Pro Arg Pro Arg Pro Pro Arg Arg Ile
1               5                   10                  15

Tyr Asn Xaa

<210> SEQ ID NO 54
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is 2-Amino-3-guanidinopropionic acid amide

<400> SEQUENCE: 54

Val Asp Lys Pro Pro Tyr Leu Pro Arg Pro Arg Pro Pro Arg Arg Ile
1               5                   10                  15

Tyr Asn Xaa

<210> SEQ ID NO 55
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Nitroarginine amide

<400> SEQUENCE: 55

```
Val Asp Lys Pro Pro Tyr Leu Pro Arg Pro Arg Pro Pro Arg Arg Ile
1               5                   10                  15

Tyr Asn Xaa

<210> SEQ ID NO 56
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is N-Methyl-arginine amide

<400> SEQUENCE: 56

Val Asp Lys Pro Pro Tyr Leu Pro Arg Pro Arg Pro Pro Arg Arg Ile
1               5                   10                  15

Tyr Asn Xaa

<210> SEQ ID NO 57
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Homoarginine amide

<400> SEQUENCE: 57

Val Asp Lys Pro Pro Tyr Leu Pro Arg Pro Arg Pro Pro Arg Arg Ile
1               5                   10                  15

Tyr Asn Xaa

<210> SEQ ID NO 58
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine propyl amide

<400> SEQUENCE: 58

Val Asp Lys Pro Pro Tyr Leu Pro Arg Pro Arg Pro Pro Arg Arg Ile
1               5                   10                  15

Tyr Asn Xaa

<210> SEQ ID NO 59
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 59

Val Asp Lys Pro Pro Tyr Leu Pro Arg Pro Arg Pro Arg Pro Arg Ile
1               5                   10                  15

Tyr Asn Xaa
```

```
<210> SEQ ID NO 60
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 60

Val Asp Lys Pro Pro Tyr Leu Pro Arg Pro Arg Pro Pro Arg Pro Ile
1               5                   10                  15

Tyr Asn Xaa

<210> SEQ ID NO 61
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Arginine amide

<400> SEQUENCE: 61

Val Asp Lys Pro Pro Tyr Leu Pro Arg Pro Arg Pro Pro Arg Xaa Ile
1               5                   10                  15

Tyr Asn Xaa

<210> SEQ ID NO 62
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is beta-Homoarginine
<220> FEATURE:
<221> NAME/KEY: misc_feature
<222> LOCATION: (19)..(19)
<223> OTHER INFORMATION: Xaa is Arginine amide

<400> SEQUENCE: 62

Val Asp Lys Pro Pro Tyr Leu Pro Arg Pro Arg Pro Pro Arg Xaa Ile
1               5                   10                  15

Tyr Asn Xaa

<210> SEQ ID NO 63
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is 4Hyp
<220> FEATURE:
<221> NAME/KEY: misc_feature
<222> LOCATION: (19)..(19)
```

<223> OTHER INFORMATION: Xaa is Ornithine amide

<400> SEQUENCE: 63

Val Asp Lys Pro Pro Tyr Leu Pro Arg Pro Arg Pro Pro Arg Xaa Ile
1               5                   10                  15

Tyr Asn Xaa

<210> SEQ ID NO 64
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Histidine amide

<400> SEQUENCE: 64

Val Asp Lys Pro Pro Tyr Leu Pro Arg Pro Arg Pro Pro Arg His Ile
1               5                   10                  15

Tyr Asn Xaa

<210> SEQ ID NO 65
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is 2-Amino-3-guanidinopropionic acid
<220> FEATURE:
<221> NAME/KEY: misc_feature
<222> LOCATION: (19)..(19)
<223> OTHER INFORMATION: Xaa is Homoarginine amide

<400> SEQUENCE: 65

Val Asp Lys Pro Pro Tyr Leu Pro Arg Pro Arg Pro Pro Arg Xaa Ile
1               5                   10                  15

Tyr Asn Xaa

<210> SEQ ID NO 66
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is 2-Amino-3-guanidinopropionic acid
<220> FEATURE:
<221> NAME/KEY: misc_feature
<222> LOCATION: (19)..(19)
<223> OTHER INFORMATION: Xaa is 2-Amino-3-guanidinopropionic acid amide

<400> SEQUENCE: 66

Val Asp Lys Pro Pro Tyr Leu Pro Arg Pro Arg Pro Pro Arg Xaa Ile
1               5                   10                  15

Tyr Asn Xaa

<210> SEQ ID NO 67
<211> LENGTH: 19
<212> TYPE: PRT
<213> ORGANISM: Artificial Sequence
<220> FEATURE:

<223> OTHER INFORMATION: Artificial Peptide
<220> FEATURE:
<221> NAME/KEY: misc_feature
<222> LOCATION: (15)..(15)
<223> OTHER INFORMATION: Xaa is Homoarginine
<220> FEATURE:
<221> NAME/KEY: misc_feature
<222> LOCATION: (19)..(19)
<223> OTHER INFORMATION: Xaa is is Homoarginine amide

<400> SEQUENCE: 67

Val Asp Lys Pro Pro Tyr Leu Pro Arg Pro Arg Pro Pro Arg Xaa Ile
1               5                   10                  15

Tyr Asn Xaa

<210> SEQ ID NO 68
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Homoarginine
<220> FEATURE:
<221> NAME/KEY: misc_feature
<222> LOCATION: (19)..(19)
<223> OTHER INFORMATION: Xaa is 2-Amino-3-guanidinopropionic acid amide

<400> SEQUENCE: 68

Val Asp Lys Pro Pro Tyr Leu Pro Arg Pro Arg Pro Pro Arg Xaa Ile
1               5                   10                  15

Tyr Asn Xaa

<210> SEQ ID NO 69
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is 2-Amino-3-guanidinopropionic acid amide

<400> SEQUENCE: 69

Val Asp Lys Pro Pro Tyr Leu Pro Arg Pro Arg Pro Pro Arg Xaa Ile
1               5                   10                  15

Tyr Asn Xaa

<210> SEQ ID NO 70
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Homoarginine amide

<400> SEQUENCE: 70

```
Val Asp Lys Pro Pro Tyr Leu Pro Arg Pro Arg Pro Arg Xaa Ile
1               5                   10                  15

Tyr Asn Xaa
```

<210> SEQ ID NO 71
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Arginine propyl amide

<400> SEQUENCE: 71

```
Val Asp Lys Pro Pro Tyr Leu Pro Arg Pro Arg Pro Arg Xaa Ile
1               5                   10                  15

Tyr Asn Xaa
```

<210> SEQ ID NO 72
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Ornithine amide

<400> SEQUENCE: 72

```
Val Asp Lys Pro Pro Tyr Leu Pro Arg Pro Arg Pro Arg Xaa Ile
1               5                   10                  15

Tyr Asn Xaa
```

<210> SEQ ID NO 73
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Ornithine amide

<400> SEQUENCE: 73

```
Val Asp Lys Pro Pro Tyr Leu Pro Arg Pro Arg Pro Arg Xaa Leu
1               5                   10                  15

Tyr Asn Xaa
```

<210> SEQ ID NO 74
<211> LENGTH: 19
<212> TYPE: PRT
<213> ORGANISM: Artificial Sequence

```
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is is Ornithine amide

<400> SEQUENCE: 74

Val Asp Lys Pro Pro Tyr Leu Pro Arg Pro Arg Pro Pro Arg Xaa Ile
1               5                   10                  15

Tyr Gln Xaa

<210> SEQ ID NO 75
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 75

Val Glu Lys Pro Pro Tyr Leu Pro Arg Pro Arg Pro Pro Arg Arg Ile
1               5                   10                  15

Tyr Asn Xaa

<210> SEQ ID NO 76
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 76

Val Asp Arg Pro Pro Tyr Leu Pro Arg Pro Arg Pro Pro Arg Arg Ile
1               5                   10                  15

Tyr Asn Xaa

<210> SEQ ID NO 77
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 77

Val Asp Lys Pro Pro Tyr Ile Pro Arg Pro Arg Pro Pro Arg Arg Ile
1               5                   10                  15

Tyr Asn Xaa

<210> SEQ ID NO 78
<211> LENGTH: 19
<212> TYPE: PRT
<213> ORGANISM: Artificial Sequence
```

```
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 78

Val Asp Lys Pro Pro Tyr Leu Pro Arg Pro Arg Pro Pro Arg Arg Leu
1               5                   10                  15

Tyr Asn Xaa

<210> SEQ ID NO 79
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 79

Val Asp Lys Pro Pro Tyr Leu Pro Arg Pro Arg Pro Pro Arg Arg Ile
1               5                   10                  15

Tyr Gln Xaa

<210> SEQ ID NO 80
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Valine

<400> SEQUENCE: 80

Xaa Asp Lys Pro Pro Tyr Leu Pro Arg Pro Arg Pro Pro Arg Arg Ile
1               5                   10                  15

Tyr Asn Arg

<210> SEQ ID NO 81
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Formyl-Valine

<400> SEQUENCE: 81

Xaa Asp Lys Pro Pro Tyr Leu Pro Arg Pro Arg Pro Pro Arg Arg Ile
1               5                   10                  15

Tyr Asn Arg

<210> SEQ ID NO 82
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
```

```
<222> LOCATION: (1)..(1)
<223> OTHER INFORMATION: Xaa is Ornithine
<220> FEATURE:
<221> NAME/KEY: misc_feature
<222> LOCATION: (19)..(19)
<223> OTHER INFORMATION: Xaa is Arginine amide

<400> SEQUENCE: 82

Xaa Asp Lys Pro Pro Tyr Leu Pro Arg Pro Arg Pro Arg Arg Ile
1               5                   10                  15

Tyr Asn Xaa

<210> SEQ ID NO 83
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-alpha-Acetyl-Ornithine
<220> FEATURE:
<221> NAME/KEY: misc_feature
<222> LOCATION: (19)..(19)
<223> OTHER INFORMATION: Xaa is Arginine amide

<400> SEQUENCE: 83

Xaa Asp Lys Pro Pro Tyr Leu Pro Arg Pro Arg Pro Arg Arg Ile
1               5                   10                  15

Tyr Asn Xaa

<210> SEQ ID NO 84
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Guanidino-Valine
<220> FEATURE:
<221> NAME/KEY: misc_feature
<222> LOCATION: (19)..(19)
<223> OTHER INFORMATION: Xaa is Arginine amide

<400> SEQUENCE: 84

Xaa Asp Lys Pro Pro Tyr Leu Pro Arg Pro Arg Pro Arg Arg Ile
1               5                   10                  15

Tyr Asn Xaa

<210> SEQ ID NO 85
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Guanidino-Valine
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Ornithine amide
```

<400> SEQUENCE: 85

Xaa Asp Lys Pro Pro Tyr Leu Pro Arg Pro Arg Pro Pro Arg Xaa Ile
1               5                   10                  15

Tyr Asn Xaa

<210> SEQ ID NO 86
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (18)..(18)
<223> OTHER INFORMATION: Xaa is Arginine amide

<400> SEQUENCE: 86

Asp Lys Pro Pro Tyr Leu Pro Arg Pro Arg Pro Pro Arg Arg Ile Tyr
1               5                   10                  15

Asn Xaa

<210> SEQ ID NO 87
<211> LENGTH: 18
<212> TYPE: PRT
<213> ORGANISM: Apis mellifera

<400> SEQUENCE: 87

Gly Asn Asn Arg Pro Val Tyr Ile Pro Gln Pro Arg Pro Pro His Pro
1               5                   10                  15

Arg Leu

<210> SEQ ID NO 88
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is 5(6)-Carboxyfluorescein-Glycine

<400> SEQUENCE: 88

Xaa Asn Asn Arg Pro Val Tyr Ile Pro Gln Pro Arg Pro Pro His Pro
1               5                   10                  15

Arg Leu

<210> SEQ ID NO 89
<211> LENGTH: 19
<212> TYPE: PRT
<213> ORGANISM: Drosophila melanogaster

<400> SEQUENCE: 89

Gly Lys Pro Arg Pro Tyr Ser Pro Arg Pro Thr Ser His Pro Arg Pro
1               5                   10                  15

Ile Arg Val

<210> SEQ ID NO 90
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature

```
<222> LOCATION: (1)..(1)
<223> OTHER INFORMATION: Xaa is 5(6)-Carboxyfluorescein-Glycine

<400> SEQUENCE: 90

Xaa Lys Pro Arg Pro Tyr Ser Pro Arg Pro Thr Ser His Pro Arg Pro
1               5                   10                  15

Ile Arg Val

<210> SEQ ID NO 91
<211> LENGTH: 20
<212> TYPE: PRT
<213> ORGANISM: Pyrrhocoris apterus
<220> FEATURE:
<221> NAME/KEY: misc_feature
<222> LOCATION: (20)..(20)
<223> OTHER INFORMATION: Xaa is Asparagine amide

<400> SEQUENCE: 91

Val Asp Lys Gly Ser Tyr Leu Pro Arg Pro Thr Pro Pro Arg Pro Ile
1               5                   10                  15

Tyr Asn Arg Xaa
        20

<210> SEQ ID NO 92
<211> LENGTH: 20
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is 5(6)-Carboxyfluorescein-Valine
<220> FEATURE:
<221> NAME/KEY: misc_feature
<222> LOCATION: (20)..(20)
<223> OTHER INFORMATION: Xaa is Asparagine amide

<400> SEQUENCE: 92

Xaa Asp Lys Gly Ser Tyr Leu Pro Arg Pro Thr Pro Pro Arg Pro Ile
1               5                   10                  15

Tyr Asn Arg Xaa
        20

<210> SEQ ID NO 93
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (19)..(19)
<223> OTHER INFORMATION: Xaa is Arginine amide

<400> SEQUENCE: 93

Val Asp Lys Pro Pro Tyr Leu Pro Arg Pro Arg Pro Pro Arg Arg Ile
1               5                   10                  15

Tyr Asn Xaa

<210> SEQ ID NO 94
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
```

```
<222> LOCATION: (1)..(1)
<223> OTHER INFORMATION: Xaa is 5(6)-Carboxyfluorescein-Valine
<220> FEATURE:
<221> NAME/KEY: misc_feature
<222> LOCATION: (19)..(19)
<223> OTHER INFORMATION: Xaa is Arginine amide

<400> SEQUENCE: 94

Xaa Asp Lys Pro Pro Tyr Leu Pro Arg Pro Arg Pro Pro Arg Arg Ile
1               5                   10                  15

Tyr Asn Xaa

<210> SEQ ID NO 95
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Glycine with
      Arg-Gln-Ile-Lys-Ile-Trp-Phe-Gln-Asn-Arg-Arg-Met-Lys-Trp-Lys-Lys-
      Cys coupled to the alpha-C of the acetyl residue via an thioether
      bond to the S of Cysteine

<400> SEQUENCE: 95

Xaa Asn Asn Arg Pro Val Tyr Ile Pro Gln Pro Arg Pro Pro His Pro
1               5                   10                  15

Arg Leu

<210> SEQ ID NO 96
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Glycine with
      N-alpha-5(6)-Carboxyfluorescein-Arg-Gln-Ile-Lys-Ile-Trp-Phe-Gln-
      Asn-Arg-Arg-Met-Lys-Trp-Lys-Lys-Cys coupled to the alpha-C of the
      acetyl residue via an thioether bond to the S of Cysteine

<400> SEQUENCE: 96

Xaa Asn Asn Arg Pro Val Tyr Ile Pro Gln Pro Arg Pro Pro His Pro
1               5                   10                  15

Arg Leu

<210> SEQ ID NO 97
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Glycine with
      Arg-Gln-Ile-Lys-Ile-Trp-Phe-Gln-Asn-Arg-Arg-Met-Lys-Trp-Lys-Lys-
      Cys coupled to the alpha-C of the acetyl residue via an thioether
      bond to the S of Cysteine

<400> SEQUENCE: 97

Xaa Lys Pro Arg Pro Tyr Ser Pro Arg Pro Thr Ser His Pro Arg Pro
1               5                   10                  15

Ile Arg Val
```

```
<210> SEQ ID NO 98
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Glycine with
      N-alpha-5(6)-Carboxyfluorescein-Arg-Gln-Ile-Lys-Ile-Trp-Phe-Gln-
      Asn-Arg-Arg-Met-Lys-Trp-Lys-Lys-Cys coupled to the alpha-C of the
      acetyl residue via an thioether bond to the S of Cysteine

<400> SEQUENCE: 98

Xaa Lys Pro Arg Pro Tyr Ser Pro Arg Pro Thr Ser His Pro Arg Pro
1               5                   10                  15

Ile Arg Val

<210> SEQ ID NO 99
<211> LENGTH: 20
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Valine with
      Arg-Gln-Ile-Lys-Ile-Trp-Phe-Gln-Asn-Arg-Arg-Met-Lys-Trp-Lys-Lys-
      Cys coupled to the alpha-C of the acetyl residue via an thioether
      bond to the S of Cysteine
<220> FEATURE:
<221> NAME/KEY: misc_feature
<222> LOCATION: (20)..(20)
<223> OTHER INFORMATION: Xaa is Asparagine amide

<400> SEQUENCE: 99

Xaa Asp Lys Gly Ser Tyr Leu Pro Arg Pro Thr Pro Pro Arg Pro Ile
1               5                   10                  15

Tyr Asn Arg Xaa
            20

<210> SEQ ID NO 100
<211> LENGTH: 20
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Valine with
      N-alpha-5(6)-Carboxyfluorescein-Arg-Gln-Ile-Lys-Ile-Trp-Phe-Gln-
      Asn-Arg-Arg-Met-Lys-Trp-Lys-Lys-Cys coupled to the alpha-C of the
      acetyl residue via an thioether bond to the S of Cysteine
<220> FEATURE:
<221> NAME/KEY: misc_feature
<222> LOCATION: (20)..(20)
<223> OTHER INFORMATION: Xaa is Asparagine amide

<400> SEQUENCE: 100

Xaa Asp Lys Gly Ser Tyr Leu Pro Arg Pro Thr Pro Pro Arg Pro Ile
1               5                   10                  15

Tyr Asn Arg Xaa
            20

<210> SEQ ID NO 101
<211> LENGTH: 19
<212> TYPE: PRT
```

```
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<220> FEATURE:
<221> NAME/KEY: misc_feature
<222> LOCATION: (19)..(19)
<223> OTHER INFORMATION: Xaa is Arginine amide

<400> SEQUENCE: 101

Xaa Asp Lys Pro Pro Tyr Leu Pro Arg Pro Arg Pro Pro Arg Arg Ile
1               5                   10                  15

Tyr Asn Xaa

<210> SEQ ID NO 102
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-Valine with
      N-alpha-5(6)-Carboxyfluorescein-Arg-Gln-Ile-Lys-Ile-Trp-Phe-Gln-
      Asn-Arg-Arg-Met-Lys-Trp-Lys-Lys-Cys coupled to the alpha-C of the
      acetyl residue via an thioether bond to the S of Cysteine
<220> FEATURE:
<221> NAME/KEY: misc_feature
<222> LOCATION: (19)..(19)
<223> OTHER INFORMATION: Xaa is Arginine amide

<400> SEQUENCE: 102

Xaa Asp Lys Pro Pro Tyr Leu Pro Arg Pro Arg Pro Pro Arg Arg Ile
1               5                   10                  15

Tyr Asn Xaa

<210> SEQ ID NO 103
<211> LENGTH: 17
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (17)..(17)
<223> OTHER INFORMATION: Xaa is Cysteine with
      Arg-Gln-Ile-Lys-Ile-Trp-Phe-Gln-Asn-Arg-Arg-Met-Lys-Trp-Lys-Lys-
      Cys coupled to the S via a disulfide bond to the S of cysteine

<400> SEQUENCE: 103

Arg Gln Ile Lys Ile Trp Phe Gln Asn Arg Arg Met Lys Trp Lys Lys
1               5                   10                  15

Xaa

<210> SEQ ID NO 104
<211> LENGTH: 17
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-alpha-5(6)-Carboxyfluorescein-Arginine
<220> FEATURE:
<221> NAME/KEY: misc_feature
<222> LOCATION: (17)..(17)
<223> OTHER INFORMATION: Xaa is Cysteine with
```

```
      N-alpha-5(6)-Carboxyfluorescein-Arg-Gln-Ile-Lys-Ile-Trp-Phe-Gln-
      Asn-Arg-Arg-Met-Lys-Trp-Lys-Lys-Cys coupled to the S via a
      disulfide bond to the S of cysteine

<400> SEQUENCE: 104

Xaa Gln Ile Lys Ile Trp Phe Gln Asn Arg Arg Met Lys Trp Lys Lys
1               5                   10                  15

Xaa

<210> SEQ ID NO 105
<211> LENGTH: 16
<212> TYPE: PRT
<213> ORGANISM: Artificial Sequence
<220> FEATURE:
<223> OTHER INFORMATION: Artificial Peptide

<400> SEQUENCE: 105

Arg Gln Ile Lys Ile Trp Phe Gln Asn Arg Arg Met Lys Trp Lys Lys
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is N-Acetyl-alpha-Amino hexanoic acid with
      Arg-Gln-Ile-Lys-Ile-Trp-Phe-Gln-Asn-Arg-Arg-Met-Lys-Trp-Lys-Lys-
      Cys coupled to the alpha-C of the acetyl residue via an thioether
      bond to the S of Cysteine
<220> FEATURE:
<221> NAME/KEY: misc_feature
<222> LOCATION: (2)..(2)
<223> OTHER INFORMATION: Xaa is alpha-Amino hexanoic acid

<400> SEQUENCE: 106

Xaa Xaa Ser Gly Asp Arg Ser Gly Tyr Ser Ser Arg Gly Ser
1               5                   10

<210> SEQ ID NO 107
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (13)..(13)
<223> OTHER INFORMATION: Xaa is 4Hyp
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (19)..(19)
<223> OTHER INFORMATION: Xaa is Ornithine amide

<400> SEQUENCE: 107

Val Asp Lys Pro Pro Tyr Leu Pro Arg Pro Arg Pro Xaa Arg Xaa Ile
1               5                   10                  15

Tyr Asn Xaa

<210> SEQ ID NO 108
<211> LENGTH: 19
<212> TYPE: PRT
<213> ORGANISM: Artificial Sequence
```

```
<220> FEATURE:
<223> OTHER INFORMATION: Artificial Peptide
<220> FEATURE:
<221> NAME/KEY: misc_feature
<222> LOCATION: (13)..(13)
<223> OTHER INFORMATION: Xaa is 4Hyp
<220> FEATURE:
<221> NAME/KEY: misc_feature
<222> LOCATION: (15)..(15)
<223> OTHER INFORMATION: Xaa is 4Hyp
<220> FEATURE:
<221> NAME/KEY: misc_feature
<222> LOCATION: (19)..(19)
<223> OTHER INFORMATION: Xaa is Ornithine amide

<400> SEQUENCE: 108

Val Asp Lys Pro Pro Tyr Leu Pro Arg Pro Arg Pro Xaa Arg Xaa Ile
1               5                   10                  15

Tyr Asn Xaa

<210> SEQ ID NO 109
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is Orn
<220> FEATURE:
<221> NAME/KEY: misc_feature
<222> LOCATION: (16)..(16)
<223> OTHER INFORMATION: Xaa is tert.-Butylglycin
<220> FEATURE:
<221> NAME/KEY: misc_feature
<222> LOCATION: (19)..(19)
<223> OTHER INFORMATION: Xaa is Ornithine amide

<400> SEQUENCE: 109

Val Asp Lys Pro Pro Tyr Leu Pro Arg Pro Arg Pro Pro Arg Xaa Xaa
1               5                   10                  15

Tyr Asn Xaa

<210> SEQ ID NO 110
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (13)..(13)
<223> OTHER INFORMATION: Xaa is 4Hyp
<220> FEATURE:
<221> NAME/KEY: misc_feature
<222> LOCATION: (15)..(15)
<223> OTHER INFORMATION: Xaa is 4Hyp
<220> FEATURE:
<221> NAME/KEY: misc_feature
<222> LOCATION: (16)..(16)
<223> OTHER INFORMATION: Xaa is tert.-Butylglycin
<220> FEATURE:
<221> NAME/KEY: misc_feature
<222> LOCATION: (19)..(19)
<223> OTHER INFORMATION: Xaa is Ornithine amide

<400> SEQUENCE: 110

Val Asp Lys Pro Pro Tyr Leu Pro Arg Pro Arg Pro Xaa Arg Xaa Xaa
1               5                   10                  15

Tyr Asn Xaa
```

```
<210> SEQ ID NO 111
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is D-Arginine
<220> FEATURE:
<221> NAME/KEY: misc_feature
<222> LOCATION: (19)..(19)
<223> OTHER INFORMATION: Xaa is Arginine amide

<400> SEQUENCE: 111

Val Asp Lys Pro Pro Tyr Leu Pro Arg Pro Arg Pro Arg Xaa Ile
1               5                   10                  15

Tyr Asn Xaa

<210> SEQ ID NO 112
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (15)..(15)
<223> OTHER INFORMATION: Xaa is D-Arginine
<220> FEATURE:
<221> NAME/KEY: misc_feature
<222> LOCATION: (19)..(19)
<223> OTHER INFORMATION: Xaa is D-Arginine amide

<400> SEQUENCE: 112

Val Asp Lys Pro Pro Tyr Leu Pro Arg Pro Arg Pro Arg Xaa Ile
1               5                   10                  15

Tyr Asn Xaa

<210> SEQ ID NO 113
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(1)
<223> OTHER INFORMATION: Xaa is Orn
<220> FEATURE:
<221> NAME/KEY: misc_feature
<222> LOCATION: (5)..(5)
<223> OTHER INFORMATION: Xaa is Orn
<220> FEATURE:
<221> NAME/KEY: misc_feature
<222> LOCATION: (19)..(19)
<223> OTHER INFORMATION: Xaa is Valine amide

<400> SEQUENCE: 113

Xaa Asn Tyr Ile Xaa Arg Pro Pro Arg Pro Arg Pro Leu Tyr Pro Pro
1               5                   10                  15

Lys Asp Xaa

<210> SEQ ID NO 114
<211> LENGTH: 19
<212> TYPE: PRT
<213> ORGANISM: Artificial Sequence
<220> FEATURE:
<223> OTHER INFORMATION: Artificial Peptide
```

```
<220> FEATURE:
<221> NAME/KEY: misc_feature
<222> LOCATION: (1)..(1)
<223> OTHER INFORMATION: Xaa is Orn
<220> FEATURE:
<221> NAME/KEY: misc_feature
<222> LOCATION: (5)..(5)
<223> OTHER INFORMATION: Xaa is 4Hyp
<220> FEATURE:
<221> NAME/KEY: misc_feature
<222> LOCATION: (19)..(19)
<223> OTHER INFORMATION: Xaa is Valine amide

<400> SEQUENCE: 114

Xaa Asn Tyr Ile Xaa Arg Pro Pro Arg Pro Arg Pro Leu Tyr Pro Pro
1               5                   10                  15

Lys Asp Xaa

<210> SEQ ID NO 115
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(19)
<223> OTHER INFORMATION: all amino acids are D-amino acids
<220> FEATURE:
<221> NAME/KEY: misc_feature
<222> LOCATION: (19)..(19)
<223> OTHER INFORMATION: Xaa is D-Arginine amide

<400> SEQUENCE: 115

Val Asp Lys Pro Pro Tyr Leu Pro Arg Pro Arg Pro Pro Arg Arg Ile
1               5                   10                  15

Tyr Asn Xaa

<210> SEQ ID NO 116
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(19)
<223> OTHER INFORMATION: all amino acids are D-amino acids
<220> FEATURE:
<221> NAME/KEY: misc_feature
<222> LOCATION: (15)..(15)
<223> OTHER INFORMATION: Xaa is D-Orn
<220> FEATURE:
<221> NAME/KEY: misc_feature
<222> LOCATION: (19)..(19)
<223> OTHER INFORMATION: Xaa is D-Ornithine amide

<400> SEQUENCE: 116

Val Asp Lys Pro Pro Tyr Leu Pro Arg Pro Arg Pro Pro Arg Xaa Ile
1               5                   10                  15

Tyr Asn Xaa

<210> SEQ ID NO 117
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(19)
```

```
<223> OTHER INFORMATION: All amino acids ar D-amino acids
<220> FEATURE:
<221> NAME/KEY: misc_feature
<222> LOCATION: (19)..(19)
<223> OTHER INFORMATION: Xaa is D-Valine amide

<400> SEQUENCE: 117

Arg Asn Tyr Ile Arg Arg Pro Pro Arg Pro Arg Pro Leu Tyr Pro Pro
1               5                   10                  15

Lys Asp Xaa

<210> SEQ ID NO 118
<211> LENGTH: 19
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (1)..(19)
<223> OTHER INFORMATION: All amino acids are D-amino acids
<220> FEATURE:
<221> NAME/KEY: misc_feature
<222> LOCATION: (1)..(1)
<223> OTHER INFORMATION: Xaa is D-Orn
<220> FEATURE:
<221> NAME/KEY: misc_feature
<222> LOCATION: (5)..(5)
<223> OTHER INFORMATION: Xaa is D-Orn
<220> FEATURE:
<221> NAME/KEY: misc_feature
<222> LOCATION: (19)..(19)
<223> OTHER INFORMATION: Xaa is D-Valine amide

<400> SEQUENCE: 118

Xaa Asn Tyr Ile Xaa Arg Pro Pro Arg Pro Arg Pro Leu Tyr Pro Pro
1               5                   10                  15

Lys Asp Xaa

<210> SEQ ID NO 119
<211> LENGTH: 18
<212> TYPE: PRT
<213> ORGANISM: Apis mellifera

<400> SEQUENCE: 119

Gly Asn Asn Arg Pro Val Tyr Ile Pro Gln Pro Arg Pro Pro His Pro
1               5                   10                  15

Arg Ile

<210> SEQ ID NO 120
<211> LENGTH: 16
<212> TYPE: PRT
<213> ORGANISM: Myrmecia gulosa

<400> SEQUENCE: 120

Gly Arg Pro Asn Pro Val Asn Asn Lys Pro Thr Pro Tyr Pro His Leu
1               5                   10                  15

<210> SEQ ID NO 121
<211> LENGTH: 15
<212> TYPE: PRT
<213> ORGANISM: Palomena prasina

<400> SEQUENCE: 121

Val Asp Lys Pro Asp Tyr Arg Pro Arg Pro Arg Pro Pro Asn Met
1               5                   10                  15
```

```
<210> SEQ ID NO 122
<211> LENGTH: 34
<212> TYPE: PRT
<213> ORGANISM: Oncopeltus fasciatus

<400> SEQUENCE: 122

Glu Val Ser Leu Lys Gly Glu Gly Gly Ser Asn Lys Gly Phe Ile Gln
1               5                   10                  15

Gly Ser Gly Thr Lys Thr Leu Phe Gln Asp Asp Lys Thr Lys Leu Asp
            20                  25                  30

Gly Thr

<210> SEQ ID NO 123
<211> LENGTH: 20
<212> TYPE: PRT
<213> ORGANISM: Oncopeltus fasciatus
<220> FEATURE:
<221> NAME/KEY: misc_feature
<222> LOCATION: (11)..(11)
<223> OTHER INFORMATION: Xaa is Pro or any other naturally occurring
      amino acid
<220> FEATURE:
<221> NAME/KEY: misc_feature
<222> LOCATION: (19)..(20)
<223> OTHER INFORMATION: Optional residues

<400> SEQUENCE: 123

Val Asp Lys Pro Pro Tyr Leu Pro Arg Pro Xaa Pro Pro Arg Arg Ile
1               5                   10                  15

Tyr Asn Asn Arg
            20

<210> SEQ ID NO 124
<211> LENGTH: 18
<212> TYPE: PRT
<213> ORGANISM: Artificial Sequence
<220> FEATURE:
<223> OTHER INFORMATION: Artificial Peptide
<220> FEATURE:
<221> NAME/KEY: misc_feature
<222> LOCATION: (18)..(18)
<223> OTHER INFORMATION: Xaa is  Alanine amide

<400> SEQUENCE: 124

Lys Leu Ala Leu Lys Leu Ala Leu Lys Ala Leu Lys Ala Ala Leu Lys
1               5                   10                  15

Leu Xaa

<210> SEQ ID NO 125
<211> LENGTH: 9
<212> TYPE: PRT
<213> ORGANISM: Artificial Sequence
<220> FEATURE:
<223> OTHER INFORMATION: Artificial Peptide

<400> SEQUENCE: 125

Arg Lys Lys Arg Arg Gln Arg Arg Arg
1               5

<210> SEQ ID NO 126
<211> LENGTH: 14
<212> TYPE: PRT
<213> ORGANISM: Artificial Sequence
<220> FEATURE:
<223> OTHER INFORMATION: Artificial Peptide
```

```
<400> SEQUENCE: 126

Val Asp Lys Pro Pro Tyr Leu Pro Arg Pro Arg Pro Pro Arg
1               5                   10
```

The invention claimed is:

1. A peptide comprising the amino acid sequence selected from the group consisting of SEQ ID NOs: 61-74, 85, 111 and 112.

2. The peptide or peptide of claim 1, wherein at least one of the peptide bonds of the peptide backbone is chemically modified.

3. The peptide of claim 2, wherein the chemically modified bond is selected from a reduced amide bond, an alkylated amide bond or a thioamide bond.

4. The peptide of claim 1, wherein said peptide is joined to a protein, or coupled to a polymer, or bound to a carrier.

5. A multimer comprising at least two peptides joined together, wherein at least one of the peptides is the peptide according to claim 1.

6. A pharmaceutical composition, comprising at least one peptide according to claim 1.

7. A method of producing a peptide according to claim 1, comprising producing the peptide by chemical synthesis or by recombinant methods.

* * * * *